United States Patent
Davis et al.

(10) Patent No.: US 10,856,846 B2
(45) Date of Patent: Dec. 8, 2020

(54) ULTRASOUND IMAGING WITH SPARSE ARRAY PROBES

(71) Applicant: MAUI IMAGING, INC., San Jose, CA (US)

(72) Inventors: Henry A. Davis, Ash Fork, AZ (US); Donald F. Specht, Los Altos, CA (US); Josef R. Call, Campbell, CA (US); Sharon L. Adam, San Jose, CA (US); David M. Smith, Lodi, CA (US); Erik Gokbora, Sunnyvale, CA (US)

(73) Assignee: MAUI IMAGING, INC., San Jose, CA (US)

( * ) Notice: Subject to any disclaimer, the term of this patent is extended or adjusted under 35 U.S.C. 154(b) by 568 days.

(21) Appl. No.: 15/418,534

(22) Filed: Jan. 27, 2017

(65) Prior Publication Data

US 2017/0209121 A1    Jul. 27, 2017

Related U.S. Application Data

(60) Provisional application No. 62/310,482, filed on Mar. 18, 2016, provisional application No. 62/287,694, filed on Jan. 27, 2016.

(51) Int. Cl.
*A61B 8/00* (2006.01)
*G01S 15/89* (2006.01)
(Continued)

(52) U.S. Cl.
CPC ............. *A61B 8/4488* (2013.01); *A61B 8/14* (2013.01); *A61B 8/4494* (2013.01);
(Continued)

(58) Field of Classification Search
CPC ......... A61B 8/44; A61B 8/4444; A61B 8/445; A61B 8/4477; A61B 8/4483; A61B 8/4488; A61B 8/4494
See application file for complete search history.

(56) References Cited

U.S. PATENT DOCUMENTS

| 3,174,286 A | 3/1965 | Erickson |
| 3,895,381 A | 7/1975 | Kock |

(Continued)

FOREIGN PATENT DOCUMENTS

| CN | 1535243 A | 10/2004 |
| CN | 1781460 A | 6/2006 |

(Continued)

OTHER PUBLICATIONS

Call et al.; U.S. Appl. No. 15/495,591 entitled "Systems and methods for improving ultrasound image quality by applying weighting factors," filed Apr. 24, 2017.

(Continued)

*Primary Examiner* — Eugene T Wu
(74) *Attorney, Agent, or Firm* — Shay Glenn LLP

(57) ABSTRACT

Sparse arrays of transducer elements may be beneficial in providing ultrasound transducer probes with a wide total aperture while containing a manageable number of transducer elements. Sparse arrays made with bulk piezoelectric materials or with arrays of micro-elements can be effectively with ping-based multiple aperture ultrasound imaging techniques to perform real-time volumetric imaging.

11 Claims, 10 Drawing Sheets

(51) Int. Cl.
*B06B 1/06* (2006.01)
*G01S 7/52* (2006.01)
*A61B 8/14* (2006.01)
*A61B 8/08* (2006.01)

(52) U.S. Cl.
CPC ........ *B06B 1/0622* (2013.01); *G01S 7/52079* (2013.01); *G01S 15/8925* (2013.01); *G01S 15/8927* (2013.01); *A61B 8/483* (2013.01)

(56) References Cited

U.S. PATENT DOCUMENTS

| | | |
|---|---|---|
| 3,974,692 A | 8/1976 | Hassler |
| 4,055,988 A | 11/1977 | Dutton |
| 4,072,922 A | 2/1978 | Taner et al. |
| 4,097,835 A | 6/1978 | Green |
| 4,105,018 A | 8/1978 | Greenleaf et al. |
| 4,180,792 A | 12/1979 | Lederman et al. |
| 4,205,394 A | 5/1980 | Pickens |
| 4,229,798 A | 10/1980 | Rosie |
| 4,259,733 A | 3/1981 | Taner et al. |
| 4,265,126 A | 5/1981 | Papadofrangakis et al. |
| 4,271,842 A | 6/1981 | Specht et al. |
| 4,325,257 A | 4/1982 | Kino et al. |
| 4,327,738 A | 5/1982 | Green et al. |
| 4,333,474 A | 6/1982 | Nigam |
| 4,339,952 A | 7/1982 | Foster |
| 4,452,084 A | 6/1984 | Taenzer |
| 4,501,279 A | 2/1985 | Seo |
| 4,511,998 A | 4/1985 | Kanda et al. |
| 4,539,847 A | 9/1985 | Paap |
| 4,566,459 A | 1/1986 | Umemura et al. |
| 4,567,768 A | 2/1986 | Satoh et al. |
| 4,604,697 A | 8/1986 | Luthra et al. |
| 4,662,222 A | 5/1987 | Johnson |
| 4,669,482 A | 6/1987 | Ophir |
| 4,682,497 A | 7/1987 | Sasaki |
| 4,694,434 A | 9/1987 | Vonn Ramm et al. |
| 4,781,199 A | 11/1988 | Hirama et al. |
| 4,817,434 A | 4/1989 | Anderson |
| 4,831,601 A | 5/1989 | Breimesser et al. |
| 4,893,284 A | 1/1990 | Magrane |
| 4,893,628 A | 1/1990 | Angelsen |
| 4,990,462 A | 2/1991 | Sliwa, Jr. |
| 5,050,588 A | 9/1991 | Grey et al. |
| 5,062,295 A | 11/1991 | Shakkottai et al. |
| 5,141,738 A | 8/1992 | Rasor et al. |
| 5,161,536 A | 11/1992 | Vilkomerson et al. |
| 5,197,475 A | 3/1993 | Antich et al. |
| 5,226,019 A | 7/1993 | Bahorich |
| 5,230,339 A | 7/1993 | Charlebois |
| 5,269,309 A | 12/1993 | Fort et al. |
| 5,278,757 A | 1/1994 | Hoctor et al. |
| 5,293,871 A | 3/1994 | Reinstein et al. |
| 5,299,576 A | 4/1994 | Shiba |
| 5,301,674 A | 4/1994 | Erikson et al. |
| 5,305,756 A | 4/1994 | Entrekin et al. |
| 5,339,282 A | 8/1994 | Kuhn et al. |
| 5,340,510 A | 8/1994 | Bowen |
| 5,345,426 A | 9/1994 | Lipschutz |
| 5,349,960 A | 9/1994 | Gondo |
| 5,355,888 A | 10/1994 | Kendall |
| 5,381,794 A | 1/1995 | Tei et al. |
| 5,398,216 A | 3/1995 | Hall et al. |
| 5,409,010 A | 4/1995 | Beach et al. |
| 5,442,462 A | 8/1995 | Guissin |
| 5,454,372 A | 10/1995 | Banjanin et al. |
| 5,503,152 A | 4/1996 | Oakley et al. |
| 5,515,853 A | 5/1996 | Smith et al. |
| 5,515,856 A | 5/1996 | Olstad et al. |
| 5,522,393 A | 6/1996 | Phillips |
| 5,526,815 A | 6/1996 | Granz et al. |
| 5,544,659 A | 8/1996 | Banjanin |
| 5,558,092 A | 9/1996 | Unger et al. |
| 5,564,423 A | 10/1996 | Mele et al. |
| 5,568,812 A | 10/1996 | Murashita et al. |
| 5,570,691 A | 11/1996 | Wright et al. |
| 5,581,517 A | 12/1996 | Gee et al. |
| 5,625,149 A | 4/1997 | Gururaja et al. |
| 5,628,320 A | 5/1997 | Teo |
| 5,673,697 A | 10/1997 | Bryan et al. |
| 5,675,550 A | 10/1997 | Ekhaus |
| 5,720,291 A | 2/1998 | Schwartz |
| 5,720,708 A | 2/1998 | Lu et al. |
| 5,744,898 A | 4/1998 | Smith et al. |
| 5,769,079 A | 6/1998 | Hossack |
| 5,784,334 A | 7/1998 | Sena et al. |
| 5,785,654 A | 7/1998 | Iinuma et al. |
| 5,795,297 A | 8/1998 | Daigle |
| 5,797,845 A | 8/1998 | Barabash et al. |
| 5,798,459 A | 8/1998 | Ohba et al. |
| 5,820,561 A | 10/1998 | Olstad et al. |
| 5,838,564 A | 11/1998 | Bahorich et al. |
| 5,850,622 A | 12/1998 | Vassiliou et al. |
| 5,862,100 A | 1/1999 | VerWest |
| 5,870,691 A | 2/1999 | Partyka et al. |
| 5,876,342 A | 3/1999 | Chen et al. |
| 5,891,038 A | 4/1999 | Seyed-Bolorforosh et al. |
| 5,892,732 A | 4/1999 | Gersztenkorn |
| 5,916,169 A | 6/1999 | Hanafy et al. |
| 5,919,139 A | 7/1999 | Lin |
| 5,920,285 A | 7/1999 | Benjamin |
| 5,930,730 A | 7/1999 | Marfurt et al. |
| 5,940,778 A | 8/1999 | Marfurt et al. |
| 5,951,479 A | 9/1999 | Holm et al. |
| 5,964,707 A | 10/1999 | Fenster et al. |
| 5,969,661 A | 10/1999 | Benjamin |
| 5,999,836 A | 12/1999 | Nelson et al. |
| 6,007,499 A | 12/1999 | Martin et al. |
| 6,013,032 A | 1/2000 | Savord |
| 6,014,473 A | 1/2000 | Hossack et al. |
| 6,048,315 A | 4/2000 | Chiao et al. |
| 6,049,509 A | 4/2000 | Sonneland et al. |
| 6,050,943 A | 4/2000 | Slayton et al. |
| 6,056,693 A | 5/2000 | Haider |
| 6,058,074 A | 5/2000 | Swan et al. |
| 6,077,224 A | 6/2000 | Lang et al. |
| 6,092,026 A | 7/2000 | Bahorich et al. |
| 6,122,538 A | 9/2000 | Sliwa, Jr. et al. |
| 6,123,670 A | 9/2000 | Mo |
| 6,129,672 A | 10/2000 | Seward et al. |
| 6,135,960 A | 10/2000 | Holmberg |
| 6,138,075 A | 10/2000 | Yost |
| 6,148,095 A | 11/2000 | Prause et al. |
| 6,162,175 A | 12/2000 | Marian, Jr. et al. |
| 6,166,384 A | 12/2000 | Dentinger et al. |
| 6,166,853 A | 12/2000 | Sapia et al. |
| 6,193,665 B1 | 2/2001 | Hall et al. |
| 6,196,739 B1 | 3/2001 | Silverbrook |
| 6,200,266 B1 | 3/2001 | Shokrollahi et al. |
| 6,210,335 B1 | 4/2001 | Miller |
| 6,213,958 B1 | 4/2001 | Winder |
| 6,221,019 B1 | 4/2001 | Kantorovich |
| 6,222,304 B1 | 4/2001 | Bernstein |
| 6,224,556 B1 * | 5/2001 | Schwartz ............... G01S 15/895 600/447 |
| 6,231,511 B1 | 5/2001 | Bae |
| 6,238,342 B1 | 5/2001 | Feleppa et al. |
| 6,246,901 B1 | 6/2001 | Benaron |
| 6,251,073 B1 | 6/2001 | Imran et al. |
| 6,264,609 B1 | 7/2001 | Herrington et al. |
| 6,266,551 B1 | 7/2001 | Osadchy et al. |
| 6,278,949 B1 | 8/2001 | Alam |
| 6,279,399 B1 * | 8/2001 | Holm ................... G10K 11/341 73/626 |
| 6,289,230 B1 | 9/2001 | Chaiken et al. |
| 6,299,580 B1 | 10/2001 | Asafusa |
| 6,304,684 B1 | 10/2001 | Niczyporuk et al. |
| 6,309,356 B1 | 10/2001 | Ustuner et al. |
| 6,324,453 B1 | 11/2001 | Breed et al. |
| 6,345,539 B1 | 2/2002 | Rawes et al. |
| 6,361,500 B1 | 3/2002 | Masters |
| 6,363,033 B1 | 3/2002 | Cole et al. |
| 6,370,480 B1 | 4/2002 | Gupta et al. |

(56) References Cited

U.S. PATENT DOCUMENTS

| | | |
|---|---|---|
| 6,374,185 B1 | 4/2002 | Taner et al. |
| 6,394,955 B1 | 5/2002 | Perlitz |
| 6,423,002 B1 | 7/2002 | Hossack |
| 6,436,046 B1 | 8/2002 | Napolitano et al. |
| 6,449,821 B1 | 9/2002 | Sudol et al. |
| 6,450,965 B2 | 9/2002 | Williams et al. |
| 6,468,216 B1 | 10/2002 | Powers et al. |
| 6,471,650 B2 | 10/2002 | Powers et al. |
| 6,475,150 B2 | 11/2002 | Haddad |
| 6,480,790 B1 | 11/2002 | Calvert et al. |
| 6,487,502 B1 | 11/2002 | Taner |
| 6,499,536 B1 | 12/2002 | Ellingsen |
| 6,503,204 B1 * | 1/2003 | Sumanaweera ........ B06B 1/0622 600/459 |
| 6,508,768 B1 | 1/2003 | Hall et al. |
| 6,508,770 B1 | 1/2003 | Cai |
| 6,517,484 B1 | 2/2003 | Wilk et al. |
| 6,526,163 B1 | 2/2003 | Halmann et al. |
| 6,543,272 B1 | 4/2003 | Vitek |
| 6,547,732 B2 | 4/2003 | Jago |
| 6,551,246 B1 | 4/2003 | Ustuner et al. |
| 6,565,510 B1 | 5/2003 | Haider |
| 6,582,367 B1 * | 6/2003 | Robinson .................. A61B 8/14 600/443 |
| 6,585,647 B1 | 7/2003 | Winder |
| 6,597,171 B2 | 7/2003 | Hurlimann et al. |
| 6,604,421 B1 | 8/2003 | Li |
| 6,614,560 B1 | 9/2003 | Silverbrook |
| 6,620,101 B2 | 9/2003 | Azzam et al. |
| 6,652,461 B1 | 11/2003 | Levkovitz |
| 6,668,654 B2 | 12/2003 | Dubois et al. |
| 6,672,165 B2 | 1/2004 | Rather et al. |
| 6,681,185 B1 | 1/2004 | Young et al. |
| 6,690,816 B2 | 2/2004 | Aylward et al. |
| 6,692,450 B1 | 2/2004 | Coleman |
| 6,695,778 B2 | 2/2004 | Golland et al. |
| 6,702,745 B1 | 3/2004 | Smythe |
| 6,704,692 B1 | 3/2004 | Banerjee et al. |
| 6,719,693 B2 | 4/2004 | Richard |
| 6,728,567 B2 | 4/2004 | Rather et al. |
| 6,752,762 B1 | 6/2004 | DeJong et al. |
| 6,755,787 B2 | 6/2004 | Hossack et al. |
| 6,780,152 B2 | 8/2004 | Ustuner et al. |
| 6,790,182 B2 | 9/2004 | Eck et al. |
| 6,835,178 B1 | 12/2004 | Wilson et al. |
| 6,837,853 B2 | 1/2005 | Marian |
| 6,843,770 B2 | 1/2005 | Sumanaweera |
| 6,847,737 B1 | 1/2005 | Kouri et al. |
| 6,854,332 B2 | 2/2005 | Alleyne |
| 6,865,140 B2 * | 3/2005 | Thomenius ........... B06B 1/0292 367/155 |
| 6,932,767 B2 | 8/2005 | Landry et al. |
| 7,033,320 B2 | 4/2006 | Von Behren et al. |
| 7,087,023 B2 | 8/2006 | Daft et al. |
| 7,104,956 B1 | 9/2006 | Christopher |
| 7,217,243 B2 | 5/2007 | Takeuchi |
| 7,221,867 B2 | 5/2007 | Silverbrook |
| 7,231,072 B2 | 6/2007 | Yamano et al. |
| 7,269,299 B2 | 9/2007 | Schroeder |
| 7,283,652 B2 | 10/2007 | Mendonca et al. |
| 7,285,094 B2 | 10/2007 | Nohara et al. |
| 7,293,462 B2 * | 11/2007 | Lee ......................... H04R 23/00 73/649 |
| 7,313,053 B2 | 12/2007 | Wodnicki |
| 7,366,704 B2 | 4/2008 | Reading et al. |
| 7,402,136 B2 | 7/2008 | Hossack et al. |
| 7,410,469 B1 | 8/2008 | Talish et al. |
| 7,415,880 B2 | 8/2008 | Renzel |
| 7,443,765 B2 | 10/2008 | Thomenius et al. |
| 7,444,875 B1 | 11/2008 | Wu et al. |
| 7,447,535 B2 | 11/2008 | Lavi |
| 7,448,998 B2 | 11/2008 | Robinson |
| 7,466,848 B2 | 12/2008 | Metaxas et al. |
| 7,469,096 B2 | 12/2008 | Silverbrook |
| 7,474,778 B2 | 1/2009 | Shinomura et al. |
| 7,481,577 B2 | 1/2009 | Ramamurthy et al. |
| 7,491,171 B2 | 2/2009 | Barthe et al. |
| 7,497,828 B1 | 3/2009 | Wilk et al. |
| 7,497,830 B2 | 3/2009 | Li |
| 7,510,529 B2 | 3/2009 | Chou et al. |
| 7,514,851 B2 | 4/2009 | Wilser et al. |
| 7,549,962 B2 | 6/2009 | Dreschel et al. |
| 7,574,026 B2 | 8/2009 | Rasche et al. |
| 7,625,343 B2 | 12/2009 | Cao et al. |
| 7,637,869 B2 | 12/2009 | Sudol |
| 7,668,583 B2 | 2/2010 | Fegert et al. |
| 7,674,228 B2 | 3/2010 | Williams et al. |
| 7,682,311 B2 | 3/2010 | Simopoulos et al. |
| 7,699,776 B2 | 4/2010 | Walker et al. |
| 7,722,541 B2 | 5/2010 | Cai |
| 7,744,532 B2 | 6/2010 | Ustuner et al. |
| 7,750,311 B2 | 7/2010 | Daghighian |
| 7,764,984 B2 | 7/2010 | Desmedt et al. |
| 7,785,260 B2 | 8/2010 | Umemura et al. |
| 7,787,680 B2 | 8/2010 | Ahn et al. |
| 7,806,828 B2 | 10/2010 | Stringer |
| 7,819,810 B2 | 10/2010 | Stringer et al. |
| 7,822,250 B2 | 10/2010 | Yao et al. |
| 7,824,337 B2 | 11/2010 | Abe et al. |
| 7,833,163 B2 | 11/2010 | Cai |
| 7,837,624 B1 | 11/2010 | Hossack et al. |
| 7,846,097 B2 | 12/2010 | Jones et al. |
| 7,850,613 B2 | 12/2010 | Stribling |
| 7,862,508 B2 | 1/2011 | Davies et al. |
| 7,876,945 B2 | 1/2011 | Lötjönen |
| 7,880,154 B2 | 2/2011 | Otto |
| 7,887,486 B2 | 2/2011 | Ustuner et al. |
| 7,901,358 B2 | 3/2011 | Mehi et al. |
| 7,914,451 B2 | 3/2011 | Davies |
| 7,919,906 B2 | 4/2011 | Cerofolini |
| 7,926,350 B2 | 4/2011 | Kröning et al. |
| 7,927,280 B2 | 4/2011 | Davidsen |
| 7,972,271 B2 | 7/2011 | Johnson et al. |
| 7,984,637 B2 | 7/2011 | Ao et al. |
| 7,984,651 B2 | 7/2011 | Randall et al. |
| 8,002,705 B1 | 8/2011 | Napolitano et al. |
| 8,007,439 B2 | 8/2011 | Specht |
| 8,057,392 B2 | 11/2011 | Hossack et al. |
| 8,057,393 B2 | 11/2011 | Yao et al. |
| 8,079,263 B2 | 12/2011 | Randall et al. |
| 8,079,956 B2 | 12/2011 | Azuma et al. |
| 8,088,067 B2 | 1/2012 | Vortman et al. |
| 8,088,068 B2 | 1/2012 | Yao et al. |
| 8,088,071 B2 | 1/2012 | Hwang et al. |
| 8,105,239 B2 | 1/2012 | Specht |
| 8,135,190 B2 | 3/2012 | Bae et al. |
| 8,157,737 B2 | 4/2012 | Zhang et al. |
| 8,182,427 B2 | 5/2012 | Wu et al. |
| 8,202,219 B2 | 6/2012 | Luo et al. |
| 8,265,175 B2 | 9/2012 | Barsoum et al. |
| 8,277,383 B2 | 10/2012 | Specht |
| 8,279,705 B2 | 10/2012 | Choi et al. |
| 8,412,307 B2 | 4/2013 | Willis et al. |
| 8,414,564 B2 | 4/2013 | Goldshleger et al. |
| 8,419,642 B2 | 4/2013 | Sandrin et al. |
| 8,473,239 B2 | 6/2013 | Specht et al. |
| 8,478,382 B2 | 7/2013 | Burnside et al. |
| 8,483,804 B2 | 7/2013 | Hsieh et al. |
| 8,532,951 B2 | 9/2013 | Roy et al. |
| 8,582,848 B2 | 11/2013 | Funka-Lea et al. |
| 8,602,993 B2 | 12/2013 | Specht et al. |
| 8,627,724 B2 | 1/2014 | Papadopoulos et al. |
| 8,634,615 B2 | 1/2014 | Brabec |
| 8,672,846 B2 | 3/2014 | Napolitano et al. |
| 8,684,936 B2 | 4/2014 | Specht |
| 9,036,887 B2 | 5/2015 | Fouras et al. |
| 9,072,495 B2 | 7/2015 | Specht |
| 9,146,313 B2 | 9/2015 | Specht et al. |
| 9,152,761 B2 | 10/2015 | Bhatia et al. |
| 9,176,078 B2 | 11/2015 | Flohr et al. |
| 9,192,355 B2 | 11/2015 | Specht et al. |
| 9,217,660 B2 | 12/2015 | Zlotnick et al. |
| 9,220,478 B2 | 12/2015 | Smith et al. |
| 9,247,874 B2 | 2/2016 | Kumar et al. |

(56) References Cited

U.S. PATENT DOCUMENTS

| | | |
|---|---|---|
| 9,247,926 B2 | 2/2016 | Smith et al. |
| 9,265,484 B2 | 2/2016 | Brewer et al. |
| 9,268,777 B2 | 2/2016 | Lu et al. |
| 9,271,661 B2 | 3/2016 | Moghari et al. |
| 9,277,861 B2 | 3/2016 | Kowal et al. |
| 9,282,945 B2 | 3/2016 | Smith et al. |
| 9,339,239 B2 | 5/2016 | Wang et al. |
| 9,339,256 B2 | 5/2016 | Specht et al. |
| 9,392,986 B2 | 7/2016 | Ning et al. |
| 9,420,994 B2 | 8/2016 | Specht |
| 9,510,806 B2 | 12/2016 | Smith et al. |
| 9,526,475 B2 | 12/2016 | Specht et al. |
| 9,526,485 B2 | 12/2016 | Yang |
| 9,572,549 B2 | 2/2017 | Belevich et al. |
| 9,576,354 B2 | 2/2017 | Fouras et al. |
| 9,582,876 B2 | 2/2017 | Specht |
| 9,606,206 B2 | 3/2017 | Boernert et al. |
| 9,659,152 B2 | 5/2017 | Mueller |
| 9,706,972 B1 | 7/2017 | Ahn et al. |
| 9,775,511 B2 | 10/2017 | Kumar et al. |
| 9,901,407 B2 | 2/2018 | Breisacher et al. |
| 10,342,518 B2 | 7/2019 | Specht et al. |
| 10,380,399 B2 | 8/2019 | Call et al. |
| 2002/0035864 A1 | 3/2002 | Paltieli et al. |
| 2002/0073781 A1* | 6/2002 | Hashimoto ........... B06B 1/0629 73/641 |
| 2002/0087071 A1 | 7/2002 | Schmitz et al. |
| 2002/0111568 A1 | 8/2002 | Bukshpan |
| 2002/0138003 A1 | 9/2002 | Bukshpan |
| 2002/0161299 A1 | 10/2002 | Prater et al. |
| 2003/0013962 A1 | 1/2003 | Bjaerum et al. |
| 2003/0028111 A1 | 2/2003 | Vaezy et al. |
| 2003/0040669 A1 | 2/2003 | Grass et al. |
| 2003/0220554 A1* | 11/2003 | Grenon ................... A61B 8/12 600/407 |
| 2003/0228053 A1 | 12/2003 | Li et al. |
| 2004/0015079 A1 | 1/2004 | Berger et al. |
| 2004/0054283 A1 | 3/2004 | Corey et al. |
| 2004/0068184 A1 | 4/2004 | Trahey et al. |
| 2004/0100163 A1 | 5/2004 | Baumgartner et al. |
| 2004/0111028 A1 | 6/2004 | Abe et al. |
| 2004/0122313 A1 | 6/2004 | Moore et al. |
| 2004/0122322 A1 | 6/2004 | Moore et al. |
| 2004/0127793 A1 | 7/2004 | Mendlein et al. |
| 2004/0138565 A1 | 7/2004 | Trucco |
| 2004/0144176 A1 | 7/2004 | Yoden |
| 2004/0215075 A1 | 10/2004 | Zagzebski et al. |
| 2004/0236217 A1 | 11/2004 | Cerwin et al. |
| 2004/0236223 A1 | 11/2004 | Barnes et al. |
| 2004/0267132 A1 | 12/2004 | Podany |
| 2005/0004449 A1 | 1/2005 | Mitschke et al. |
| 2005/0053305 A1 | 3/2005 | Li et al. |
| 2005/0054910 A1 | 3/2005 | Tremblay et al. |
| 2005/0061536 A1 | 3/2005 | Proulx |
| 2005/0090743 A1 | 4/2005 | Kawashima et al. |
| 2005/0090745 A1 | 4/2005 | Steen |
| 2005/0111846 A1 | 5/2005 | Steinbacher et al. |
| 2005/0113689 A1 | 5/2005 | Gritzky |
| 2005/0113694 A1 | 5/2005 | Haugen et al. |
| 2005/0124883 A1 | 6/2005 | Hunt |
| 2005/0131300 A1 | 6/2005 | Bakircioglu et al. |
| 2005/0147297 A1 | 7/2005 | McLaughlin et al. |
| 2005/0165312 A1 | 7/2005 | Knowles et al. |
| 2005/0203404 A1 | 9/2005 | Freiburger |
| 2005/0215883 A1 | 9/2005 | Hundley et al. |
| 2005/0240125 A1 | 10/2005 | Makin et al. |
| 2005/0252295 A1 | 11/2005 | Fink et al. |
| 2005/0281447 A1 | 12/2005 | Moreau-Gobard et al. |
| 2005/0288588 A1 | 12/2005 | Weber et al. |
| 2006/0058664 A1 | 3/2006 | Barthe et al. |
| 2006/0062447 A1 | 3/2006 | Rinck et al. |
| 2006/0074313 A1 | 4/2006 | Slayton et al. |
| 2006/0074315 A1 | 4/2006 | Liang et al. |
| 2006/0074320 A1 | 4/2006 | Yoo et al. |
| 2006/0079759 A1 | 4/2006 | Vaillant et al. |
| 2006/0079778 A1 | 4/2006 | Mo et al. |
| 2006/0079782 A1 | 4/2006 | Beach et al. |
| 2006/0094962 A1 | 5/2006 | Clark |
| 2006/0111634 A1 | 5/2006 | Wu |
| 2006/0122506 A1 | 6/2006 | Davies et al. |
| 2006/0173327 A1 | 8/2006 | Kim |
| 2006/0262961 A1 | 11/2006 | Noising et al. |
| 2006/0270934 A1 | 11/2006 | Savord et al. |
| 2007/0016022 A1 | 1/2007 | Blalock et al. |
| 2007/0016044 A1 | 1/2007 | Blalock et al. |
| 2007/0036414 A1 | 2/2007 | Georgescu et al. |
| 2007/0055155 A1 | 3/2007 | Owen et al. |
| 2007/0073781 A1 | 3/2007 | Adkins et al. |
| 2007/0078345 A1 | 4/2007 | Mo et al. |
| 2007/0088213 A1 | 4/2007 | Poland |
| 2007/0138157 A1 | 6/2007 | Dane et al. |
| 2007/0161898 A1 | 7/2007 | Hao et al. |
| 2007/0161904 A1 | 7/2007 | Urbano |
| 2007/0167752 A1 | 7/2007 | Proulx et al. |
| 2007/0167824 A1 | 7/2007 | Lee et al. |
| 2007/0232914 A1 | 10/2007 | Chen et al. |
| 2007/0238985 A1 | 10/2007 | Smith et al. |
| 2007/0242567 A1 | 10/2007 | Daft et al. |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0125659 A1 | 5/2008 | Wilser et al. |
| 2008/0181479 A1 | 7/2008 | Yang et al. |
| 2008/0183075 A1 | 7/2008 | Govari et al. |
| 2008/0188747 A1 | 8/2008 | Randall et al. |
| 2008/0188750 A1 | 8/2008 | Randall et al. |
| 2008/0194957 A1 | 8/2008 | Hoctor et al. |
| 2008/0194958 A1 | 8/2008 | Lee et al. |
| 2008/0194959 A1 | 8/2008 | Wang et al. |
| 2008/0208061 A1 | 8/2008 | Halmann |
| 2008/0242996 A1 | 10/2008 | Hall et al. |
| 2008/0249408 A1 | 10/2008 | Palmeri et al. |
| 2008/0255452 A1 | 10/2008 | Entrekin |
| 2008/0269604 A1 | 10/2008 | Boctor et al. |
| 2008/0269613 A1 | 10/2008 | Summers et al. |
| 2008/0275344 A1 | 11/2008 | Glide-Hurst et al. |
| 2008/0285819 A1 | 11/2008 | Konofagou et al. |
| 2008/0287787 A1 | 11/2008 | Sauer et al. |
| 2008/0294045 A1 | 11/2008 | Ellington et al. |
| 2008/0294050 A1 | 11/2008 | Shinomura et al. |
| 2008/0294052 A1 | 11/2008 | Wilser et al. |
| 2008/0306382 A1 | 12/2008 | Guracar et al. |
| 2008/0306386 A1 | 12/2008 | Baba et al. |
| 2008/0319317 A1 | 12/2008 | Kamiyama et al. |
| 2009/0010459 A1 | 1/2009 | Garbini et al. |
| 2009/0012393 A1 | 1/2009 | Choi |
| 2009/0015665 A1 | 1/2009 | Willsie |
| 2009/0016163 A1 | 1/2009 | Freeman et al. |
| 2009/0018445 A1 | 1/2009 | Schers et al. |
| 2009/0024039 A1 | 1/2009 | Wang et al. |
| 2009/0036780 A1 | 2/2009 | Abraham |
| 2009/0043206 A1 | 2/2009 | Towfiq et al. |
| 2009/0048519 A1 | 2/2009 | Hossack et al. |
| 2009/0069681 A1 | 3/2009 | Lundberg et al. |
| 2009/0069686 A1 | 3/2009 | Daft et al. |
| 2009/0069692 A1 | 3/2009 | Cooley et al. |
| 2009/0079299 A1 | 3/2009 | Bradley et al. |
| 2009/0099483 A1 | 4/2009 | Rybyanets |
| 2009/0112095 A1 | 4/2009 | Daigle |
| 2009/0131797 A1 | 5/2009 | Jeong et al. |
| 2009/0143680 A1 | 6/2009 | Yao et al. |
| 2009/0148012 A1 | 6/2009 | Altmann et al. |
| 2009/0150094 A1 | 6/2009 | Van Velsor et al. |

(56) References Cited

U.S. PATENT DOCUMENTS

| | | |
|---|---|---|
| 2009/0182233 A1 | 7/2009 | Wodnicki |
| 2009/0182237 A1* | 7/2009 | Angelsen .......... B06B 1/064 600/459 |
| 2009/0198134 A1 | 8/2009 | Hashimoto et al. |
| 2009/0203997 A1 | 8/2009 | Ustuner |
| 2009/0208080 A1 | 8/2009 | Grau et al. |
| 2009/0259128 A1 | 10/2009 | Stribling |
| 2009/0264760 A1 | 10/2009 | Lazebnik et al. |
| 2009/0306510 A1 | 12/2009 | Hashiba et al. |
| 2009/0326379 A1 | 12/2009 | Daigle et al. |
| 2010/0010354 A1 | 1/2010 | Skerl et al. |
| 2010/0016725 A1 | 1/2010 | Thiele |
| 2010/0036258 A1 | 2/2010 | Dietz et al. |
| 2010/0063397 A1 | 3/2010 | Wagner |
| 2010/0063399 A1 | 3/2010 | Walker et al. |
| 2010/0069751 A1 | 3/2010 | Hazard et al. |
| 2010/0069756 A1 | 3/2010 | Ogasawara et al. |
| 2010/0085383 A1 | 4/2010 | Cohen et al. |
| 2010/0106431 A1 | 4/2010 | Baba et al. |
| 2010/0109481 A1 | 5/2010 | Buccafusca |
| 2010/0121193 A1 | 5/2010 | Fukukita et al. |
| 2010/0121196 A1 | 5/2010 | Hwang et al. |
| 2010/0130855 A1 | 5/2010 | Lundberg et al. |
| 2010/0145195 A1 | 6/2010 | Hyun |
| 2010/0168566 A1 | 7/2010 | Bercoff et al. |
| 2010/0168578 A1 | 7/2010 | Garson, Jr. et al. |
| 2010/0174194 A1 | 7/2010 | Chiang et al. |
| 2010/0174198 A1 | 7/2010 | Young et al. |
| 2010/0191110 A1 | 7/2010 | Insana et al. |
| 2010/0217124 A1 | 8/2010 | Cooley |
| 2010/0228126 A1 | 9/2010 | Emery et al. |
| 2010/0240994 A1 | 9/2010 | Zheng |
| 2010/0249570 A1 | 9/2010 | Carson et al. |
| 2010/0249596 A1 | 9/2010 | Magee |
| 2010/0256488 A1 | 10/2010 | Kim et al. |
| 2010/0262013 A1 | 10/2010 | Smith et al. |
| 2010/0266176 A1 | 10/2010 | Masumoto et al. |
| 2010/0286525 A1 | 11/2010 | Osumi |
| 2010/0286527 A1 | 11/2010 | Cannon et al. |
| 2010/0310143 A1 | 12/2010 | Rao et al. |
| 2010/0317971 A1 | 12/2010 | Fan et al. |
| 2010/0324418 A1 | 12/2010 | El-Aklouk et al. |
| 2010/0324423 A1 | 12/2010 | El-Aklouk et al. |
| 2010/0329521 A1 | 12/2010 | Beymer et al. |
| 2011/0005322 A1 | 1/2011 | Ustuner |
| 2011/0016977 A1 | 1/2011 | Guracar |
| 2011/0021920 A1 | 1/2011 | Shafir et al. |
| 2011/0021923 A1 | 1/2011 | Daft et al. |
| 2011/0033098 A1 | 2/2011 | Richter et al. |
| 2011/0044133 A1 | 2/2011 | Tokita |
| 2011/0066030 A1 | 3/2011 | Yao |
| 2011/0098565 A1 | 4/2011 | Masuzawa |
| 2011/0112400 A1 | 5/2011 | Emery et al. |
| 2011/0112404 A1 | 5/2011 | Gourevitch |
| 2011/0125017 A1 | 5/2011 | Ramamurthy et al. |
| 2011/0178441 A1 | 7/2011 | Tyler |
| 2011/0270088 A1 | 11/2011 | Shiina |
| 2011/0301470 A1 | 12/2011 | Sato et al. |
| 2011/0306886 A1 | 12/2011 | Daft et al. |
| 2011/0319764 A1 | 12/2011 | Okada et al. |
| 2012/0004545 A1 | 1/2012 | Ziv-Ari et al. |
| 2012/0035482 A1 | 2/2012 | Kim et al. |
| 2012/0036934 A1 | 2/2012 | Kröning et al. |
| 2012/0085173 A1 | 4/2012 | Papadopoulos et al. |
| 2012/0095347 A1 | 4/2012 | Adam et al. |
| 2012/0101378 A1 | 4/2012 | Lee |
| 2012/0114210 A1 | 5/2012 | Kim et al. |
| 2012/0121150 A1 | 5/2012 | Murashita |
| 2012/0137778 A1 | 6/2012 | Kitazawa et al. |
| 2012/0140595 A1 | 6/2012 | Amemiya |
| 2012/0141002 A1 | 6/2012 | Urbano et al. |
| 2012/0165670 A1 | 6/2012 | Shi et al. |
| 2012/0179044 A1 | 7/2012 | Chiang et al. |
| 2012/0226201 A1 | 9/2012 | Clark et al. |
| 2012/0235998 A1 | 9/2012 | Smith-Casem et al. |
| 2012/0243763 A1 | 9/2012 | Wen et al. |
| 2012/0253194 A1 | 10/2012 | Tamura |
| 2012/0265075 A1 | 10/2012 | Pedrizzetti et al. |
| 2012/0277585 A1 | 11/2012 | Koenig et al. |
| 2013/0070062 A1 | 3/2013 | Fouras et al. |
| 2013/0076207 A1 | 3/2013 | Krohn et al. |
| 2013/0079639 A1 | 3/2013 | Hoctor et al. |
| 2013/0083628 A1 | 4/2013 | Qiao et al. |
| 2013/0088122 A1 | 4/2013 | Krohn et al. |
| 2013/0116561 A1 | 5/2013 | Rothberg et al. |
| 2013/0128702 A1* | 5/2013 | Degertekin .......... G01S 15/89 367/140 |
| 2013/0131516 A1 | 5/2013 | Katsuyama |
| 2013/0144165 A1 | 6/2013 | Ebbini et al. |
| 2013/0144166 A1 | 6/2013 | Specht et al. |
| 2013/0204136 A1 | 8/2013 | Duric et al. |
| 2013/0204137 A1 | 8/2013 | Roy et al. |
| 2013/0253325 A1 | 9/2013 | Call et al. |
| 2013/0258805 A1 | 10/2013 | Hansen et al. |
| 2013/0261463 A1 | 10/2013 | Chiang et al. |
| 2014/0058266 A1 | 2/2014 | Call et al. |
| 2014/0073921 A1 | 3/2014 | Specht et al. |
| 2014/0086014 A1 | 3/2014 | Kobayashi |
| 2014/0147013 A1 | 5/2014 | Shandas et al. |
| 2014/0243673 A1 | 8/2014 | Anand et al. |
| 2015/0045668 A1 | 2/2015 | Smith et al. |
| 2015/0080727 A1 | 3/2015 | Specht et al. |
| 2015/0172878 A1 | 6/2015 | Luna et al. |
| 2015/0224346 A1* | 8/2015 | Coviello .......... G01S 7/52047 600/439 |
| 2016/0095579 A1 | 4/2016 | Smith et al. |
| 2016/0135783 A1 | 5/2016 | Brewer et al. |
| 2016/0157833 A1 | 6/2016 | Smith et al. |
| 2016/0256134 A1 | 9/2016 | Specht et al. |
| 2016/0354059 A1 | 12/2016 | Specht |
| 2017/0074982 A1 | 3/2017 | Smith et al. |
| 2017/0079621 A1 | 3/2017 | Specht et al. |
| 2017/0119352 A1 | 5/2017 | Anand et al. |
| 2018/0049717 A1 | 2/2018 | Adam et al. |
| 2018/0153511 A1 | 6/2018 | Specht et al. |
| 2018/0279991 A1 | 10/2018 | Call et al. |
| 2019/0008487 A1 | 1/2019 | Belevich et al. |
| 2019/0021697 A1 | 1/2019 | Specht et al. |
| 2019/0083058 A1 | 3/2019 | Specht |
| 2019/0175152 A1 | 6/2019 | Smith et al. |
| 2019/0200961 A1 | 7/2019 | Specht et al. |
| 2019/0328367 A1 | 10/2019 | Specht et al. |
| 2019/0370522 A1 | 12/2019 | Call et al. |

FOREIGN PATENT DOCUMENTS

| | | |
|---|---|---|
| CN | 101103927 A | 1/2008 |
| CN | 101116622 A | 2/2008 |
| CN | 101190134 A | 6/2008 |
| CN | 101453955 A | 6/2009 |
| CN | 100545650 C | 9/2009 |
| CN | 101609150 A | 12/2009 |
| CN | 101843501 A | 9/2010 |
| CN | 101912278 A | 12/2010 |
| CN | 102018533 A | 4/2011 |
| CN | 102112047 A | 6/2011 |
| CN | 102123668 A | 7/2011 |
| CN | 102599930 A | 7/2012 |
| DE | 102011114333 A1 | 3/2013 |
| EP | 1949856 A1 | 7/2008 |
| EP | 2058796 A2 | 5/2009 |
| EP | 2101191 A2 | 9/2009 |
| EP | 2182352 A2 | 5/2010 |
| EP | 2187813 A1 | 5/2010 |
| EP | 2198785 A1 | 6/2010 |
| EP | 1757955 B1 | 11/2010 |
| EP | 2325672 A1 | 5/2011 |
| EP | 1462819 B1 | 7/2011 |
| EP | 2356941 A1 | 8/2011 |
| EP | 1979739 B1 | 10/2011 |
| EP | 2385391 A2 | 11/2011 |
| EP | 2294400 B1 | 2/2012 |
| EP | 2453256 A2 | 5/2012 |
| EP | 1840594 B1 | 6/2012 |

(56) References Cited

FOREIGN PATENT DOCUMENTS

| | | |
|---|---|---|
| EP | 2514368 A1 | 10/2012 |
| EP | 1850743 B1 | 12/2012 |
| EP | 1594404 B1 | 9/2013 |
| EP | 2026280 B1 | 10/2013 |
| FR | 2851662 A1 | 8/2004 |
| JP | 49-11189 A | 1/1974 |
| JP | 54-44375 A | 4/1979 |
| JP | S55103839 A | 8/1980 |
| JP | 57-31848 A | 2/1982 |
| JP | 58-223059 A | 12/1983 |
| JP | 59-101143 A | 6/1984 |
| JP | 59-174151 A | 10/1984 |
| JP | 60-13109 U | 1/1985 |
| JP | 60-68836 A | 4/1985 |
| JP | 01164354 A | 6/1989 |
| JP | 02501431 A | 5/1990 |
| JP | 03015455 A | 1/1991 |
| JP | 03126443 A | 5/1991 |
| JP | 04017842 A | 1/1992 |
| JP | 04067856 A | 3/1992 |
| JP | 05042138 A | 2/1993 |
| JP | 06125908 A | 5/1994 |
| JP | 06254092 A | 9/1994 |
| JP | 07051266 A | 2/1995 |
| JP | 070204201 A | 8/1995 |
| JP | 08154930 A | 6/1996 |
| JP | 08252253 A | 10/1996 |
| JP | 09103429 A | 4/1997 |
| JP | 09201361 A | 8/1997 |
| JP | 2777197 B | 5/1998 |
| JP | 10216128 A | 8/1998 |
| JP | 11089833 A | 4/1999 |
| JP | 11239578 A | 9/1999 |
| JP | 2001507794 A | 6/2001 |
| JP | 2001245884 A | 9/2001 |
| JP | 2002209894 A | 7/2002 |
| JP | 2002253548 A | 9/2002 |
| JP | 2002253549 A | 9/2002 |
| JP | 2003235839 A | 8/2003 |
| JP | 2004167092 A | 6/2004 |
| JP | 2004215987 A | 8/2004 |
| JP | 2004337457 A | 12/2004 |
| JP | 2004340809 A | 12/2004 |
| JP | 2004351214 A | 12/2004 |
| JP | 2005046192 A | 2/2005 |
| JP | 2005152187 A | 6/2005 |
| JP | 2005523792 A | 8/2005 |
| JP | 2005526539 A | 9/2005 |
| JP | 2006051356 A | 2/2006 |
| JP | 200661203 A | 3/2006 |
| JP | 2006122657 A | 5/2006 |
| JP | 2006130313 A | 5/2006 |
| JP | 2006204923 A | 8/2006 |
| JP | 2007325937 A | 12/2007 |
| JP | 2008122209 A | 5/2008 |
| JP | 2008513763 A | 5/2008 |
| JP | 2008515557 A | 5/2008 |
| JP | 2008132342 A | 6/2008 |
| JP | 2008522642 A | 7/2008 |
| JP | 2008259541 A | 10/2008 |
| JP | 2008279274 A | 11/2008 |
| JP | 2008307087 A | 12/2008 |
| JP | 2009240667 A | 10/2009 |
| JP | 2010-5375 A | 1/2010 |
| JP | 2010124842 A | 6/2010 |
| JP | 2010526626 A | 8/2010 |
| JP | 2011529362 A | 12/2011 |
| JP | 2013121493 A | 6/2013 |
| JP | 2014087448 A | 5/2014 |
| KR | 100715132 B | 4/2007 |
| KR | 1020080044737 A | 5/2008 |
| KR | 1020090103408 A | 10/2009 |
| WO | WO92/18054 A1 | 10/1992 |
| WO | WO98/00719 A2 | 1/1998 |
| WO | WO01/64109 A1 | 9/2001 |
| WO | WO02/08459 A2 | 10/2002 |
| WO | WO2005/009245 A1 | 2/2005 |
| WO | WO2006/114735 A1 | 11/2006 |
| WO | WO2007/127147 A2 | 11/2007 |
| WO | WO2008/097479 A1 | 8/2008 |
| WO | WO2009/060182 A2 | 5/2009 |
| WO | WO2010/095094 A1 | 8/2010 |
| WO | WO2010/137453 A1 | 12/2010 |
| WO | WO2010/139519 A1 | 12/2010 |
| WO | WO2011/004661 A1 | 1/2011 |
| WO | WO2011/057252 A1 | 5/2011 |
| WO | WO2011/064688 A1 | 6/2011 |
| WO | WO2011/100697 A1 | 8/2011 |
| WO | WO2011/123529 A1 | 10/2011 |
| WO | WO2012/028896 A1 | 3/2012 |
| WO | WO2012/049124 A2 | 4/2012 |
| WO | WO2012/049612 A2 | 4/2012 |
| WO | WO2012/078639 A1 | 6/2012 |
| WO | WO2012/091280 A1 | 7/2012 |
| WO | WO2012/112540 A2 | 8/2012 |
| WO | WO2012/131340 A2 | 10/2012 |
| WO | WO2012/160541 A2 | 11/2012 |
| WO | WO2013/059358 A2 | 4/2013 |
| WO | WO2013/109965 A1 | 7/2013 |
| WO | WO2013/116807 A1 | 8/2013 |
| WO | WO2013/116809 A1 | 8/2013 |
| WO | WO2013/116851 A1 | 8/2013 |
| WO | WO2013/116854 A1 | 8/2013 |
| WO | WO2013/116866 A1 | 8/2013 |
| WO | WO2013/128301 A2 | 9/2013 |

OTHER PUBLICATIONS

Abeysekera et al.; Alignment and calibration of dual ultrasound transducers using a wedge phantom; Ultrasound in Medicine and Biology; 37(2); pp. 271-279; Feb. 2011.

Arigovindan et al.; Full motion and flow field recovery from echo doppler data; IEEE Transactions on Medical Imaging; 26(1); pp. 31-45; Jan. 2007.

Capineri et al.; A doppler system for dynamic vector velocity maps; Ultrasound in Medicine & Biology; 28(2); pp. 237-248; Feb. 28, 2002.

Carson et al.; Measurement of photoacoustic transducer position by robotic source placement and nonlinear parameter estimation; Biomedical Optics (BiOS); International Society for Optics and Photonics (9th Conf. on Biomedical Thermoacoustics, Optoacoustics, and Acousto-optics; vol. 6856; 9 pages; Feb. 28, 2008.

Chen et al.; Maximum-likelihood source localization and unknown sensor location estimation for wideband signals in the near-field; IEEE Transactions on Signal Processing; 50(8); pp. 1843-1854; Aug. 2002.

Chen et al.; Source localization and tracking of a wideband source using a randomly distributed beamforming sensor array; International Journal of High Performance Computing Applications; 16(3); pp. 259-272; Fall 2002.

Cristianini et al.; An Introduction to Support Vector Machines; Cambridge University Press; pp. 93-111; Mar. 2000.

Dunmire et al.; A brief history of vector doppler; Medical Imaging 2001; International Society for Optics and Photonics; pp. 200-214; May 30, 2001.

Du et al.; User parameter free approaches to multistatic adaptive ultrasound imaging; 5th IEEE International Symposium; pp. 1287-1290, May 2008.

Feigenbaum, Harvey, M.D.; Echocardiography; Lippincott Williams & Wilkins; Philadelphia; 5th Ed.; pp. 482, 484; Feb. 1994.

Fernandez et al.; High resolution ultrasound beamforming using synthetic and adaptive imaging techniques; Proceedings IEEE International Symposium on Biomedical Imaging; Washington, D.C.; pp. 433-436; Jul. 7-10, 2002.

Gazor et al.; Wideband multi-source beamforming with array location calibration and direction finding; Conference on Acoustics, Speech and Signal Processing ICASSP-95; Detroit, MI; vol. 3 IEEE; pp. 1904-1907; May 9-12, 1995.

(56) References Cited

OTHER PUBLICATIONS

Haykin, Simon; Neural Networks: A Comprehensive Foundation (2nd Ed.); Prentice Hall; pp. 156-187; Jul. 16, 1998.

Heikkila et al.; A four-step camera calibration procedure with implicit image correction; Proceedings IEEE Computer Scociety Conference on Computer Vision and Pattern Recognition; San Juan; pp. 1106-1112; Jun. 17-19, 1997.

Hendee et al.; Medical Imaging Physics; Wiley-Liss, Inc. 4th Edition; Chap. 19-22; pp. 303-353; (year of pub. sufficiently earlier than effective US filed and any foreign priority date) © 2002.

Hsu et al.; Real-time freehand 3D ultrasound calibration; CUED/F-INFENG/TR 565; Department of Engineering, University of Cambridge, United Kingdom; 14 pages; Sep. 2006.

Jeffs; Beamforming: a brief introduction; Brigham Young University; 14 pages; retrieved from the internet (http://ens.ewi.tudelft.nl/Education/courses/et4235/Beamforming.pdf); Oct. 2004.

Khamene et al.; A novel phantom-less spatial and temporal ultrasound calibration method; Medical Image Computing and Computer-Assisted Intervention—MICCAI (Proceedings 8th Int. Conf.); Springer Berlin Heidelberg; Palm Springs, CA; pp. 65-72; Oct. 26-29, 2005.

Kramb et al,.; Considerations for using phased array ultrasonics in a fully automated inspection system. Review of Quantitative Nondestructive Evaluation, 2004 Edition, ed. D. O. Thompson and D. E. Chimenti, American Inst. of Physics, pp. 817-825, Mar. 2004.

Ledesma-Carbayo et al.; Spatio-temporal nonrigid registration for ultrasound cardiac motion estimation; IEEE Trans. On Medical Imaging; vol. 24; No. 9; Sep. 2005.

Leotta et al.; Quantitative three-dimensional echocardiography by rapid imaging . . . ; J American Society of Echocardiography; vol. 10; No. 8; ppl 830-839; Oct. 1997.

Li et al.; An efficient speckle tracking algorithm for ultrasonic imaging; 24; pp. 215-228; Oct. 1, 2002.

Morrison et al.; A probabilistic neural network based image segmentation network for magnetic resonance images; Proc. Conf. Neural Networks; Baltimore, MD; vol. 3; pp. 60-65; Jun. 1992.

Nadkarni et al.; Cardiac motion synchronization for 3D cardiac ultrasound imaging; Ph.D. Dissertation, University of Western Ontario; Jun. 2002.

Opretzka et al.; A high-frequency ultrasound imaging system combining limited-angle spatial compounding and model-based synthetic aperture focusing; IEEE Transactions on Ultrasonics, Ferroelectrics and Frequency Control, IEEE, US; 58(7); pp. 1355-1365; Jul. 2, 2011.

Press et al.; Cubic spline interpolation; §3.3 in "Numerical Recipes in FORTRAN: The Art of Scientific Computing", 2nd Ed.; Cambridge, England; Cambridge University Press; pp. 107-110; Sep. 1992.

Saad et al.; Computer vision approach for ultrasound doppler angle estimation; Journal of Digital Imaging; 22(6); pp. 681-688; Dec. 1, 2009.

Sakas et al.; Preprocessing and volume rendering of 3D ultrasonic data; IEEE Computer Graphics and Applications; pp. 47-54, Jul. 1995.

Sapia et al.; Deconvolution of ultrasonic waveforms using an adaptive wiener filter; Review of Progress in Quantitative Nondestructive Evaluation; vol. 13A; Plenum Press; pp. 855-862; Jan. 1994.

Sapia et al.; Ultrasound image deconvolution using adaptive inverse filtering; 12 IEEE Symposium on Computer-Based Medical Systems, CBMS, pp. 248-253; Jun. 1999.

Sapia, Mark Angelo; Multi-dimensional deconvolution of optical microscope and ultrasound imaging using adaptive least-mean-square (LMs) inverse filtering; Ph.D. Dissertation; University of Connecticut; Jan. 2000.

Slavine et al.; Construction, calibration and evaluation of a tissue phantom with reproducible optical properties for investigations in light emission tomography; Engineering in Medicine and Biology Workshop; Dallas, TX; IEEE pp. 122-125; Nov. 11-12, 2007.

Smith et al.; High-speed ultrasound volumetric imaging system. 1. Transducer design and beam steering; IEEE Trans. Ultrason., Ferroelect., Freq. Contr.; vol. 38; pp. 100-108; Mar. 1991.

Specht et al.; Deconvolution techniques for digital longitudinal tomography; SPIE; vol. 454; presented at Application of Optical Instrumentation in Medicine XII; pp. 319-325; Jun. 1984.

Specht et al.; Experience with adaptive PNN and adaptive GRNN; Proc. IEEE International Joint Conf. on Neural Networks; vol. 2; pp. 1203-1208; Orlando, FL; Jun. 1994.

Specht, D.F.; A general regression neural network; IEEE Trans. On Neural Networks; vol. 2.; No. 6; Nov. 1991.

Specht, D.F.; Blind deconvolution of motion blur using LMS inverse filtering; Lockheed Independent Research (unpublished); Jun. 23, 1975.

Specht, D.F.; Enhancements to probabilistic neural networks; Proc. IEEE International Joint Conf. on Neural Networks; Baltimore, MD; Jun. 1992.

Specht, D.F.; GRNN with double clustering; Proc. IEEE International Joint Conf. Neural Networks; Vancouver, Canada; Jul. 16-21, 2006.

Specht, D.F.; Probabilistic neural networks; Pergamon Press; Neural Networks; vol. 3; pp. 109-118; Feb. 1990.

UCLA Academic Technology; SPSS learning module: How can I analyze a subset of my data; 6 pages; retrieved from the internet (http://www.ats.ucla.edu/stat/spss/modules/subset_analyze.htm) Nov. 26, 2001.

Urban et al; Implementation of vibro-acoustography on a clinical ultrasound system; IEEE Transactions on Ultrasonics, Ferroelectrics, and Frequency Control; 58(6); pp. 1169-1181 (Author Manuscript, 25 pgs.); Jun. 2011.

Urban et al; Implementation of vibro-acoustography on a clinical ultrasound system; IEEE Ultrasonics Symposium (IUS); pp. 326-329; Oct. 14, 2010.

Von Ramm et al.; High-speed ultrasound volumetric imaging-System. 2. Parallel processing and image display; IEEE Trans. Ultrason., Ferroelect., Freq. Contr.; vol. 38; pp. 109-115; Mar. 1991.

Wang et al.; Photoacoustic tomography of biological tissues with high cross-section resolution: reconstruction and experiment; Medical Physics; 29(12); pp. 2799-2805; Dec. 2002.

Wells, P.N.T.; Biomedical ultrasonics; Academic Press; London, New York, San Francisco; pp. 124-125; Mar. 1977.

Widrow et al.; Adaptive signal processing; Prentice-Hall; Englewood Cliffs, NJ; pp. 99-116; Mar. 1985.

Wikipedia; Point cloud; 2 pages; retrieved Nov. 24, 2014 from the internet (https://en.wikipedia.org/w/index.php?title=Point_cloud&oldid=472583138).

Wikipedia; Curve fitting; 5 pages; retrieved from the internet (http:en.wikipedia.org/wiki/Curve_fitting) Dec. 19, 2010.

Wikipedia; Speed of sound; 17 pages; retrieved from the internet (http:en.wikipedia.org/wiki/Speed_of_sound) Feb. 15, 2011.

Yang et al.; Time-of-arrival calibration for improving the microwave breast cancer imaging; 2011 IEEE Topical Conf. on Biomedical Wireless Technologies, Networks, and sensing Systems (BioWireleSS); Phoenix, AZ; pp. 67-70; Jan. 16-19, 2011.

Zang et al.; A high-frequency high frame rate duplex ultrasound linear array imaging system for small animal imaging; IEEE transactions on ultrasound, ferroelectrics, and frequency control; 57(7); pp. 1548-1567; Jul. 2010.

Belevich et al.; U.S. Appl. No. 15/400,826 entitled "Calibration of multiple aperture ultrasound probes," filed Jan. 6, 2017.

Call et al.; U.S. Appl. No. 15/500,933 entitled "Network-based ultrasound imaging system," filed Feb. 1, 2017.

* cited by examiner

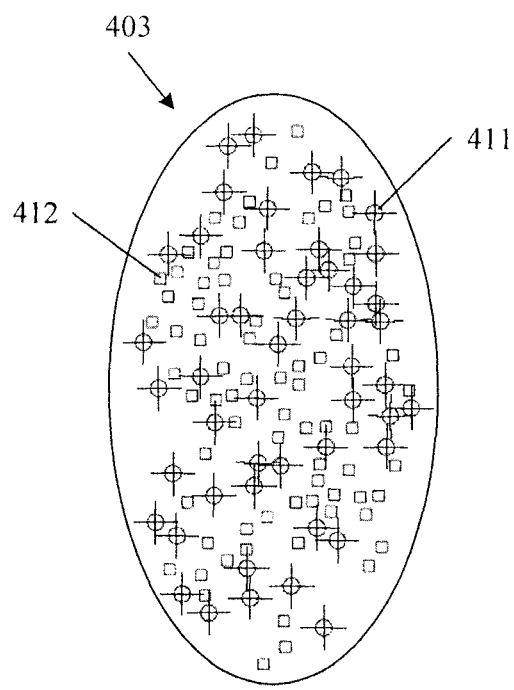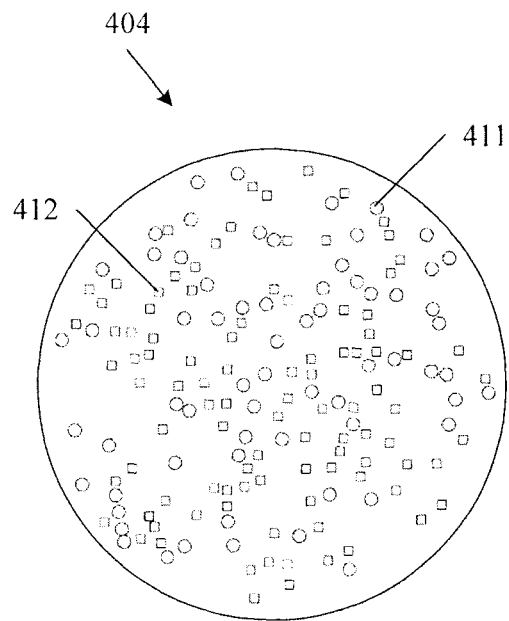
Fig. 5          Fig. 6
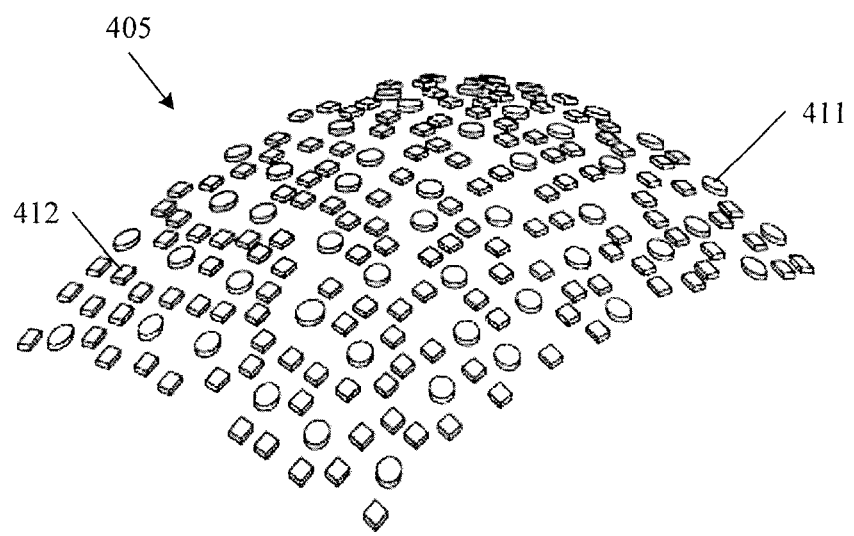
Fig. 7

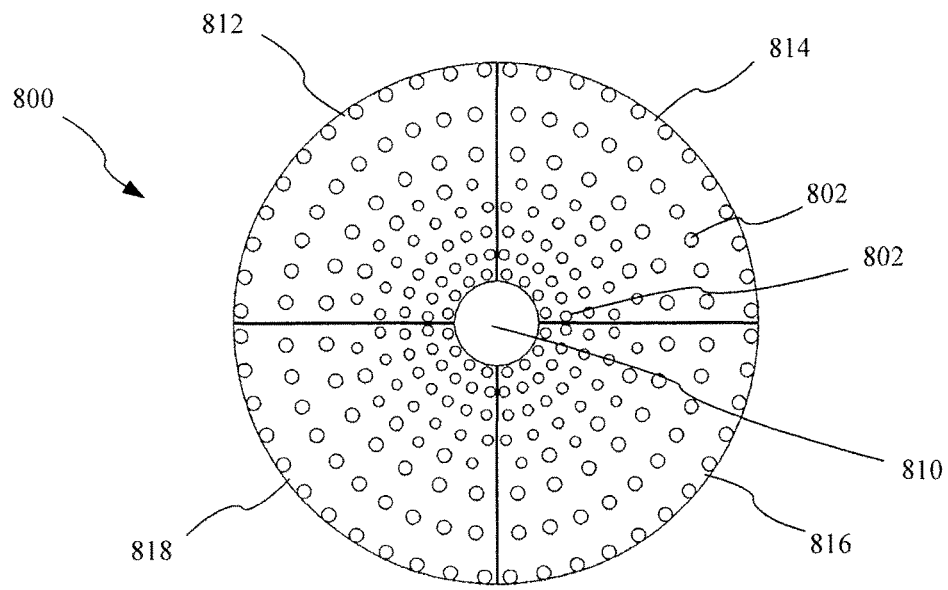
Fig. 15
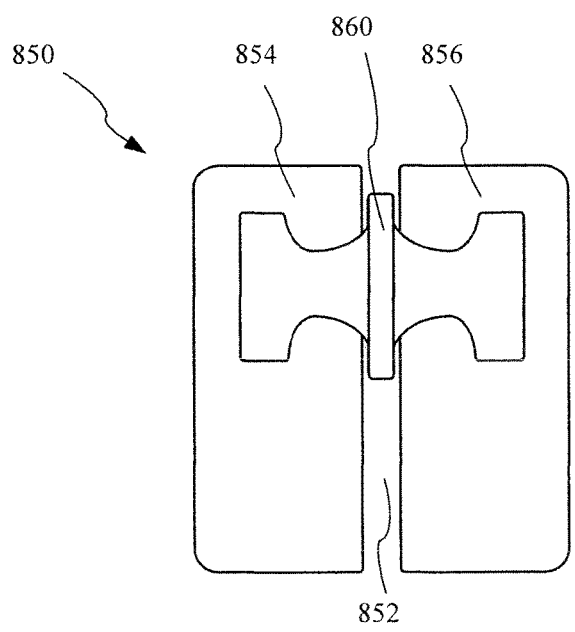 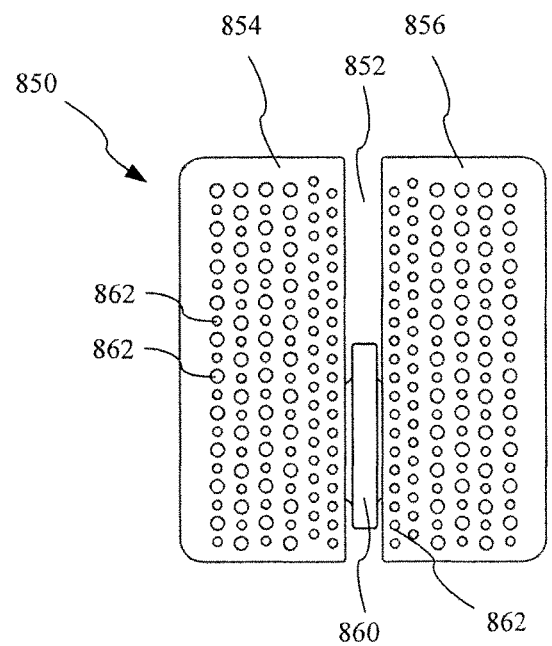
Fig. 16A            Fig. 16B

ULTRASOUND IMAGING WITH SPARSE ARRAY PROBES

CROSS-REFERENCE TO RELATED APPLICATIONS

This application claims the benefit of U.S. Provisional Patent Application No. 62/287,694, filed on Jan. 27, 2016, titled "Ultrasound Imaging Using Apparent Point-Source Transmit Transducer", and U.S. Provisional Patent Application No. 62/310,482, filed on Mar. 18, 2016, titled "Real-Time Three-Dimensional Ultrasound Imaging" both of which are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This application relates generally to the field of ultrasound imaging, and more particularly to ping-based ultrasound imaging using sparse arrays of ultrasound transducer elements.

BACKGROUND

In conventional scanline-based ultrasonic imaging, a focused beam of ultrasound energy is transmitted into body tissues to be examined and echoes returned along the same line are detected and plotted to form a portion of an image along the scanline. A complete image may be formed by repeating the process and combining image portions along a series of scanlines within a scan plane. Any information in between successive scanlines must be estimated by interpolation.

The same process has been extended to obtaining ultrasonic images of three-dimensional volumes by combining images from multiple adjacent slices (where each slice is in a different scan plane). Again, any information from any space in between successive scan planes must be estimated by interpolation. Because time elapses between capturing complete 2D (two-dimensional) slices, obtaining 3D (three-dimensional) image data for a moving object may be significantly impaired. So-called "4D" (four-dimensional) imaging systems (in which the fourth dimension is time) strive to produce moving images (i.e., video) of 3D volumetric space. Scanline-based imaging systems also have an inherent frame-rate limitation which creates difficulties when attempting 4D imaging on a moving object.

As a result of these and other factors, some of the limitations of existing 2D and 3D ultrasonic imaging systems and methods include poor temporal and spatial resolution, imaging depth, speckle noise, poor lateral resolution, obscured tissues and other such problems.

Significant improvements have been made in the field of ultrasound imaging with the creation of multiple aperture imaging, examples of which are shown and described in Applicant's prior patents and applications referenced above. Multiple aperture imaging methods and systems allow for ultrasound signals to be both transmitted and received from physically and logically separate apertures.

SUMMARY OF THE DISCLOSURE

The various embodiments of systems and methods herein provide the ability to perform high resolution three-dimensional ultrasound imaging at frame rates sufficient to capture details of moving objects. Traditional scanline-based ultrasound imaging methods are limited to relatively slow frame rates due to the need to transmit and receive many scanlines to obtain a single two-dimensional plane. Extending such techniques to obtain imaging data from a complete 3D volume results in even slower frame rates due to the need to image many 2D slices.

As an example, assume that one needs to collect data from a cube of tissue 10 cm on a side at a depth ranging from 5 cm to 15 cm. If scanlines are transmitted from a common center, the shape that would be explored would be a truncated pyramid instead of a shape with comparable thickness in the proximal and distal regions. The tissue may be sampled with beams that are 2 mm (or less) apart on the distal face of the cube. To cover the distal surface one would need at least 50×50 directed beams or 2500 directed pulses. With a maximum pulse rate of approximately 2500 pulses/sec (which may be constrained by the speed of sound in tissue, the expected signal attenuation, and the background noise level), all of the required data may be collected in about one second. This collection time may be adequate for non-moving tissue such as bone, liver, etc., but is not fast enough to capture motion in arteries, or organs such as kidneys and especially the heart, or in moving joints or muscles.

On the other hand, with ping-based imaging, a single ping, propagating substantially uniformly in three dimensions, can insonify the entire volume, and dynamic beam-forming (focusing) can identify the sources of the echo returns. Using ping-based imaging techniques, a minimum of three pings may be needed to obtain data for a 3D volume, while a minimum of two pings may be needed to obtain data for a 2D slice. In practical terms, ten to fifty (or more) pings may be used to achieve a desired image quality. For example, the use of 25 pings at a rate of 2500 pings per second may require only 0.01 seconds to acquire all the data for the entire 10 cm cube of tissue. For this particular example, data collection may be 100 times faster than with the scanline-based method.

Using ping-based ultrasound imaging techniques, both 2D and 3D frame rates may be increased substantially so as to allow for imaging of 3D volumes in real-time. Furthermore, by applying multiple aperture imaging techniques (e.g., transmitting and receiving ultrasound signals through multiple, spatially or physically separated acoustic windows), the resolution of such real-time 3D images may be dramatically improved relative to single-aperture techniques.

Ping-based multiple aperture ultrasound imaging can provide very powerful real-time three-dimensional imaging capabilities as described above. The benefits of ping-based multiple aperture ultrasound imaging may be achieved by using transducer probes with overall dimensions much larger than traditional ultrasound probes. For example, ping-based multiple aperture ultrasound imaging may be beneficially used with probes having an active imaging surface in excess of 100 $cm^2$. Traditionally, ultrasound elements in a probe are spaced as close together as possible, typically significantly less than (and generally no more than) half a wavelength of the ultrasound frequency being used.

However, using traditional element-to-element spacing in such a large probe would require a cable far too thick for the cable to be usable. Although some tricks may be used to reduce the number of individual conductors required in a cable, a better solution is to increase the allowed spacing between elements, thereby reducing the total number of elements in an array. Use of sparse arrays with traditional scanline-based imaging methods suffers from substantial complications, artifacts, and low resolution and is therefore not generally practical. Based on the research into the use of sparse arrays scanline-based phased array techniques, one would expect the use of sparse arrays with ping-based multiple aperture ultrasound imaging techniques to suffer similar difficulties, but that is unexpectedly not the case. In fact, sparse arrays can be used quite effectively with ping-based multiple aperture ultrasound imaging techniques as described herein.

In some embodiments, sparse arrays of transducer elements may be beneficial in providing an ultrasound probe with a wide total aperture while containing a manageable number of transducer elements.

The following disclosure provides various embodiments of ultrasound probe configurations, methods of making such probes, and methods of using such probes to perform high-frame-rate, high-resolution, real-time 2D, 3D and 4D ultrasound imaging.

An ultrasound transducer probe is provided, comprising an array of ultrasound transducing micro-elements, where each micro-element has a diameter less than 500 microns, a first group of micro-elements electrically connected to a first signal conductor, a second group of micro-elements electrically connected to a second signal conductor, the second signal conductor being electrically separate from the first signal conductor, and a third group of micro-elements positioned between the first group and the second group, the third group of micro-elements being permanently disconnected from any signal conductors.

In some embodiments, each micro-element has a diameter between 25 microns and 200 microns.

In other embodiments, some of the micro-elements of the first group are differently sized than other micro-elements of the first group, wherein the size of a micro-element corresponds its fundamental operating frequency.

In one embodiment, the micro-elements of the first group are connected to a first ground conductor and the micro-elements of the second group are connected to a second ground conductor not electrically connected to the first ground conductor. In another embodiment, the first group of micro-elements includes more micro-elements than the second group. In some embodiments, the first group of micro-elements collectively forms a dedicated transmit element and the second group of micro-elements collectively forms a dedicated receive element.

In one embodiment, the probe comprises a fourth group of micro-elements electrically connected to the first signal conductor by a switch that, when closed causes the fourth group to form a combined element with first group. In some embodiments, the micro-elements of the fourth group collectively surround the micro-elements of the first group. In another embodiment, the fourth group of micro-elements is adjacent to the first group of micro-elements. In one embodiment, the fourth group of micro-elements is contiguous with the first group of micro-elements.

In some embodiments, the combined element has a different shape than the first group alone. In other embodiments, the combined element has a shape that is the same as a shape of the first group but a different size.

An ultrasound imaging system is also provided, comprising a transducer probe having a first array segment and a second array segment separated from the first array segment by a gap of open space, the first and second array segments secured to at least one structural housing member rigidly holding the first and second arrays in fixed positions relative to one another, and an imaging control system containing instructions to: transmit an unfocused ultrasound ping from a transmit aperture approximating a point-source into an object to be imaged, receiving echoes of the ping from reflectors directly below gap with receive transducer elements on both the first array segment and the second array segment, producing a volumetric image of the region below the gap by combining echo data from echoes received by receive elements on both array segments.

In one embodiment, each array segment comprises an array of micro-elements as in any of the previous embodiments.

An ultrasound imaging probe is also provided, comprising a sparse array of ultrasound transducer elements in which less than 50% of potential element positions are occupied by active transducer elements, the sparse array having a first plurality of elements designated as transmit elements and a second plurality of elements designated as receive elements, and wherein no more than N of the receive elements are equidistant to any one transmit element, wherein N is an integer between 1 and 100.

In one embodiment, N is 1, 2, 3, 4, or 5.

In another embodiment, spacing between adjacent elements are pseudo-random distances. In other embodiments, spacing between adjacent elements are non-repeating distances based on a non-repeating number sequence.

In one embodiment, the transmit elements and the receive elements are made of bulk piezoelectric material.

In other embodiments, each transmit element and each receive element is made up of a plurality of micro-elements.

In one embodiment, at least one transmit element or at least one receive element is made up of two sub-groups of micro-elements.

In other embodiments, at least one transmit element or at least one receive element comprises a first plurality micro-elements operating at a first frequency and a second plurality of microelements operating at a second frequency different than the first frequency.

In additional embodiments, at least two of the designated transmit elements are configured to transmit different frequencies of ultrasound than a remainder of the transmit elements.

In other embodiments, spacing between adjacent elements is irregular.

Another ultrasound imaging probe is provided, comprising a sparse array of ultrasound transducer elements in which adjacent transducer elements are spaced by a distance of greater than half a maximum wavelength at which any element of the array is configured to operate, the sparse array having a first plurality of elements designated as transmit elements and a second plurality of elements designated as receive elements.

In one embodiment, spacing between adjacent elements are pseudo-random distances. In other embodiments, spacing between adjacent elements are non-repeating distances based on a non-repeating number sequence.

In one embodiment, the transmit elements and the receive elements are made of bulk piezoelectric material.

In another embodiment, each transmit element and each receive element is made up of a plurality of micro-elements.

In some embodiments, at least one transmit element or at least one receive element is made up of two sub-groups of micro-elements. In another embodiment, at least one transmit element or at least one receive element comprises a first plurality micro-elements operating at a first frequency and a second plurality of microelements operating at a second frequency different than the first frequency.

In additional embodiments, at least two of the designated transmit elements are configured to transmit different frequencies of ultrasound than a remainder of the transmit elements.

In other embodiments, spacing between adjacent elements is irregular.

An ultrasound imaging method is also provided, comprising transmitting a first ultrasound ping from a transmit aperture approximating a point source at a first time, receiving echoes of the first ultrasound ping with a first transducer element between the first time and a second time, the first transducer element coupled to a first receive channel by a first signal conductor, closing a switch at the second time to connect a second transducer element to the first signal conductor, the second transducer element surrounding the first transducer element, receiving echoes of the first ultrasound ping with the first transducer element and the second transducer element between the second time and a third time, and producing an image from the echoes received between the first time and the third time and displaying the image.

In some embodiments, first transducer element has a circular shape, and the second transducer element has a ring shape concentric with the first transducer element.

In an additional embodiment, the first transducer element comprises a first group of micro-elements electrically connected to the first signal conductor. In some embodiments, the second transducer element comprises a second group of micro-elements electrically connectable to the first signal conductor via the switch.

In another embodiment, echoes received between the first time and the second time are near-field echoes.

In some embodiments, the image is a volumetric image. In another embodiment, the image is a two-dimensional image.

An ultrasound imaging method is provided, comprising transmitting a first ultrasound ping from a transmit aperture approximating a point source at a first time, receiving and storing echoes of the first ultrasound ping with a first transducer element, the first transducer element coupled to a first receive channel by a first signal conductor, receiving and storing echoes of the first ultrasound ping with a second transducer element that surrounds the first transducer element, the second transducer element coupled to a second receive channel by a second signal conductor, retrieving first echoes received by the first element between a first time and a third time, retrieving second echoes received by the second element between a second time and the third time, the second time occurring between the first time and the third time, combining the first echoes received between the second time and the third time with the second echoes, and producing an image from the combined echoes and displaying the image.

In some embodiments, the first transducer element has a circular shape, and the second transducer element has a ring shape concentric with the first transducer element.

In other embodiments, the first transducer element comprises a first group of micro-elements electrically connected to the first signal conductor.

In one embodiment, the second transducer element comprises a second group of micro-elements electrically connectable to the first signal conductor via the switch.

In another embodiment, echoes received between the first time and the second time are near-field echoes.

In some embodiments, the image is a volumetric image. In another embodiment, image is a two-dimensional image.

An ultrasound imaging method is also provided, comprising transmitting a first ultrasound ping from a transmit aperture approximating a point source at a first time, receiving echoes of the first ultrasound ping with a first transducer element between the first time and a second time, the first transducer element coupled to a first receive channel by a first signal conductor, opening a switch between the first transducer element and the first signal conductor and simultaneously closing a switch between a second transducer element and the signal conductor, the second transducer element being larger than the first transducer element, receiving echoes of the first ultrasound ping with the second transducer element between the second time and a third time, and producing an image from the echoes received by both the first transducer element and the second transducer element between the first time and the third time and displaying the image.

In one embodiment, opening a switch between the first transducer element and the first signal conductor and simultaneously closing a switch between the second transducer element and the signal conductor comprises operating a single switch.

In one embodiment, the image is a volumetric image. In another embodiment, the image is a two-dimensional image.

An ultrasound imaging method is also provided, comprising transmitting a first ultrasound ping from a transmit aperture approximating a point source at a first time, receiving and storing echoes of the first ultrasound ping with a first transducer element coupled to a first receive channel by a first signal conductor, receiving and storing echoes of the first ultrasound ping with a second transducer element that is larger than the first transducer element, the second transducer element coupled to a second receive channel by a second signal conductor, retrieving first echoes received by the first transducer element between a first time and a second time, retrieving second echoes received by the second transducer element between the second time and a third time, the second time occurring between the first time and the third time, producing an image from the first echoes and the second echoes, and displaying the image.

In one embodiment, the image is a volumetric image. In another embodiment, the image is a two-dimensional image.

An ultrasound imaging method is provided, comprising transmitting an unfocused ultrasound ping from a transmitter approximating a point source into an object to be imaged, receiving echoes of the ping at a first receive element and a second receive element, where a line between the first receive element and the second receive element defines an axis, retrieving position data defining a position of the first receive element and the second receive element relative to a common coordinate system, identifying a first echo sample corresponding to a first reflector received at the first element, and identifying a second echo sample corresponding to the same first reflector received at the second element, determining a first time-of-arrival at which the first sample echo was received at the first receive element, determining second time-of-arrival at which the second sample echo was received at the second receive element, comparing the first time-of-arrival and the second time-of-arrival to determine which of the echo samples corresponding to the first reflector was received first, determining that the first element is closest to the first reflector based on the comparison of times-of-arrival, assigning a greater weight to the first echo sample than the second echo sample, and producing an image of the reflector from the weighted first echo sample and the weighted second echo sample, and displaying the image.

In some embodiments, the method further comprises assigning a greater weight to the second echo sample than a third echo sample received by a third element that is further from the first element than from the second element along the axis, and producing the image of the reflector from the weighted first echo sample, the weighted second echo sample, and the weighted third echo sample.

In one embodiment, the first time-of-arrival is based on explicit timing information in stored echo data.

In another embodiment, the first time-of-arrival is based on implicit timing information in stored echo data.

An ultrasound imaging system is also provided, comprising an array of ultrasound transducer elements, a first transducer element in the array having a long axis and a short axis, wherein the first transducer element produces a first phase signature in response to ultrasound signals received from a first region of an imaged object and a second phase signature in response to ultrasound signals received from a second region of the imaged object, an imaging system configured to transmit ultrasound signals into the object from at least one transmit aperture approximating a point-source and to receive signals produced by the first transducer element in response to echoes of signals transmitted from the at least one transmit aperture, wherein the imaging system is further configured to determine whether a given reflector is located in the first region or the second region based on a phase signature produced by the first transducer element in response to an echo of the reflector received by the first transducer element, and wherein the imaging system is further configured to apply weights to echoes of the reflector received by other receive elements in the array based on the determination of the reflector being located in the first region or the second region, and to produce an image based on the weighted echoes.

In some embodiments, the first region and the second region are quadrants, and wherein the first transducer element further produces a third phase signature in response to ultrasound signals received from a third quadrant of the imaged object, and a fourth phase signature in response to ultrasound signals received from a fourth quadrant of the imaged object, and wherein the first and second quandrants correspond to regions of the object adjacent opposite ends of the short axis and the third and fourth quadrants correspond to regions of the object adjacent opposite ends of the long axis.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 5 is a schematic diagram illustrating an elliptical sparse array arrangement of ultrasound transducer elements.

FIG. 6 is a schematic diagram illustrating a circular sparse array arrangement of ultrasound transducer elements.

FIG. 7 is a schematic diagram illustrating a concave or convex three-dimensional surface sparse array arrangement of ultrasound transducer elements.

FIG. 15 is a schematic illustration of a circular ultrasound imaging probe having a central opening.

FIG. 16A is a schematic illustration showing a top plan view of an ultrasound imaging probe having two probe segments separated by a gap and joined to a bridge handle.

FIG. 16B is a schematic illustration showing a bottom plan view of an ultrasound imaging probe having two probe segments separated by a gap and joined to a bridge handle.

DETAILED DESCRIPTION

Figure 1:
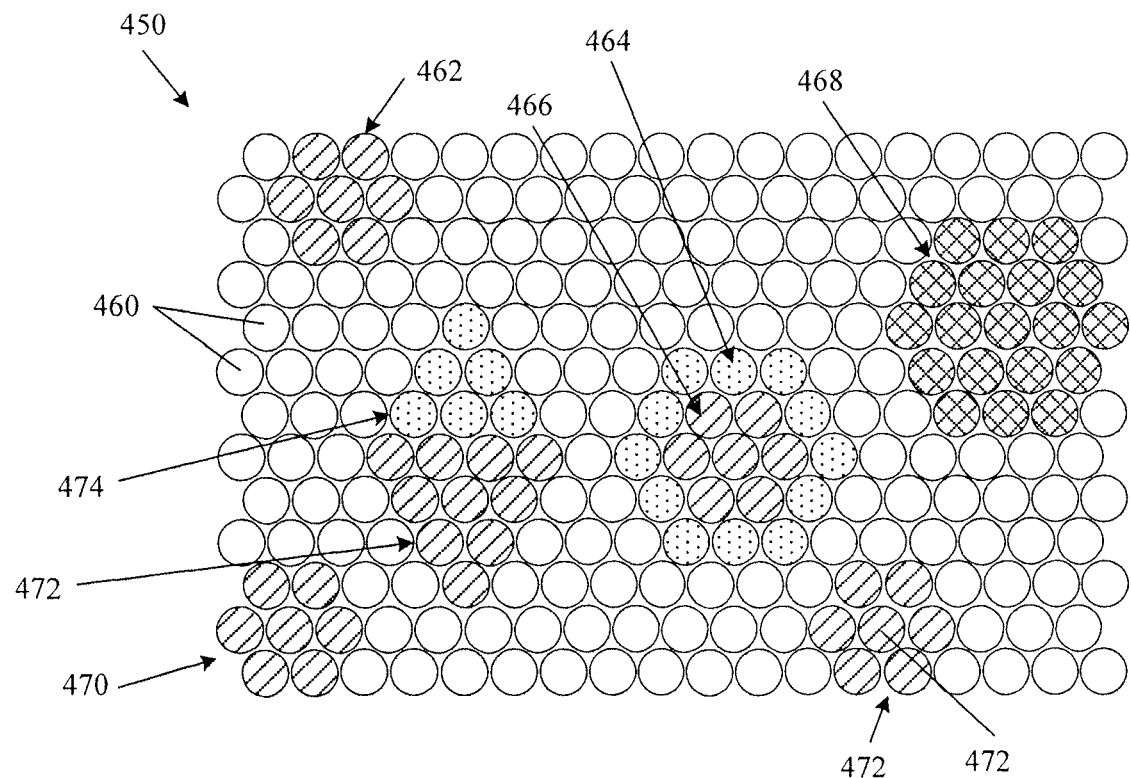
FIG. 1 is a schematic diagram illustrating a sparse array of ultrasound transducer elements made up of micro-elements.

The various embodiments will be described in detail with reference to the accompanying drawings. References made to particular examples and implementations are for illustrative purposes, and are not intended to limit the scope of the invention or the claims.

The present disclosure provides systems and methods for improving the quality of real-time two-dimensional and three-dimensional ultrasound imaging through the use of sparse arrays of various construction, including arrays in which each "element" is made up of a plurality of micro-elements arranged to be operated in concert with one another.

Although the various embodiments are described herein with reference to ultrasound imaging of various anatomic structures, it will be understood that many of the methods and devices shown and described herein may also be used in other applications, such as imaging and evaluating non-anatomic structures and objects. For example, the various embodiments herein may be applied to non-destructive testing applications such as evaluating the quality, integrity, dimensions, or other characteristics of various structures such as welds, pressure vessels, pipes, structural members, beams, etc. The systems and methods may also be used for imaging and/or testing a range of materials including human or animal tissues, solid metals such as iron, steel, aluminum, or titanium, various alloys or composite materials, etc.

Introduction to Key Terms

The following paragraphs provide useful definitions for some terms used frequently herein. Other terms may also be defined as they are used.

As used herein the terms "ultrasound transducer" and "transducer" may carry their ordinary meanings as understood by those skilled in the art of ultrasound imaging technologies, and may refer without limitation to any single component capable of converting an electrical signal into an ultrasonic signal and/or vice versa. For example, in some embodiments, an ultrasound transducer may comprise a piezoelectric device. In other embodiments, ultrasound transducers may comprise capacitive micro-machined ultrasound transducers (CMUT), other micro-machined transducers made of electroactive materials such as piezoelectric materials, ferroic materials, ferroelectric materials, pyroelectric materials, electrostrictive materials, or any other transducing material or device capable of converting ultrasound waves to and from electrical signals.

Transducers are often configured in arrays of multiple individual transducer elements. As used herein, the terms "transducer array" or "array" generally refers to a collection of transducer elements attached to a common support structure. An array may typically (though not necessarily) comprise a plurality of transducer elements mounted to a common backing plate or substrate. Such arrays may have one dimension (1D), two dimensions (2D), 1.X dimensions (1.XD) or three dimensions (3D) as those terms are used elsewhere herein and/or as they are commonly understood in the art. Other dimensioned arrays as understood by those skilled in the art may also be used. Annular arrays, such as concentric circular arrays and elliptical arrays may also be used. In some cases, transducer arrays may include irregularly-spaced transducer elements, sparsely positioned transducer elements (also referred to as sparse arrays), randomly spaced transducer elements, or any other geometric or random arrangement of transducer elements. Elements of an array need not be contiguous and may be separated by non-transducing material or empty space.

An element of a transducer array may be the smallest discretely functional component of an array. For example, in the case of an array of piezoelectric transducer elements, each element may be a single piezoelectric crystal or a single machined section of a piezoelectric crystal. As another example, in an array made up of a plurality of micro-elements (e.g., micro-machined elements, micro-dome elements, or other micro-sized elements), a group of micro-elements may be electrically coupled so as to operate collectively as a single functional element. In such a case, a group of collectively-operating micro-elements may be referred to as a single "element."

As used herein, the terms "transmit element" and "receive element" may carry their ordinary meanings as understood by those skilled in the art of ultrasound imaging technologies. The term "transmit element" may refer without limitation to an ultrasound transducer element which at least momentarily performs a transmit function in which an electrical signal is converted into an ultrasound signal. Similarly, the term "receive element" may refer without limitation to an ultrasound transducer element which at least momentarily performs a receive function in which an ultrasound signal impinging on the element is converted into an electrical signal.

In cases where imaging is performed by transmitting "ping-based" or "point-source transmission" ultrasound signals, the term "transmit element" may refer to a single element or to a plurality of elements operated together to form the desired waveform transmission. For example, a plurality of transducer elements may be activated simultaneously or with delays selected to produce a circular or spherical waveform in the region of interest. Such a plurality of transducers, when operated together to form such a waveform, may have a collective acoustic center which is the apparent point-source origin of the transmitted waveform. Phrased differently, one or more transmit elements may approximate a point-source transmitter if an unfocused spherical waveform produced by the one or more transmit elements appears to have originated from a point source.

Transmitted ultrasound signals may be focused in a particular direction, or may be unfocused, transmitting in all directions or a wide range of directions. Transmission of ultrasound into a medium may also be referred to herein as "insonifying." An object or structure which reflects ultrasound waves may be referred to as a "reflector" or a "scatterer."

As used herein, terms referring to a "position" or "location" of a transducer element refer to an acoustic center position exhibited by the element. In some cases, an acoustic center position of an element may be precisely coincident with a mechanical or geometric center of the element, group of elements, or group of micro-elements. However, in many cases an acoustic center position of an element may be different than a mechanical or geometric center of the element due to various factors such as manufacturing irregularities, damage, irregular element geometries, or other factors. Acoustic center positions of elements may be determined using various calibration techniques such as those described in US Patent Application Publication 2014/0043933, titled "Calibration of Multiple Aperture Ultrasound Probes," U.S. Pat. No. 9,282,945, titled "Calibration of Ultrasound Probes," or other methods.

As used herein, the term "aperture" may refer to a single transducer element or a group of transducer elements that are collectively managed as a common group by imaging control electronics. For example, in some embodiments an aperture may be a grouping of elements which may be physically separate and distinct from elements of an adjacent aperture. However, adjacent apertures need not necessarily be physically separate or distinct. Conversely, a single aperture may include elements of two or more physically separate or distinct transducer arrays or elements spaced from one another by any distance or different distances. In some cases, two or more elements need not be adjacent to one another to be included in a common aperture with one another. For example, distinct groups of transducer elements (e.g., a "left aperture") may be constructed from a left array, plus the left half of a physically distinct center array, while a "right aperture" may be constructed from a right array, plus the right half of a physically distinct center array.

As used herein, the terms "receive aperture," "insonifying aperture," and/or "transmit aperture" are used herein to mean an individual element, a group of elements within an array, or even entire arrays, that perform the desired transmit or receive function as a group. In some embodiments, such transmit and receive apertures may be created as physically separate components with dedicated functionality. In other embodiments, any number of transmit and/or receive apertures may be dynamically defined electronically as needed. In other embodiments, a multiple aperture ultrasound imaging system may use a combination of dedicated-function and dynamic-function apertures. In some cases, elements may be assigned to different apertures during two or more ping cycles (as defined below).

As used herein, the term "ping cycle" refers to a cycle that begins with the transmission of a ping from a transmit aperture approximating a point source and ends when all available (or all desired) echoes of that transmitted ping have been received by receive transducer elements. In many cases, ping cycles may be distinct and separated by some time period. In other cases, ping cycles may overlap one another in time. That is, an N+1th ping cycle may begin (with transmission of a ping) before an Nth ping cycle is completed (i.e., before all echoes of the Nth ping are received).

In various embodiments, a single "image" or "image frame" may be produced from the echoes of one or more transmitted pings. Therefore, an "imaging cycle" or "image cycle" may refer to a cycle that begins with the transmission of a first ping that will contribute to an image and may end with the reception of echoes of a final ping contributing to the same image. In various embodiments, a single imaging cycle may include one, two, three, four, five, or more ping cycles.

As used herein, the term "total aperture" refers to the overall size of all imaging apertures in a probe. In other words, the term "total aperture" may refer to one or more dimensions defined by a maximum distance between the furthest-most transducer elements of any combination of transmit and/or receive elements used for a particular imaging cycle. Thus, the total aperture may be made up of any number of sub-apertures designated as send or receive apertures for a particular cycle. In the case of a single-aperture imaging arrangement, the total aperture, sub-aperture, transmit aperture, and receive aperture may all have the same dimensions. In the case of a multiple aperture imaging arrangement, the dimensions of the total aperture may include the sum of the dimensions of all send and receive apertures plus any space between apertures.

In some embodiments, two apertures may be located adjacent to one another on a continuous array. In other embodiments, two apertures may overlap one another on a continuous array, such that at least one element functions as part of two separate apertures. The location, function, number of elements and physical size of an aperture may be defined dynamically in any manner needed for a particular application.

Elements and arrays described herein may also be multi-function. That is, the designation of transducer elements or arrays as transmitters in one instance does not preclude their immediate re-designation as receivers in the next instance. Moreover, embodiments of control systems herein include the capabilities for making such designations electronically based on user inputs, pre-set scan or resolution criteria, or other automatically determined criteria.

As used herein, the "image-able field" of the imaging system may be any area or volume of an imaged object or substance that may practically be imaged by the imaging system. For a ping-based imaging system as described herein, the term "image-able field" may be synonymous with the term "insonified region." The term "region of interest" may refer to a two-dimensional or three-dimensional region within the image-able field. The extents of an image-able field relative to a probe may be imposed by physical limits (e.g., based on signal-to-noise ratios or attenuation rates) or may be chosen logical limits (e.g., based on a desired region of interest).

As used herein, the term "pixel" refers to a region of two-dimensional space within an image-able field of the imaging system. The term "pixel" is not intended to be limited to a pixel of a display device, and may represent a region of a real-world-scale object that is either larger or smaller than a display pixel. A "pixel" may represent a region of the image-able field of any real-world size, and in some cases may represent a region smaller than any resolvable object of the imaging system. Pixels may be, but need not necessarily be square or rectangular, and may have any shape allowing for contiguous two-dimensional representation of the image-able field. In some cases, data representing a pixel may not be displayed, but may still be processed as a unit and referred to as a "pixel."

As used herein, the term "voxel" refers to a region of three-dimensional space within an image-able field of the imaging system. The term "voxel" is not intended to be limited to any particular portion of a two-dimensional or three-dimensional display device, and may represent a region of a real-world-scale object that is either larger or smaller than a display voxel. A "voxel" may represent a three-dimensional region of the image-able field of any real-world size, and in some cases may represent a region smaller than any resolvable object of the imaging system. Voxels may be, but need not necessarily be three-dimensional square or rectangular prisms. Voxels may have any shape allowing for contiguous three-dimensional representation of the image-able field. In some cases, data representing a voxel may not be displayed, but may still be processed as a unit and referred to as a "voxel."

As used herein, the terms "pixel location" and "voxel location" (or "position") refer to a location within the image-able field that is identifiable by a coordinate system, which may be a Cartesian coordinate system or any other coordinate system. Unless otherwise specified, references to a location of a pixel or voxel may generally refer to a center-point (e.g., center-of-mass, circular center, etc.) of the pixel or voxel.

As used herein, a pixel may be described as "intersecting" a voxel. A two-dimensional pixel may be defined as intersecting a three-dimensional voxel using any desired convention. For example, for square pixels and cubic voxels, a pixel intersecting a voxel may be a square face of the voxel or any other square or rectangle passing through the voxel. If a coordinate system used for pixels is different than a coordinate system used for voxels, then one pixel may intersect multiple voxels.

As used herein, the term "echo" refers to an ultrasound wavefront or an analog or digital representation of an ultrasound wavefront that arrives at a receive transducer element. Because imaging methods described herein allow for an extremely wide range of probe configurations, some ultrasound signals arriving at a receive transducer element may originate at a transmit transducer element on an opposite side of an imaged object. Such wavefronts are also intended to be included within the definition of an "echo" even if such wavefronts may also be described as "transmitted" or "deflected."

As used herein, the terms "reflector" and "scatterer" refer to a physical portion of a physical object being imaged. When struck by a wavefront, reflectors and scatterers will tend to re-radiate a wavefront in a direction generally dictated by physics. The terms are not intended to limit the relative geometry or positions of transmitters, scatterers, and reflectors.

As used herein, the verb terms "reflect" and "scatter" refer to the effect of a scatterer on a propagating ultrasound wavefront. In some cases, a wavefront that is only slightly deflected (e.g., forming a combined transmit element/scatterer/receive element angle approaching 180°) by a scatterer may still be described as having been "reflected" by that scatterer (or "reflector").

As used herein, the term "sample" refers to a digital data element in a physical volatile or non-volatile storage medium. Unless context suggests otherwise, "samples" described herein generally refer to data elements representing a discrete portion of a received ultrasound waveform. A time-varying electrical signal produced by a transducer element vibrating in response to a received ultrasound wavefront may be quantified and digitally sampled at a sample rate in order to produce a series of digital values representing the received time-varying electrical signal. Those values may be referred to as "samples." In some cases, a "sample" may include an interpolated value in between two digitally stored sample values.

If digital sampling is done at a known sample rate (usually, but not necessarily a consistent sample rate), the position of each sample (e.g., as measured by a location in memory device, or a position in a sequence of values) may be directly related to an arrival time of the wavefront segment responsible for each sample value.

As used herein, the term "beamform" refers to the process of determining a value for pixels or voxels based on a sample value (directly stored or interpolated), the known acoustic center position of a transmit element responsible for the sample value, and the known acoustic center position of a receive element responsible for the sample value. Beamforming is described in further detail elsewhere herein.

As used herein, the term "image" (as a noun) refers to a human-visible graphical representation of a physical object or a series of non-transitory digital values stored on a physical storage medium that may be interpreted by software and/or an image processor to produce such a graphical representation. As used herein, the term "image" does not necessarily imply any particular degree of quality or human-readability. An "image" may refer to a two-dimensional representation (e.g., a cross-section, in some cases) or a three-dimensional volumetric representation of an object. Therefore, a "volumetric image" may include a visible representation of a three-dimensional point cloud or digital data representing the three-dimensional point cloud. As used herein, the terms "image" and "imaging" (in verb form) refer to a process that results in an image.

Introduction to Point-Source Transmission Ultrasound Imaging

In various embodiments, point-source transmission ultrasound imaging, otherwise referred to as ping-based ultrasound imaging, provides several advantages over traditional scanline-based imaging. Point-source transmission differs in its spatial characteristics from a "phased array transmission" which focuses energy in a particular direction from the transducer element array along a directed scanline. A point-source pulse (also referred to herein as a "ping") may be transmitted so as to generate either a two-dimensional circular wavefront or a three-dimensional spherical wavefront, thereby insonifying as wide an area as possible in the two-dimensional or three-dimensional region of interest. Echoes from scatterers in the region of interest may return to all of the elements of receive apertures (or all of those elements not blocked by obstacles preventing transmission of the echoes). Those received echo signals may be filtered, amplified, digitized and stored in short term or long term memory (depending on the needs or capabilities of a particular system).

Images may then be reconstructed from received echoes by determining positions of reflectors responsible for received echo samples. The position of each reflector responsible for a digital echo sample may be calculated based on the arrival time of the received echo sample (which may be inferred based on a sample position and a known sampling rate) relative to the known time at which the ping was transmitted, the acoustic position of the transmit element(s) responsible for the echo sample, and the acoustic position of the receive element responsible for the echo sample. This process of determining positions of reflectors is generally referred to herein as beamforming.

Beamforming may be performed by a software-based, firmware-based, or hardware-based dynamic beamforming technique, in which a beamformer's focus may be continuously changed to focus at a particular pixel position corresponding to a reflector position. Such a beamformer may be used to plot the position of echoes received from point-source pings. In some embodiments, such a dynamic beamformer may plot the locus of each echo signal based on a round-trip travel time of the signal from the transmitter to an individual receive transducer element.

In the two-dimensional imaging case, for a given echo sample produced by a transmit transducer element and a receive transducer element, the locus of possible positions of the target reflector responsible for the echo sample will be an ellipse mathematically defined by two foci. A first focus of the ellipse will be at the position of the transmit transducer element and the second focus will be at the position of the receive transducer element. Although several other possible reflector positions lie along the same ellipse, echoes of the same target reflector will also be received by other receive transducer elements. The slightly different positions of each receive transducer element means that each receive element will define a slightly different ellipse for the target reflector. Accumulating the results by summing the ellipses for multiple receive elements at slightly different positions will indicate an intersection of the ellipses for a reflector. As echo samples from more receive elements are combined with the first, the intersecting ellipses will converge towards a point at which the target reflector is located. Similarly, echoes of pings transmitted from different transmit element positions may also be combined to further refine reflector points. The target reflector position may be correlated with a pixel location representing the reflector. The combined sample values may be used to determine a display intensity for a display pixel at the pixel location. The echo amplitudes received by any number of transmit positions and receive elements may thereby be combined to form each pixel. In other embodiments the computation can be organized differently to arrive at substantially the same result.

Various algorithms may be used for combining echo signals received by separate receive elements. For example, some embodiments may process echo-signals individually, plotting each echo signal at all possible locations along its ellipse, then proceeding to the next echo signal. Alternatively, each pixel location may be processed individually, identifying and processing all echo samples potentially contributing to that pixel location before proceeding to the next pixel location.

Image quality may be further improved by combining images formed by the beamformer from one or more subsequent transmitted pings, transmitted from the same or a different point-source (or multiple different point-sources). Still further improvements to image quality may be obtained by combining images formed by more than one receive aperture.

An important consideration is whether the summation of images from different pings, different transmit point-sources or different receive apertures should be coherent summation (phase sensitive) or incoherent summation (summing magnitude of the signals without phase information).

The decision as to whether to use coherent or incoherent summation may be influenced by the lateral extent/size of the receive aperture(s) and/or the transmit aperture(s). In some embodiments, it may be convenient to confine the size of an aperture to conform to the assumption that the average speed of sound is substantially the same for every path from a scatterer to each element of the transmit or receive aperture. For narrow receive apertures this simplifying assumption is easily met. However, as the width of the receive aperture increases, an inflection point may be reached (referred to herein as the "maximum coherent aperture width" or "maximum coherence width"), beyond which paths traveled by echoes of a common reflector will necessarily pass though different types of tissue having intrinsically different speeds of sound when returning to the elements furthest apart from one another. When this difference results in receive wavefront phase shifts approaching or exceeding 180 degrees, additional receive elements extended beyond the maximum coherence width will actually degrade the image rather than improve it.

The same maximum coherent aperture size considerations may also apply to the size of transmit apertures, which may include a plurality of transducer elements. In the case of two-dimensional transducer arrays used in three-dimensional imaging (or 3D data collection), it may be useful to define a maximum coherent aperture size in two dimensions. Thus, in various embodiments a maximum coherent aperture may be defined as a group of transducer elements in a square, circle, polygon or other two-dimensional shape with a maximum distance between any two elements such that phase cancellation will be avoided when echo data received at the elements of the aperture are coherently combined.

Therefore, in order to realize the benefits (e.g., in terms of increased spatial resolution) of a wide probe with a total aperture width far greater than the maximum coherent aperture width, the full probe width may be physically or logically divided into multiple transmit and/or receive apertures, each of which may be limited to an effective width less than or equal to the maximum coherent aperture width, and thus small enough to avoid phase cancellation of received signals.

The maximum coherence width can be different for different patients (or different test objects), for different probe positions on the same patient, and for other variables such as ultrasound frequency. In some embodiments, a compromise width may be determined for a given probe and/or imaging system. In other embodiments, a multiple aperture ultrasound imaging control system may be configured with a dynamic algorithm to subdivide the available elements into groups that are small enough to avoid significant image-degrading phase cancellation. In various embodiments, a particular coherent aperture size may be determined automatically by a control system, or manually through user input via a user control such as a dial or slider.

In some embodiments, coherent (phase sensitive) summation may be used to combine echo data received by transducer elements located on a common receive aperture resulting from one or more pings. In some embodiments, incoherent summation may be used to combine echo data or image data received by separate receive apertures if such receive apertures are sized and positioned so as to form a combined total aperture that is greater than a maximum coherence width for a given imaging target.

Two-dimensional ping-based beamforming may implicitly assume that the wavefronts emitted from the point-source are physically circular in the region of interest. In actuality, the wavefront may also have some penetration in the dimension orthogonal to the scanning plane (i.e., some energy may essentially "leak" into the dimension perpendicular to the desired two-dimensional image plane, which may have the effect of reducing the effective imaging depth). Additionally, the "circular" wavefront may actually be limited to a semicircle or a fraction of a circle less than 180 degrees ahead of the front face of the transducer according to the unique off-axis properties of the transducing material used. Similarly, a three-dimensional "spherical" wavefront may have an actual shape of a hemisphere or less than a hemisphere within the medium to be imaged.

Ping-Based Imaging for 3D Ultrasound Imaging

The above description of point-source ultrasound imaging (also referred to herein as "ping-based" imaging) predominantly describes two-dimensional imaging in which ultrasound signals are focused into a narrow field approximating a plane in a region of an image. Such two-dimensional focusing may be accomplished with lensing or other techniques. Ping-based imaging can also be extended to real-time three-dimensional imaging without adding significant complexity. Three-dimensional ping-based imaging can be performed using an ultrasound probe with transducer elements spaced from one another in two dimensions. Some example probe configurations are described elsewhere herein.

When a three-dimensional pulse is initiated from a point-source transmit transducer, the resulting semi-spherical wavefront travels into the insonified region containing a region of interest (ROI) where some of the ultrasound energy may be reflected (or deflected) by scatterers in the ROI. Some of the echoes from the scatterers may travel towards receive transducer elements of the probe, where the echoes may be detected, amplified, digitized, and stored in a short-term or long-term memory device. Each digitized sample value may represent a scatterer from the ROI. As in the 2D case, the magnitude of each received sample, along with its time of arrival and the exact positions of the transmit and receive transducers used, may be analyzed to define a locus of points identifying potential positions of the scatterer. In the 3D case, such a locus is an ellipsoid having as its foci the positions of the transmitter point source and receive transducer element. Each unique combination of transmit and receive transducer elements may define a separate view of the same reflector. Thus, by combining information from ellipsoids produced from multiple transmit-receive transducer element combinations, the actual location of each reflector may be more accurately represented.

For example, in some embodiments an image in a 3D array of voxels may be assembled in computer memory by beginning with an evaluation of a selected digital sample. The selected digitized sample value may be written into every voxel indicated by the corresponding ellipsoid described above. Proceeding to do the same with every other collected sample value, and then combining all resulting ellipsoids may produce a more refined image. Real scatterers would be indicated by the intersection of many ellipsoids whereas parts of the ellipsoids not reinforced by other ellipsoids would have low levels of signal and may be treated as noise (i.e., eliminated or reduced by filters, gain adjustments, or other image processing steps).

In other embodiments, the order of computation may be changed by beginning with a selected voxel in a final 3D image volume to be produced. For example, for a selected voxel, the closest stored sample or interpolated sample may be identified for each transmitter/receiver pair. All samples corresponding to the selected voxel may then be evaluated and summed (or averaged) to produce a final representation of the voxel. Closeness of a sample to a selected voxel may be determined by calculating the vector distance from the three-dimensional position of a transmitter (i.e., the transmitter used to produce the sample) to the selected voxel position plus the vector distance from the selected voxel position to the position of a receiver used to produce the sample. Such a linear distance may be related to the time-divided sample values by dividing the total path length by speed of sound through the imaged object. Using such a method, the samples corresponding to a calculated time may be associated with the selected voxel. Once identified, data corresponding to a common voxel may be combined according to a chosen combining algorithm.

Image Layer Combining

Techniques for determining the location for received echo samples are generally referred to herein as beamforming, while techniques for combining information obtained from multiple transmitter/receiver combinations or from multiple separate pings transmitted using the same transmitter/receiver combination may generally be referred to as image layer combining. In various embodiments, a frame may be made up of any number of combined image layers. Frames may be displayed sequentially at a desired frame-rate on a display to form a moving image or video. The above-described beamforming processes may beneficially also be used for evaluating pixel values in a 2D cross-sectional slice through a 3D volume using raw echo data. In various embodiments, such 2D slices may be taken at any arbitrary angle or along any curved path through the 3D volume. The same techniques may also be used to zoom in (i.e., increase the size of features) using raw echo data rather than enlarging processed pixels or voxels.

Images obtained from different unique combinations of one ping and one receive element and/or combinations of one ping and one receive aperture may be referred to herein as "sub-image layers." Multiple sub-image layers may be combined coherently to improve overall image quality (e.g., by combining multiple ellipses or ellipsoids as described above). Additional image layer combining may be performed to further improve the quality of a final image. In the context of image layer combining, the term "image" may refer to a single two-dimensional pixel, a single voxel of a three-dimensional volume or a collection of any number of pixels or voxels.

Image layer combining may be described in terms of four image layer levels. These include base-level image layers, first-level image layers, second-level image layers and third-level image layers. As used herein, the phrase base-level image layer refers to an image obtained by beamforming echoes received at a single receive element from a single transmitted ping. As described above, the beamforming process defines an ellipse corresponding to each echo sample. Therefore, a base-level image may include a series of such ellipses representing all of the echoes of a single ping received by a single receive element. Such an image may not be particularly useful for diagnostic imaging purposes, but may be used for other purposes.

A first-level image layer may be formed from echoes received at a single receive aperture resulting from a single ping from a single transmit aperture (where a "transmit aperture" can be a composite point-source transmit element, a single-element transmitter, or a group of transmit elements). For a unique combination of a single ping and a single receive aperture, the echoes received by all the receive elements in the receive aperture may be summed coherently to obtain a first-level image layer. Alternatively, first-level images may be formed by combining the echoes of two or more pings received at elements of a common receive aperture.

Multiple first-level image layers resulting from echoes of multiple transmit pings (from the same or different transmit apertures) received at a single receive aperture can be summed together to produce a second-level image layer. Second-level image layers may be further processed to improve alignment or other image characteristics.

Third-level images may be obtained by combining second-level image layers formed with data from multiple receive apertures. In some embodiments, third-level images may be displayed as sequential time-domain frames to form a moving image.

In some embodiments, pixels or voxels of a first-level image layer may also be formed by summing in-phase and quadrature echo data, that is by summing each echo with an echo ¼ wavelength delayed for each receive-aperture element. In some cases, echo data may be sampled and stored as an in-phase data set and as a separate quadrature data set. In other cases, if the digital sampling rate is divisible by four, then a quadrature sample corresponding to an in-phase sample may be identified by selecting a sample at an appropriate number of samples prior to the in-phase sample. If the desired quadrature sample does not correspond to an existing whole sample, a quadrature sample may be obtained by interpolation. Combining in-phase and quadrature data for a single image (pixel, voxel or collection of pixels or voxels) may provide the advantage of increasing the resolution of the echo data without introducing blurring effects. Similarly, samples at values other than ¼ wavelength may be combined with in-phase samples in order to improve various imaging characteristics.

Combination, summation or averaging of various image layers may be accomplished either by coherent addition, incoherent addition, or a combination of the two. Coherent addition (incorporating both phase and magnitude information during image layer summation) tends to maximize lateral resolution, whereas incoherent addition (summing magnitudes only and omitting phase information) tends to average out speckle noise and minimize the effects of image layer alignment errors that may be caused by minor variations in the speed of sound through the imaged medium. Speckle noise is reduced through incoherent summing because each image layer will tend to develop its own independent speckle pattern, and summing the patterns incoherently has the effect of averaging out these speckle patterns. Alternatively, if the patterns are added coherently, they reinforce each other and only one strong speckle pattern results.

In most embodiments, echoes received by elements of a single receive aperture are typically combined coherently. In some embodiments, the number of receive apertures and/or the size of each receive aperture may be changed in order to maximize some desired combination of image quality metrics such as lateral resolution, speed-of-sound variation tolerance, speckle noise reduction, etc. In some embodiments, such alternative element-to-aperture grouping arrangements may be selectable by a user. In other embodiments, such arrangements may be automatically selected or developed by an imaging system.

Variations in the speed of sound may be tolerated by incoherent addition as follows: Summing two pixels coherently with a speed-of-sound variation resulting in only half a wavelength's delay (e.g., approximately 0.25 mm for 3 MHz ultrasound) results in destructive phase cancellation, which causes significant image data loss; if the pixels are added incoherently, the same or even greater delay causes only an insignificant spatial distortion in the image layer and no loss of image data. The incoherent addition of such image layers may result in some smoothing of the final image (in some embodiments, such smoothing may be added intentionally to make the image more readable).

At all three image layer levels, coherent addition can lead to maximum lateral resolution of a multiple aperture system if the geometry of the probe elements is known to a desired degree of precision and the assumption of a constant speed of sound across all paths is valid. Likewise, at all image layer levels, incoherent addition leads to the best averaging out of speckle noise and tolerance of minor variations in speed of sound through the imaged medium.

In some embodiments, coherent addition can be used to combine image layers resulting from apertures for which phase cancellation is not likely to be a problem, and incoherent addition can then be used where phase cancellation would be more likely to present a problem, such as when combining images formed from echoes received at different receive apertures separated by a distance exceeding some threshold.

In some embodiments, all first-level images may be formed by using coherent addition of all sub-image layers obtained from elements of a common receive aperture, assuming the receive aperture has a width less than the maximum coherent aperture width. For second and third level image layers, many combinations of coherent and incoherent summation are possible. For example, in some embodiments, second-level image layers may be formed by coherently summing contributing first-level image layers, while third-level image layers may be formed by incoherent summing of the contributing second-level image layers.

Time-domain frames may be formed by any level of image layer depending on the desired trade-off between processing time and image quality. Higher-level images will tend to be of higher quality, but may also require more processing time. Thus, if it is desired to provide real-time imaging, the level of image layer combination processing may be limited in order to display images without significant "lag" being visible to the operator. The details of such a trade-off may depend on the particular processing hardware in use as well as other factors.

2D Imaging while Collecting 3D Data

In some embodiments, a form of 2D imaging may be performed using a probe and imaging system configured for 3D imaging by simply beamforming and displaying only a 2D slice of data from the received three-dimensional echo data. For example, such techniques may be used in order to reduce a beamform calculation and simplify display for real-time imaging using an imaging device with limited processing capability, while still retaining the full 3D echo data.

For example, a two-dimensional plane may be selected (automatically or by a user) from the voxels making up a three-dimensional volumetric representation of the imaged region, voxels intersecting the selected plane may be identified. An image window may be defined by automatically or manually selecting a portion of the selected plane, and a two-dimensional image of the selected image window may then be formed by beamforming only those echo samples corresponding to the voxels intersecting the selected plane and lying within the selected image window. The selected two-dimensional image window may then be displayed in real-time while three-dimensional data of the entire insonified volume is simultaneously collected. In some cases two separate image windows in the same or different image planes may be defined and imaged simultaneously from the same set of real-time three-dimensional echo data.

The collected full 3D echo data may be beamformed and reviewed at a later time using a device with greater processing power. In some embodiments, the 2D slice to be beamformed and displayed may be automatically selected by an imaging device. Alternatively, the 2D slice to be beamformed and displayed may be selected or adjusted by an operator of the device.

Data Capture & Offline Analysis

In various embodiments, raw un-beamformed echo data resulting from a ping transmitted from point-source transmit transducers and received by one or more arrays of receive transducer elements may be captured and stored in a raw data memory device for subsequent retrieval and analysis. Alternately, captured echo data may be digitally transmitted over a network for remote processing, beamforming, and/or viewing. In addition to echo data, additional data may also be stored and/or transmitted over a network and retrieved for subsequent and/or remote image generation and analysis. Such additional data may include calibration data describing the positions of the transmitting and receiving transducer elements, and transmit data describing the identity (or position) of transmitting transducers associated with specific echo data.

After retrieving such data, a clinician may use the data to reconstruct imaging sessions in a variety of ways while making adjustments that may not have been made during a live imaging session. For example, images of a series of 2D slices through a 3D volume may be generated and shown in succession in order to simulate a 2D transducer passing across a surface of the region of interest. Examples of these and other methods are described in Applicant's US Patent Application Publication 2014/0058266, titled, "Ultrasound Imaging System Memory Architecture" and PCT Patent Application Publication WO2016/028787, titled "Network-Based Ultrasound Imaging System."

Some embodiments of a probe configured for imaging an entire patient's body or a substantial portion of a patient's body may comprise an array of designated point-source transmitters and designated receive elements sized and arranged to cover a substantial portion of the desired region of a patient's body. For example, a probe may be sized to cover substantially half of a patient's chest or more. Such a probe may have a maximum dimension of about 8 cm to about 10 cm.

Alternatively, a much smaller probe capable of insonifying a conically-shaped volume of, for example, + or −30 degrees, can be placed on a patient's body such that an organ of interest may be included in the cone. Such a probe may be placed in more than one place to cover a larger volume of interest.

Designated Point Source Transmitters

As described above, a point-source transmitter may be approximated using a single small transducer element of a transducer array. When performing 2D ping imaging using a 1D array (an array of elements with parallel longitudinal axes, typically including a lens to focus the signal into a single imaging plane), a single element may be able to produce a ping with sufficient energy in the imaging plane to achieve imaging at a reasonable depth.

Additionally, in various embodiments, an "apparent point-source transmitter" transducer may be configured to produce a waveform that both approximates an actual point-source and has sufficient energy to produce high quality images at the desired depth. In some cases, such apparent point-source transmitters may be configured such that ultrasound power output may be limited only by safety considerations within the imaged medium.

As used herein, the phrase "point-source" refers to a point in two-dimensional (2D) space or three-dimensional (3D) space that represents a center point of a transmitted 2D or 3D ultrasound waveform, respectively. In some embodiments, such a point is ideally an infinitely small point corresponding to a produced wavefront with a consistent semi-spherical shape. In embodiments in which such a waveform is produced by a single small element, such a point may lie on the surface of the transducer element. As used herein, the terms "semi-spherical pulse" and "semi-spherical wavefront" may refer to any ultrasound wavefront with a spherical-section shape, including wavefronts with approximately spherical-section shapes greater than or less-than an ideal semi-sphere. Similarly, the terms "semi-circular pulse" and "semi-circular wavefront" may refer to any ultrasound wavefront which appears in an imaging plane to have a circular-section shape, including wavefronts with approximately circular-section shapes greater than or less-than an ideal semi-circle.

In some cases, multiple (e.g., two, three, four or more) small transducer elements from a common transmit/receive array may be excited simultaneously to produce a ping with more energy than may be produced by a single element.

In some embodiments, a designated point source transmitter may comprise a large transducer shaped and configured to produce a relatively high-power waveform that "appears" to have originated from a point-source even if the location of the apparent point source does not correspond to a physical structure responsible for producing the wavefront—in other words, an apparent point-source. When performing beamforming calculations to determine the location of reflectors based on the timing of received echoes, the location of the apparent point-source may be used as the origin of the transmitted ping wavefront. In various embodiments, an approximate location of an apparent point source may be estimated based on a physical geometry or other characteristic of a designated point source transmitter.

In some embodiments, particularly suitable shapes for designated point source transmitters may include individual elements in the shape of concave and convex spherical caps sized to deliver sufficient ultrasound power to perform real-time three-dimensional ping-based imaging. Convex spherical caps may generally be referred to herein as "dome-shaped," while concave spherical caps may be referred to as "bowl-shaped." Some examples of imaging probes incorporating examples of such spherical cap transducer elements (otherwise referred to as "apparent point source" transducer elements) are shown and described in U.S. Patent Application Publication No. US 2015/0080727.

Examples of Piezoelectric Materials and Manufacturing

In some cases, a designated point source transmitter may include a single structure or one or more element sub-structures arranged in a planar, convex, or concave shape. In some embodiments, each designated transmitter element or receive transducer elements may be constructed from a single contiguous piece of a piezoelectric material. Such elements may be referred to herein as "bulk" elements or as being made from "bulk piezoelectric" materials. In other embodiments, transmitter and/or receiver elements may be composed of a plurality of sub-element structures, such as cut piezoelectric materials, micro-element structures (as described further below), or other structures that may be operated collectively to form a complete element.

In some embodiments, transmitter elements or receiver elements may be in the form of a thin shell of a piezoelectric material in a planar shape or in the shape of a truncated spherical cap. Such elements may be made of any material exhibiting piezoelectric properties. Many naturally occurring and synthetic materials are known to exhibit piezoelectric properties that may be of a character suitable for use in ultrasound imaging applications. In the case of ping-based multiple aperture ultrasound imaging, ultrasound ping signals may be transmitted at frequencies commonly used in diagnostic medical ultrasound, e.g., in the range of about 1 MHz to about 20 MHz or more. Thus, apparent point-source transducers with fundamental frequencies within this range may be suitable for use in ping-based multiple aperture imaging.

Naturally-occurring piezoelectric materials include quartz, topaz and tourmaline, while man-made piezoelectric ceramic materials include lead zirconate titanate (PZT), barium titanate, lead metaniobate, & polyvinylidene difluoride ($PVF_2$—not naturally piezoelectric, but may be made so by heating in the presence of a strong electrical field). Some man-made piezoelectric ceramic materials may be combined with non-piezoelectric polymer materials to create piezo-composites.

In the case of bulk elements made from piezoelectric materials, the thickness of a designated transmitter element, whether planar, bowl-shaped, or dome-shaped, may be directly related to the fundamental frequency of the transducer. In some cases (e.g., for some piezoelectric ceramic materials), the thickness of a transducer shell may be equal to about half a wavelength of its corresponding fundamental frequency. However, depending on the materials and/or structures used, the shell thickness may be differently related to a transducer element's fundamental frequency. Manufacturing processes may also vary depending on the piezoelectric material used and other factors.

For example, natural or man-made piezoelectric material may be machined using traditional techniques in order to form the desired shape directly from a block of material. Such machining may be performed using mechanical cutters, water jets or any other available machining technique. Alternatively, a block or sheet of piezoelectric material may be machined into a plurality of elements attached to a flexible substrate which may then be formed into the desired shape. For example, a plurality of concentric ring cuts 42 and radial cuts 44 may be made in a sheet of piezoelectric material, which may then be formed over a backing material with the desired shape (e.g., a spherical-cap). In such embodiments, the individual sub-element sections that make up the element may be electrically connected so as to transmit simultaneously without phasing.

In some embodiments, a desired shape may be molded (e.g., by injection molding, die casting, or other molding process) from a piezo-composite material. Examples of molding processes that may be adapted to forming spherical-cap elements are described in U.S. Pat. Nos. 5,340,510 and 5,625,149.

Ultrasound transducers may also be produced in desired shapes using additive manufacturing techniques (commonly known as 3D printing techniques). For example, US Patent Application Publication 2013/0076207 and US Patent Application Publication 2013/0088122 describe systems and methods for forming transducers in the shape of cylindrical posts. Similar techniques may also be adapted to form transducers with spherical-cap or other shapes. Additionally, other manufacturing techniques such as laser sintering, stereo lithography, chemical vapor deposition or any other suitable techniques may be used to produce transducers in the shapes and sizes described herein.

Capacitive Micromachined Ultrasound Transducer (CMUT) formation techniques may also be used to form transducers of desired shapes onto a pre-shaped substrate. WO 2012/112540 shows and describes some examples of structures and techniques that may be adapted to forming spherical-cap shaped transducers. Alternately, a transducer element may be made by forming an array of CMUT transducers on a substrate pre-formed into a desired shape (e.g., a concave or convex spherical cap as described above). In such embodiments, the CMUT elements may be electrically connected so as to transmit simultaneously without phasing.

In some embodiments, transducer elements may be made up of a plurality of micro-elements which may be made using lithographic techniques, thin-film deposition techniques, etching techniques, additive manufacturing techniques, surface micromachining, bulk micromachining, and/or other methods. For example, U.S. Pat. No. 6,222,304 to Bernstein (which is incorporated herein by reference) describes processes for making micro-shell transducer elements which include a substrate, an electro-active medium mounted on the substrate and including an arched section spaced from the substrate defining a chamber between the substrate and arched section, and a pair of electrodes mounted on the medium for either applying an electric field across the medium for flexing the arched section or sensing the electric field generated by a flexure of the medium. Other techniques may also be used to produce micro-elements of different types. For example, in some cases, the flexible "arched section" may be replaced by a flexible planar section or a flexible concave section that may be flexed upon application of an appropriate electrical signal.

In some embodiments, in order to build transducer elements into a probe, the "front" surface of each element (e.g., the inside surface of a concave element, the outside surface of a convex element or the outward-facing surface of a planar element) may be plated with an electrically conductive layer (such as a metal) so as to allow electrical connection to the element. In some embodiments, the entire inner surface and the entire outer surface of each element may be plated, thereby allowing the entire piezoelectric shell to be activated by applying an electrical signal across the two plated surfaces. In other embodiments, less than an entire shell may be activated by plating less than an entire inner and/or outer surface of the shell. In this way, a similar range of element sizes may be made functional from a single physical structure.

Using materials and methods available, transmitter and receiver elements may be made in a range of shapes, such as having a top surface that is planar, convex, concave, or combination of shapes. Transmitter and/or receiver elements may also have various plan-view shapes such as circular, rectangular, pentagonal, hexagonal, heptagonal, octagonal, other polygonal, or others. Elements can be electrically and logically connected to a controller so as to be dedicated transmitters, dedicated receivers, or switchable between transmit and receive functions. Elements can be arranged into various arrays, such as regular arrays, irregular arrays, sparse arrays, or arrays that may be controlled so as to be operated as regular, irregular, or sparse arrays.

Ultrasound Imaging Arrays Constructed from Micro-Elements

Ultrasound probes made up of ultrasound transmitters and receivers may be made by various techniques suitable for producing arrays of micro-elements. As used herein, the term "micro-element" refers to very small transducer elements with sizes (e.g., diameters) on the order of less than about 1,000 microns, in some cases about 10 microns to about 500 microns, in some cases between about 50 microns to about 200 microns, in some cases between about 50 and about 150 microns, in some cases between about 10 microns and about 25 microns, in some cases between about 25 microns to about 50 microns, and in some cases between about 50 microns and about 100 microns. In some cases, a micro-element may be defined as any element that has a diameter equal to less than half a wavelength of the ultrasound frequency in the imaged material at which the micro-element will be used.

Typically, micro-elements may be too small to be mechanically machined from traditional bulk piezoelectric materials, and may therefore be made using lithographic techniques, thin-film deposition techniques, etching techniques, additive manufacturing techniques, surface micromachining, bulk micromachining, and/or other methods. For example, U.S. Pat. No. 6,222,304 to Bernstein (which is incorporated herein by reference) describes processes for making micro-shell transducer elements which include a substrate, an electro-active medium mounted on the substrate and including an arched section spaced from the substrate defining a chamber between the substrate and arched section, and a pair of electrodes mounted on the medium for either applying an electric field across the medium for flexing the arched section (i.e., in order to transmit an ultrasound signal) or sensing the electric field generated by a flexure of the medium (i.e., in order to receive an ultrasound signal impinging on the micro-element). Other techniques may also be used to produce micro-elements of different types. For example, in some cases, the flexible "arched section" may be replaced by a flexible planar section or a flexible concave section that may be flexed upon application of an appropriate electrical signal and/or may be sensitive to received impulses.

In some embodiments, it may be desirable to create arrays of micro-elements capable of conforming to a desired shape. In such embodiments, a pattern of micro-elements may be formed on a semiconductor substrate using one or more of the above techniques, a back-surface (i.e., opposite the surface on which micro-elements lie) of the substrate may be thinned to make the substrate flexible to a desired degree, and the substrate may then be conformed to a new shape and secured to a supporting material. In various embodiments, such thinning and re-shaping may be performed over an entire substrate surface or in localized regions.

There are generally four methods for wafer thinning common in the art of semiconductor manufacturing. They include mechanical grinding, chemical mechanical polishing (CMP), wet etching and atmospheric downstream plasma (ADP), and dry chemical etching (DCE).

Using such techniques (or combinations thereof), one or more sections of an array of micro-elements may be conformed so as to form entire arrays or array sections in desired shapes. For example, arrays may be shaped so as to conform to a portion of a human anatomy, such as a breast, a joint (e.g., a knee, elbow, wrist, ankle, etc.), a skull, or other anatomical structure. In other examples, arrays may be shaped so as to conform to mechanical, structural, or industrial parts. In other examples, array sections may be shaped to form three-dimensional element groups arranged to exhibit desired transmit patterns. For example, such techniques may be used to form transducer element groups configured to transmit apparent point-source waveforms.

In some embodiments, an array of micro-elements may be conformed so as to form dome-shaped sections or dish-shaped sections, such as the spherical section elements described herein. For example, convex or concave dome-shaped transmit elements optimized for near-field imaging may be formed from a plurality of micro-elements on a thinned section of substrate and conformed to a desired dome shape.

In some embodiments, a dome-shape may be optimized for near-field imaging based on transmit angles of micro-elements that will make up the dome. Each micro-element may have a transmit angle relative to a centerline of a transmitted wavefront. The transmit angle of a micro-element defines the angle at which the energy of a transmitted wavefront drops below some threshold value.

In some embodiments, a convex dome shape optimized for near-field imaging may be defined by a spherical section with a cut elevation selected such that wavefronts transmitted from micro-elements at a low region of the dome (i.e., a region of the spherical section adjacent an attachment point with the surrounding micro-element array) will not tend to impinge directly on adjacent micro-elements. The micro-elements of such a dome-shaped group may be electrically connected such that they may be operated as a single element. As in various other examples herein, the spherical center point of such an element may be used as the acoustic center point for the purpose of beamforming calculations for pings transmitted from such a spherical-section shaped transmitter element.

In some embodiments, a concave dish shape optimized for far-field imaging may be defined by a spherical section with a cut elevation selected such that wavefronts transmitted from micro-elements within the dish will not tend to impinge directly on other micro-elements within the dish-shaped element. The micro-elements of such a dish-shaped group may be electrically connected such that they may be operated together to collectively form a single transmitter and/or receiver element. As in various other examples, the spherical center point of such an element group may be used as the acoustic center point for the purpose of beamforming calculations for pings transmitted from such a spherical-section shaped transmitter element or receiver element.

In some embodiments, an overall shape of a substrate supporting an array of micro-elements may be conformed into a desired shape. For example, in some embodiments a substrate supporting an array of micro-elements may be formed into complex overall shapes. In some cases, an array of micro-elements may include one or more surfaces with inflected sections, such as to conform to an anatomical or other structure.

Figure 2:
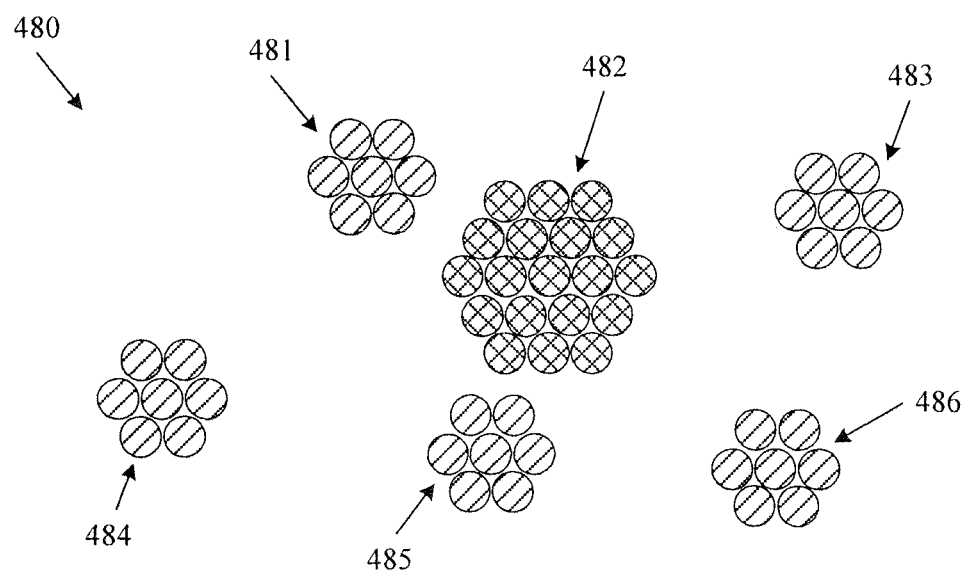
FIG. 2 is a schematic diagram illustrating a sparse array of ultrasound transducer elements made up of micro-elements with no micro-elements between identified elements.

In various embodiments, micro-elements may be grouped to form shaped transducer elements such as those described elsewhere herein. Groups of micro-elements may be treated collectively as a single element in the various processes described herein, and may be referred to herein as "element groups" or "micro-element groups." For example, as shown in FIG. 1 and FIG. 2, a plurality of adjacent micro-elements may be logically and electrically treated as a single unit so as to form transducer elements of a desired size and shape, and in a desired location. In some embodiments, spherical cap or dome-shaped elements may be formed from a plurality of micro-elements.

One advantage of forming transducer elements from a group of such micro-elements is that the position of each micro-element may be known very precisely based on the precision of manufacturing techniques used to produce the micro-elements. Therefore, the position of each micro-element-group may also be known very precisely.

In some embodiments, a group of micro-elements forming a single transducer element group may collectively share a single electrical ground conductor and a single electrical signal conductor. In some embodiments, each of the ground conductor and the signal conductor for each transducer element group may form a differential pair independent of signal and ground conductors for other elements of the array. In other words, micro-elements in a group of micro-elements forming an element group may share a single ground conductor that is not shared with ground conductors of micro-elements belonging to other element groups between the probe and a connector joining the probe to control electronics. Similarly, micro-elements of an element group may share a single signal conductor that is not shared with signal conductors of micro-elements of other element groups between the probe and a connector joining the probe to control electronics. In some embodiments, some micro-elements (e.g., a sub-set of micro-elements forming an element group) may be joined to signal and/or ground conductors of other micro-elements via a switch configured to allow the sub-set of micro-elements to be switchably joined to signal and/or ground conductors of other micro-elements.

Alternately, some or all micro-element groups may share a common ground conductor and/or a common signal conductor. For example, in some embodiments micro-element groups that form elements that are collectively part of a single aperture may share a common ground conductor and/or a common signal conductor. In other embodiments, one or more signal and/or ground conductors may be shared in a multiplexed arrangement, such as time-division-multiplexed communications, or other multiplexing method.

Sparse Array Probes for Real Time 3D Imaging

Ping-based multiple aperture ultrasound imaging can provide very powerful real-time three-dimensional imaging capabilities as described above. The benefits of ping-based multiple aperture ultrasound imaging may be achieved by using transducer probes with overall dimensions much larger than traditional ultrasound probes. For example, ping-based multiple aperture ultrasound imaging may be beneficially used with probes having an active imaging surface in excess of 100 $cm^2$. Traditionally, ultrasound elements in a probe are spaced as close together as possible, typically significantly less than (and generally no more than) half a wavelength of the ultrasound frequency being used.

However, using traditional element-to-element spacing in such a large probe would require a cable far too thick for the cable to be usable. Although some tricks may be used to reduce the number of individual conductors required in a cable, a better solution is to increase the allowed spacing between elements, thereby reducing the total number of elements in an array. Use of sparse arrays with traditional scanline-based imaging methods suffers from substantial complications, artifacts, and low resolution and is therefore not generally practical. Based on the research into the use of sparse arrays scanline-based phased array techniques, one would expect the use of sparse arrays with ping-based multiple aperture ultrasound imaging techniques to suffer similar difficulties, but that is unexpectedly not the case. In fact, sparse arrays can be used quite effectively with ping-based multiple aperture ultrasound imaging techniques as described herein.

In some embodiments, sparse arrays of transducer elements may be beneficial in providing an ultrasound probe with a wide total aperture while containing a manageable number of transducer elements.

In other fields, a "sparse array" is generally defined as an array in which the majority of array positions have a zero or null value. In some cases, a similar definition may be applied to an array of ultrasound transducer elements. In the context of an array of ultrasound transducer elements, a sparse array may be defined as an array of potential element positions in which a majority of the element positions contain no active elements. For example, the inactive element positions may contain no transducers, or may contain transducers that are not active at a specified time, if ever. For example, inactive element positions may comprise transducer elements that are temporarily or permanently electrically disconnected from imaging control electronics. In other examples, inactive element positions may comprise empty spaces (or spaces filled with non-transducing material) of sizes equivalent to a transducer element.

In some cases, an ultrasound transducer array in which less than a majority of element positions contain no active elements may also be considered "sparse" if average spacing between adjacent elements exceeds a threshold distance. For example, in some cases, an ultrasound transducer array may be considered "sparse" if all (or nearly all) adjacent elements of the array are spaced from one another by a distance of at least half a wavelength of the ultrasound transmitted and/or received by the elements. In still other cases, an ultrasound transducer array may be considered "sparse" if at least a majority of elements of the array are spaced from adjacent elements by a distance of at least a threshold distance. If an array is configured to operate at more than one ultrasound frequency, then a threshold distance may be half of the maximum wavelength at which any part of the array is configured to operate.

In some various, ultrasound probes comprising a sparse array of ultrasound transmitters and receivers may be made using one or more of the various micro-element or sub-element configurations described herein. For example, in some embodiments, a sparse array may be formed from a continuous array of micro-elements by electrically assigning micro-elements to element-groups where the element groups are located in a sparse arrangement. Examples of such embodiments are described below with reference to FIG. 1. In some such embodiments, micro-elements that are not assigned to an element-group may simply be electrically inactive.

In some embodiments, instead of a continuous array of micro-elements (as in FIG. 1), a sparse-array transducer probe may comprise a plurality of groups of micro-elements formed in desired locations on a substrate without necessarily forming additional micro-elements between micro-element groups. FIG. 2 illustrates an example of such a sparse array 480 made up of separated micro-element groups 481-486.

In some embodiments, ultrasound probes comprising a sparse array of ultrasound transmitters and receivers may be made by forming individual transducer elements from bulk piezoelectric material, mechanically picking up and placing each element in a precise location on a substrate, securing each element to the substrate, and making electrical connections to each element. Bulk piezoelectric elements may be made in any shape or size as described herein.

In some embodiments, a sparse array probe may be effectively used by 3D multiple aperture imaging techniques as described herein, and in some cases may be preferred to a continuous array densely populated with transducer elements, particularly when spacing between receivers and transmitters avoid certain patterns. In certain circumstances, using a probe having a sparse two-dimensional or three-dimensional array of regularly-spaced transducer elements with the ping-based multiple aperture imaging beamforming techniques described herein may result in the production of self-reinforcing artifacts that may undesirably degrade image quality. Such artifacts may be the result of phase cancellation causing certain returning echo signals to cancel one another out before reaching some receive elements thereby producing distortions in the form of extremely dark and/or extremely bright bands in the resulting image.

In some embodiments, such artifacts may be avoided or mitigated by positioning transducer elements at inconsistent distances from one another in a sparse array. In other words, phase cancellation artifacts may be avoided or mitigated by positioning transmit and receive elements such that no two transducer elements are an equal distance from any single third element. In some cases, a small amount of element position equivalence may be acceptable. In examples of such embodiments, a probe may be constructed such that no more than "N" receive elements are located an equal distance from a single transmitter, where "N" is an integer value between 1 and 1,000 or more, more commonly between about 1 and 100, and in some specific examples N may be 1, 2, 3, 4, 5, 10, 100 or more and wherein all of the receiver elements receive the same frequency of ultrasound signal.

In some embodiments, transmit elements may be regularly-spaced relative to one another while spacing receive elements at irregular distances relative to the transmit elements. In other embodiments, both transmit elements and receive elements may be irregularly positioned in a sparse array.

Figure 3:
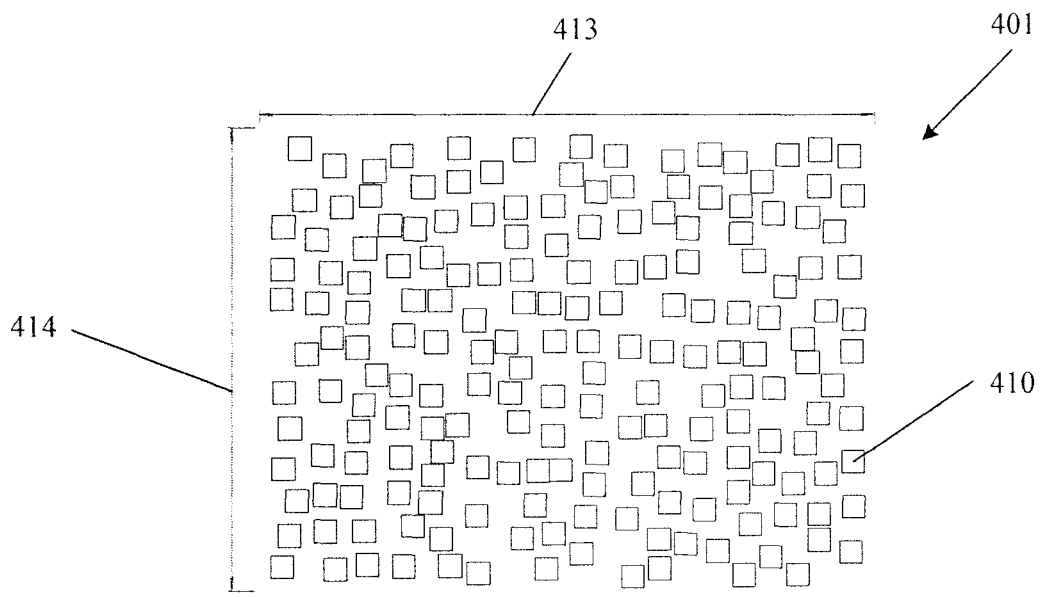
FIG. 3 is a schematic diagram illustrating rectangular a sparse array arrangement of ultrasound transducer elements represented as squares.
Figure 4:
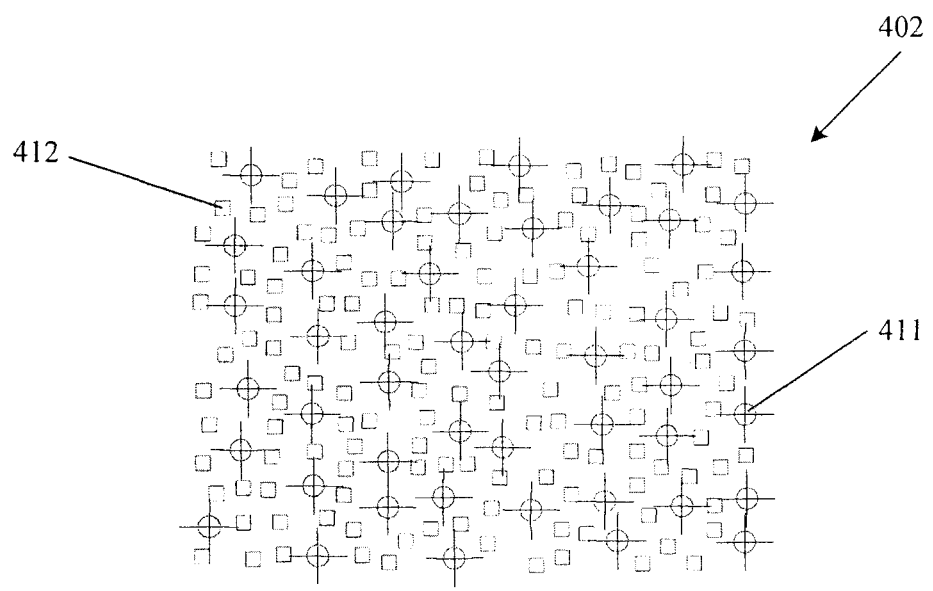
FIG. 4 is a schematic diagram illustrating a rectangular sparse array arrangement of ultrasound transducer elements.

In some embodiments, a two-dimensional sparse array of transducer elements positioned to mitigate phase cancellation artifacts may include elements spaced from one another at "random" distances. FIG. 3 and FIG. 4 illustrate examples of two-dimensional sparse array element positions in which a distance between any two adjacent elements is not exactly equal to any other distance between two adjacent elements. In the example of FIG. 3 and FIG. 4, the distances between adjacent elements are effectively random in the sense that there is no mathematical pattern relating the distances.

FIG. 3 illustrates a two-dimensional array 401 made up of elements 410 unevenly spaced from one another in two dimensions according to a pseudo-random pattern. In various embodiments, the array 401 illustrated in FIG. 3 may have an overall length dimension 413 and/or an overall width dimension 414 of about 3 cm to about 10 cm or more. Each element 410 of the array 401 may have a square shape, a circular shape, a polygonal shape, or any other regular or irregular shape. For example, FIG. 4 illustrates a sparse array 402 embodiment in which designated transmit elements are shown as circular elements 411 while designated receive elements are shown as square elements 412. In other embodiments, all elements may be circular, square, or otherwise-shaped elements even if some are designated transmitters and others are designated receivers.

In addition to the generally rectangular arrays shown in FIG. 3 and FIG. 4, sparse arrays 401, 402 of ultrasound elements with uneven spacing may be arranged in other shapes, such as a generally oval shaped array 403 as shown in FIG. 5, or a generally circular shaped array 404 as shown in FIG. 6.

Sparse arrays of ultrasound elements with uneven spacing may also be arranged in a generally planar configuration, or a generally concave or convex configuration 405 as shown in FIG. 7. The arrangement of transducer elements shown in FIG. 7 may be made convex by a supporting substrate layer positioned on the concave side of the pattern of elements. Similarly, supporting the elements with a substrate on the convex side of the pattern will provide a concave array. In other embodiments, sparse arrays may be arranged for use in intra-venous ultrasound probes or other specialized probes.

In some embodiments, spacing distances between elements may be non-repeating random or pseudo-random distances obtained with use of a random or pseudo-random number generation algorithm. In other examples, spacing distances between elements may be irregular values which may be based on non-repeating values from an integer sequence such as the Fibonacci sequence or any other non-repeating numeric sequence. In some cases, an algorithm may be applied to values from a numeric sequence in order to maintain element spacing distances within a desired range. For example, in some embodiments distances between adjacent elements may be constrained to a range such as 1 mm to 10 mm (or 1 mm to 20 mm or more).

In various embodiments, the spacing between transducer elements need only be un-equal by an amount at least as great as a manufacturing tolerance of a manufacturing method used to construct the array. For example, if an array manufacturing process is capable of positioning elements on a substrate within a distance of +/1 100 microns of an intended position, then it may be desirable to design the two spacing distances so as to be different by at least 100 microns. In other embodiments, the spacing between transducer elements need only be un-equal by an amount based on a frequency of ultrasound used.

Figure 8:
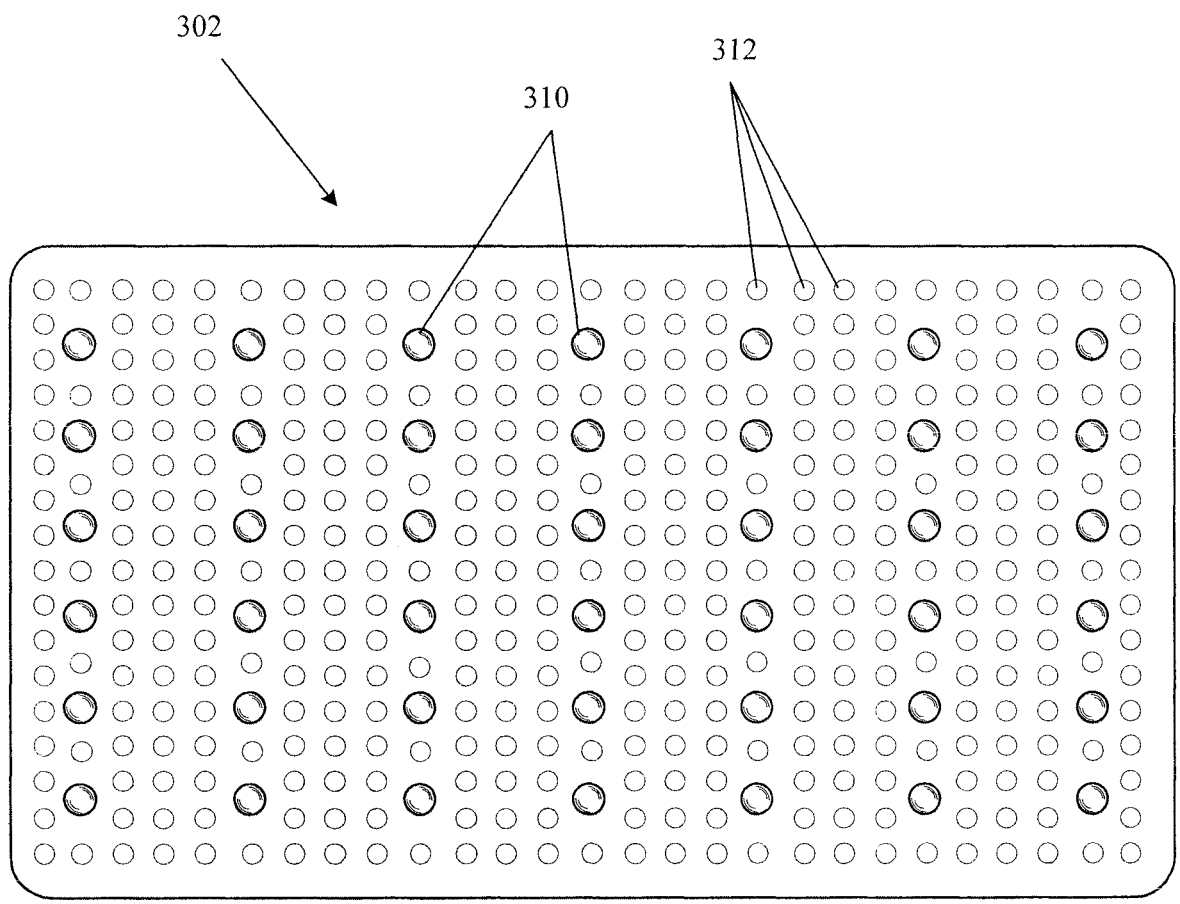
FIG. 8 is a plan view illustration of a sparse array of regularly-spaced transmit and receive transducer elements.

In some medical imaging applications, variations in tissues may introduce enough randomness to signals to substantially avoid or minimize most phase cancellation artifacts. Therefore, in some cases a sparse array probe may include a larger number of regularly-spaced transducer elements if other factors can be expected to minimize phase cancellation artifacts. For example, FIG. 8 illustrates an example array 302 of dedicated transmit elements 310 and receive elements 312. In various embodiments, the transmit elements 310 and/or the receive elements 312 may be replaced with any other transmit or receive elements described elsewhere herein. FIG. 15 and FIG. 16B also illustrate elements with examples of regularly spaced elements which may contain elements of any construction such as those described herein.

Multiple Frequency Sparse Arrays

In some cases, phase cancellation artifacts may be avoided or mitigated by constructing and/or operating a sparse array probe such that only a small number of regularly-spaced elements operate at the same ultrasound frequency as one another. For example, some embodiments of sparse array probes may be constructed and/or operated such that no more than "N" receive elements operating at the same ultrasound frequency (or combination of frequencies) are equidistant to any one transmit element. In such embodiments, N may be an integer between 1 and 100, in some specific examples, N may be 1, 2, 3, 4, 5 or more. Thus, for example, a probe may contain any number of receive elements equidistant to one or more transmit elements as long as no more than N of the receivers are operated at the same ultrasound frequency (or combination of frequencies).

The ultrasound frequency (or combination of frequencies) at which any given transmit or receive element may be operated may be based on structural characteristics of the element (e.g., material, thickness, diameter, or other dimensions) and/or variable operational characteristics such as an electric voltage or signal shape applied to the element. Which and to what degree such factors may change an element's operating frequency may depend on the element material and/or the process by which it is manufactured. For example, while many transducers may have a fundamental frequency, many can also be driven (i.e., operated in transmit or receive) at frequencies other than their fundamental frequency. The range of frequencies at which any particular transducer element may be driven may depend on many factors such as the material, construction, available power, etc.

For example, in various embodiments, an operating frequency of a micro-element may be determined by a diameter of a flexible section of material, such as the "arched section" described by Bernstein referenced above or a similarly-configured flexible planar or concave section. Thus, in some embodiments, micro-element groups may be made up entirely of micro-elements configured to operate at the same frequency, or may be made up of micro-elements configured to operate at different frequencies. For example, in some embodiments an outer micro-element group (e.g., 464 in FIG. 1) may be configured to operate at a different (e.g., a higher frequency or a lower frequency) than micro-elements making up a central group 466, either by being physically constructed differently or by being operated differently.

Figure 9:
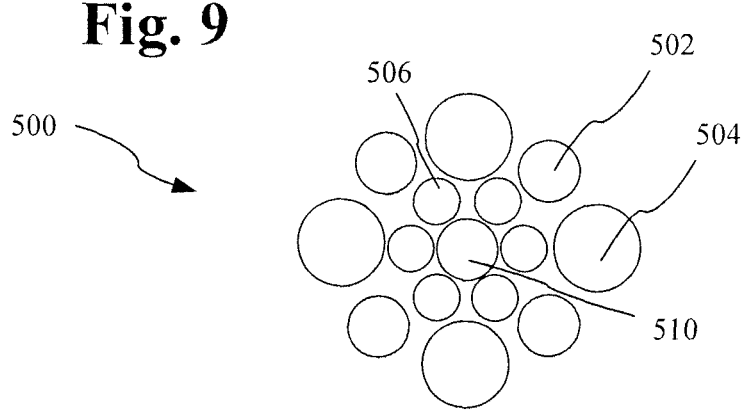
FIG. 9 is a schematic diagram illustrating an example multi-frequency transmit transducer element made up of a plurality of micro-elements of different sizes.

FIG. 9 illustrates an example of a group of micro-elements of different sizes arranged to form a multi-frequency transmit element. As described above, the fundamental transmit frequency of a micro-element may be a function of the size of a flexible surface member. Therefore, a multi-frequency transmit element group may be formed by providing micro-elements of varying sizes arranged so as to be controllable as a common element group. The group 500 of micro-elements in FIG. 9 includes micro-elements of three different sizes. In other embodiments, micro-elements of two, four, five, six, or more different sizes may be grouped into a transmitter or receiver group. Other patterns or numbers of micro-elements of each size may also be used, depending on the waveform characteristics desired.

The variously-sized micro-elements of FIG. 9 may be electrically connected so as to be activated simultaneously as a group, such as by providing a single electrical signal conductor and a single electrical ground conductor common to all of the micro-elements of a transmit group such as that shown in FIG. 9.

In some embodiments, a micro-element array may comprise a plurality of transmit element groups containing micro-elements of various sizes. In some embodiments, different transmit elements may be provided with different mixes of micro-element sizes in order to produce pings with different multi-frequency combinations. In this way, each transmit group may have a unique frequency signature. If different transmitters in a probe have different mixes of micro-element sizes to produce a different frequency signature, then pings transmitted from one transmitter may be distinguished from pings transmitted by a second transmitter, even if pings from the two transmitters are transmitted at the same time or during overlapping ping cycles.

In other words, when a probe is configured to include at least two transmitters configured to transmit multi-frequency waveforms and receive elements of the probe are sensitive to all of the transmitted frequencies, then echoes received by each receive element of the probe may be mapped to the transmitter that produced the echo based only on the frequency signature of the received echoes. This may be tremendously beneficial in increasing ping rates and/or frame rates well beyond the limits imposed by single-frequency imaging.

Sparse Arrays with Varied or Variable Element Sizes

In some embodiments, a size of transducer elements may be varied instead of or in addition to varying spacing between elements. For example, in some embodiments, a sparse ultrasound array may be entirely made up of transducer elements of various (and/or variable) sizes as shown for example in FIG. 1, FIG. 10A, FIG. 10B, FIG. 11A, FIG. 11B.

In some embodiments, micro-element groups may be switched between a first configuration in which a first element group includes a first group of micro-elements and a second configuration in which the first element group includes a second group of micro-elements in addition to (or subtracted from) the first group of micro-elements. In some embodiments, such switching between a first configuration and a second configuration may be performed in between ping cycles. That is, a first ping may be transmitted and echoes of the first ping may be received by the micro-elements of the first configuration of the element group. Then, a second ping may be transmitted, and echoes of the second ping may be received by the second configuration in which the first element group includes a second group of micro-elements in addition to the first group of micro-elements.

Similarly, a transmit element group may be configured to be switchable between a first configuration and a second configuration that is larger, smaller, or differently shaped than the first configuration.

Alternatively, element groups may be switched between a first configuration and a second configuration within a single ping cycle. In such embodiments, a first ping may be transmitted, a first plurality of echoes of the first ping may be received by the micro-elements of the first configuration of the element group, and the switch may then be closed so that a second plurality of echoes of the first ping may be received by the micro-elements of the second configuration of the element group in addition to or instead of the micro-elements of the first configuration. In some embodiments, the first plurality of echoes may be relatively near-field echoes that are produced by reflectors closer than a threshold distance to the receiver micro-elements, and the second plurality of echoes may be mid-field or far-field echoes that are produced by reflectors further than a threshold distance from the receiver micro-elements. Assuming an approximately constant speed of sound, the threshold may be a time value, such that the first plurality of echoes may be received with the first configuration of micro-elements until a switch-time at which a switch may activate the second configuration of micro-elements to allow the second plurality of echoes to be received after the switch-time until the end of the ping cycle.

In some embodiments, individual micro-elements or groups of micro-elements may be electrically switchable so as to be selectively included in or excluded from a micro-element group forming an element or an aperture. Transmit element groups or receive element groups may be configured to be switchable between a first configuration and a second configuration, where the second configuration is larger, smaller, or differently shaped than the first configuration.

For example, FIG. 1 illustrates an example section of a continuous array 450 of micro-elements 460. Some of the micro-elements 460 are indicated as having been assigned to an element-group 462, 464, 466, 468, 470, and 472. FIG. 1 further illustrates an outer group of micro-elements 464 identified by stippling surrounding a central group 466 of micro-elements. In one embodiment of the illustrated example, a larger element group 468 may be used as a transmit element, and the smaller element groups 462, 464, 470, and 472 may be used as receive elements.

In some embodiments, the outer group 464 may be switchable as a group so as to selectively form a larger element in combination with the central group 466. Similar element groups may be formed with any number of adjacent micro-element groups in any desired configuration. Such a variably-sized element may be used as a transmit element, as a receive element, or as both.

Another example is provided in the groups 472 and 474 which provide for switchable configurations with different shapes and sizes. One or more switches may be provided to allow the group 474 to be included with the group 472 so that both groups 472 and 474 may operate together as a single element (e.g., as a receive element or as a transmit element). The elongated element formed by the combination of sub-groups 472 and 474 may be beneficially used in combination with the process for estimating a position of a reflector using an elongated receive element.

In some embodiments, ping-based receive beamforming calculations (as described herein) may be performed using the position of the circular center of the center micro-element (e.g., 744) of a micro-element group as the acoustic center position of the transducer element group. In embodiments in which a micro-element group is arranged such that it does not include a centrally-located micro-element, the position of the micro-element group may be defined at a center-of-mass point or a geometric center point of the group of micro-elements. In other embodiments, various calibration processes may be used to measure, determine, and/or to refine an acoustic center position for each transducer element group. Examples of suitable calibration processes are described in US Patent Application Publication US 2014/0043933 titled "Calibration of Multiple Aperture Ultrasound Probes," U.S. Pat. No. 9,282,945 titled "Calibration of Ultrasound Probes," and U.S. Pat. No. 9,510,806 titled "Alignment of Ultrasound Transducer Arrays and Multiple Aperture Probe Assembly," each of which is incorporated by reference herein.

Figure 10A:
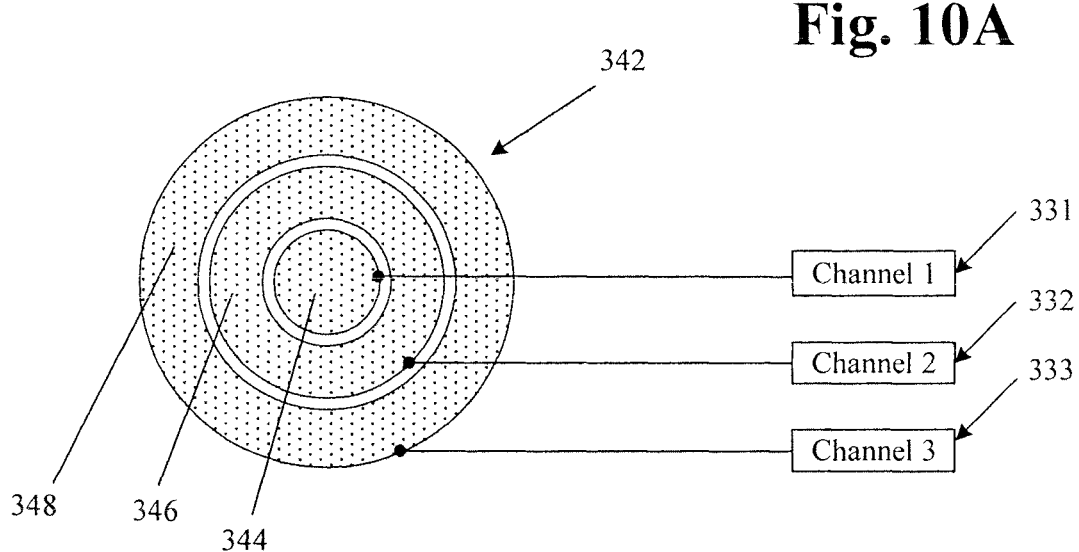
FIG. 10A is a schematic illustration of an embodiment of an electric circuit that may be used to connect a group of concentric receive elements to separate receive channels of a receive subsystem.
Figure 10B:
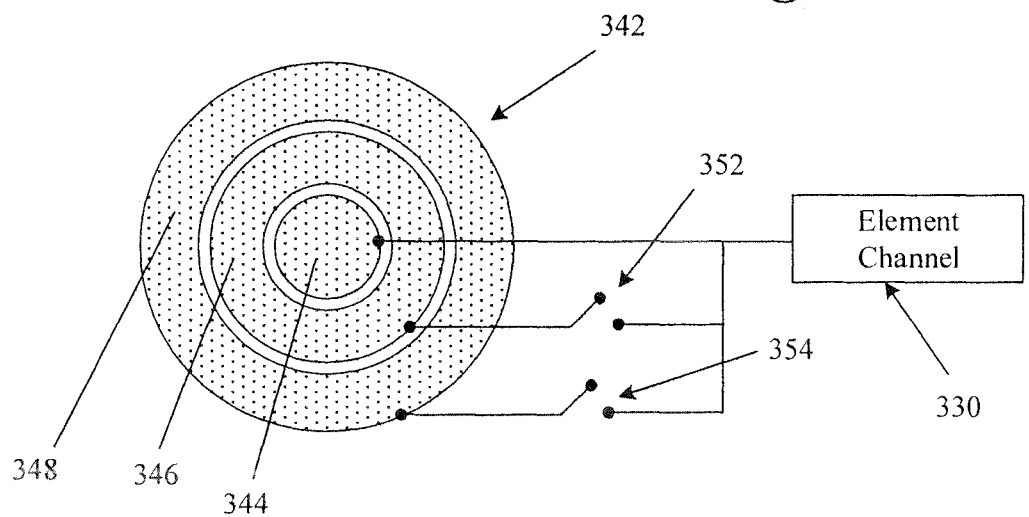
FIG. 10B is a schematic illustration of an embodiment of an electric circuit that may be used to connect a group of concentric receive elements to a receive channel of a receive subsystem.

FIGS. 10A and 10B illustrate examples of radially symmetrical groups 342 of switchable concentric sub-elements 344, 346, 348 which may be operated in concert with one another. The group 342 may include a central circular receive element 344 surrounded by one or more concentric-ring receive elements 346, 348 providing the ability to obtain the benefits of elements of various sizes in a small physical footprint while maintaining a consistent acoustic center position. In various embodiments, a center element 344 may be surrounded by two, three or more rings, depending on the needs of a particular application.

In some embodiments, the space (or "kerf") between the center circular element 344 and the inner ring 346 and the space/kerf between rings 344, 348 may be as small as possible so as to provide as much of a seamless transition between adjacent ring elements as possible. In one example, the inner circular element 344 may have a diameter of about 1 mm, the inner ring 346 may have a width of about 0.5 mm, and the outer ring 348 may have a width of about 0.5 mm. In such an example, the center element 344 and inner ring element 346 may be combined to mimic a circular element with a diameter of about 2 mm, and the center element 344, inner ring element 346, and outer ring element 348 may be combined to mimic a circular element with a diameter of about 3 mm.

As shown in FIG. 10A, in some embodiments, each element 344, 346, 348 may be individually connected to a separate receive channel 331, 332, 333 of a receive subsystem so as to allow echoes received with each concentric element to be stored separately. Using such an arrangement, a complete image may be formed from received echoes after echoes have been received with all receive elements of all sizes. This may allow for a "digital switching" process in which echo data received with the sub-elements may be selectively combined to improve a final image. Stored echoes may be retrieved from the memory device and combined so as to obtain an optimal image based on the timing of received echoes and/or the location of the transmitted ping.

In such embodiments, echo data received with the center element 344 alone may be used for beamforming near-field reflectors. Echo data received with the center element 344 may be coherently combined with echo data received with the inner ring element 346 for beamforming mid-field reflectors. Similarly, echo data received with the center element 344 may be coherently combined with echo data received with the inner ring element 346 and the outer ring element 348 for beamforming far-field reflectors.

As with other embodiments using receivers of various sizes, the transitions between "near-field," "mid-field," and "far-field" (or between "near-field" and "far-field" for systems with only two sizes of receive elements) may be defined based on optimal characteristics of the intended imaging application, the particular sizes of the elements to be used, transmitted ultrasound frequencies, and other factors. One advantage of the digital switching methods described herein is that the transition between "near-field," "mid-field," and "far-field" may be changed and redefined after echo data has been received and stored. This may allow for iterative adjustment of such transitions for optimization of image quality or other desired characteristics.

Alternatively, as illustrated in FIG. 10B, each group of three ring sections 342 may be electrically connected to a common receive channel of a receive subsystem so as to allow for electrical switching between "small," "medium," and "large" receive elements. When the three ring sections 344, 346, 348 are arranged in a concentric pattern, the location of the circular center of each of the sections 344, 346, 348 will be the same, thereby simplifying beamforming operations.

As illustrated in FIG. 10B, a center circular element 344 and one or more concentric ring sections 346, 348 may be electrically connected to a common receive channel 330 via switches 352, 354. The switches 352, 354 may be any remotely operable electrical switch, and may include any suitable electromechanical, MEMS, semiconductor or other components. The sub-elements 344, 346, and 348 may be electrically connected in parallel when the switches 352, 354 are closed. In some embodiments, each sub-element 344, 346, 348 may have an independent ground conductor. In other embodiments, the sub-elements 344, 346, 348 may share a common ground conductor.

In use, a ping may be transmitted from a transmit element at a time="t0," and the transition between "near-field," "mid-field," and "far-field" may be defined in terms of time, where "$t_1$" is the time at which the transition from near-field to mid-field occurs and "$t_2$" is the time at which the transition from mid-field to far-field occurs. In this example, both switches 352, 354 may be open during and immediately following transmission of a ping at time t0. Then, at time t1, the inner-ring switch 352 may be closed, thereby electrically combining the signal generated by the inner circular element 344 with the signal generated by the inner-ring transducer element 346. At time t2, the outer-ring switch 354 may also be closed, leaving the inner-ring switch 352 also closed, thereby electrically combining the signal generated by the inner circular element 344 with the signal generated by the inner-ring transducer element 346 and the outer-ring transducer element 348. The resulting echo data string produced by the ping transmitted at t0 will then contain near-field echoes received by the inner circle element 344 alone, mid-field echoes received by the combined inner circular element 344 and the inner ring element 346, and far-field echoes received by all three 344, 346, 348 elements combined.

As with other embodiments described herein, receive elements of various sizes may be made using any suitable manufacturing process or processes. For example, continuous circular disc-shaped elements and ring-shaped elements may be made of a bulk PZT material, other piezoelectric materials, or from arrays of micro-elements or other sub-elements using any of the various manufacturing techniques identified herein. The transducer elements 344, 346, 348 may also have shapes other than circular, such as polygonal or amorphous shapes. Each of the elements 344, 346, 348 may also be made up of multiple micro-elements.

In some embodiments, a center element and one or more concentric ring elements may be formed from a single continuous piece of PZT (or other piezoelectric material) that is plated with an electrically conductive material to form a center element 344 and one or more distinctly-operable rings 346, 348. For example, the ring elements may be defined by rings of plated electrically conductive material in the shape of the desired ring(s) with regions of un-plated material in between adjacent ring elements or between an inner ring and a center element. In some embodiments, ring-shaped plated regions may be formed on both a top and a bottom surface of the piezoelectric material. In other embodiments, ring-shaped sections may be plated on a top surface, and a bottom surface may be continuously plated. In some embodiments using such a continuous piezoelectric structure with plated and un-plated regions, a bias voltage may be applied to an inner ring 346 and/or an outer ring 348 while receiving echoes with a center element in order to dampen unwanted oscillation of the outer region of PZT.

In some embodiments, a switchable group of sub-elements such as that illustrated in FIG. 10B may be used as a transmit element of variable size. For example, differently-shaped waveforms or waveforms of different power levels may be produced by transmitting from the center element 344 alone than by transmitting simultaneously from both the center element 344 and the inner ring element 346, which will in turn be different than a waveform transmitted from all three sub-elements 344, 346, 348.

In some embodiments, the center element 344 may also be switchably connected to a receive system or a transmit system. In some embodiments, the arrangement illustrated in FIG. 10A may be combined with the arrangement in FIG. 10B. That is, each sub-element may be switchable between one of three states: connected to its own receive (or transmit) channel, connected in electrical parallel with one another, or disconnected (i.e., at open circuit relative to the other sub-elements).

Figure 11A:
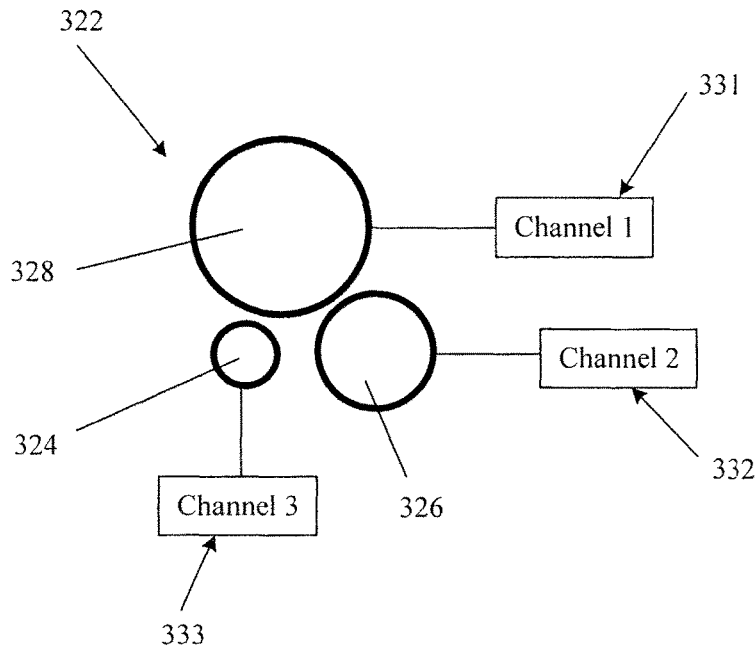
FIG. 11A is a schematic illustration of an embodiment of an electric circuit that may be used to connect a group of circular receive elements of different sizes to separate receive channels of a receive subsystem.

In some embodiments, elements of different sizes may be grouped in different constellations allowing for a different mode of operation. FIG. 11A illustrates elements of multiple sizes arranged in a group 322. In some embodiments, elements of varying sizes may be grouped together, each group 322 including a small element 324, a medium element 326, and a large element 328 positioned close together. In some embodiments, a sparse array may comprise groups of elements of different sizes in which the elements in each group may be spaced from one another by a distance of less than half a wavelength of the ultrasound transmitted and/or received by the elements. In other words, groups 322 of elements may be sparsely positioned relative to other groups, while the elements of each group may be non-sparsely spaced from one another.

In one example, the small element 324 may have a diameter of about 1 mm, the medium element 326 may have a diameter of about 2 mm, and the large element 328 may have a diameter of about 3 mm (any other sizes may also be desired, depending on the needs of a particular application). In other examples, an element constellation 322 may include receive elements of only two sizes or elements of four or more sizes. The individual and relative element sizes used and the relative positions of elements may also be varied depending on the needs of a particular application. In some embodiments, each element of a constellation group 322 may comprise concentric elements as described above with reference to FIG. 10A and/or 10B.

Figure 11B:
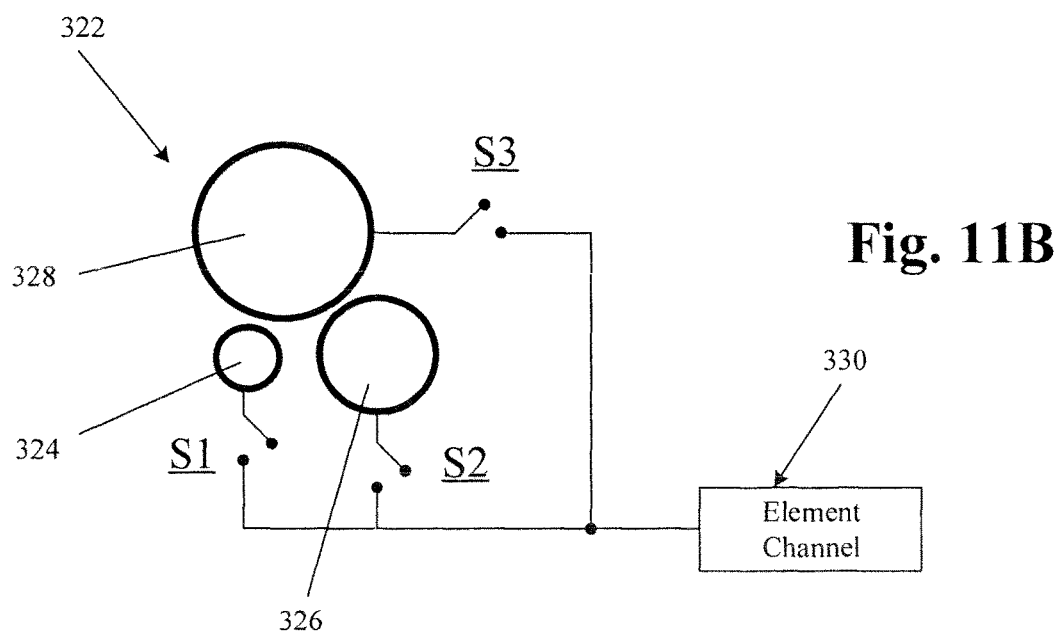
FIG. 11B is a schematic illustration of an embodiment of an electric circuit that may be used to connect a group of circular receive elements of different sizes to a single receive channel of a receive subsystem.

In some embodiments, each element 324, 326, 328 of the constellation of FIG. 11A and the constellation of FIG. 11B may be a micro-element (e.g., a micro-dome as described above or another micro-element structure) or a group of micro-elements.

As described above, smaller-diameter elements may provide optimal receive characteristics for echoes returned by relatively shallow (or near-field) reflectors, while larger-diameter elements may provide optimal receive characteristics for echoes returned by relatively deep (or far-field) reflectors. Therefore, in some embodiments, an imaging system may be configured to switch between using information from elements of various size such that small elements 324 may be used primarily for forming images from echoes received from near-field reflectors, medium-sized elements 326 may be used primarily for forming images from echoes received from mid-field reflectors, and large elements 328 may be used primarily for forming images from echoes received from far-field reflectors.

In some embodiments, this switching may be accomplished digitally by forming a complete image from received echoes after echoes have been received with all receive elements of all sizes. To achieve this digital switching in some embodiments, each of the receive elements 324, 326, 328 of the constellation of FIG. 11A may be individually electrically connected to a separate channel 331, 332, 333 of a receive subsystem. In such embodiments, echoes received by the elements of varying sizes may be digitized and stored in a memory device separately. Stored echoes may then be retrieved from the memory device and combined so as to obtain an optimal image based on the timing of received echoes and/or the location of the transmitted ping.

Because each received echo sample can be mapped to a three-dimensional position within the imaged volume, one or more threshold depths may be established in order to determine which regions of a volume (or 2D image) should be formed with echoes received by small elements, which regions should be formed with echoes received by medium-sized elements, which regions should be formed with echoes received by large elements, and which regions should be formed by combining echoes from small and medium elements or by combining echoes from medium and large elements. Such information can be stored in an imaging controller and used during live imaging or during reconstruction of an image from stored echo data. As with other embodiments described herein, receive element constellations may be grouped into receive apertures, each receive aperture having an overall size selected such that echoes received by multiple elements of a common receive aperture may be combined coherently without phase cancellation. Information obtained from two or more receive apertures may then be combined incoherently.

The digital switching method described above relies on the echoes received by each receive element of each size being individually stored at least temporarily. In alternative embodiments, the number of receive channels used by receive elements of various sizes may be reduced by incorporating switches. For example, as illustrated in FIG. 11B, a receive group 322 including a large element 328, a medium element 326, and a small element 324 may be electrically connected to a single receive channel 330 of a receive subsystem via switches S1, S2, S3. Each of the large 328, medium 326, and small 324 elements may be switched "on" (closed-circuit) during times when that element is expected to return usable (or beneficially-contributing) information. During times when an element of a particular size is not expected to return usable information, the element may be switched "off" (open-circuit) in favor of switching on an element of a different size.

Switching of receive elements will be described with reference to an example. Assume that a ping is transmitted from a transmit element at a time=$t_0$. If the transition between "near-field," "mid-field," and "far-field" is defined in terms of time, where $t_1$ is the time at which the transition from near-field to mid-field occurs and $t_2$ is the time at which the transition from mid-field to far-field occurs, then a single group of three differently-sized receive elements may be switched as follows: only the small element 324 is switched on (e.g., S1 is closed, S2 and S3 are open) from time $t_0$ to $t_1$, only the medium element 326 is switched on (S2 is closed, S1 and S3 are open) from time $t_1$ to $t_2$, and only the large element 328 is switched on (S3 is closed, S1 and S2 are open) from time $t_2$ until the next ping is transmitted (or until such time as all receivable echoes can be expected to have returned). In some embodiments, two or more of the switches S1, S2, S3 may be combined into a single multi-position switch.

In some embodiments, when using differently-sized receive elements in combination with digital or electrical switching, an image formation subsystem may use a physical location of each individual element 324, 326, 328 to identify echo samples corresponding to a particular pixel or voxel location within an imaged region. In the case of digital switching, the position of the circular center of each receive element may be individually stored and associated with the corresponding receive channel for use during beamforming operations. Even in the electrical switching case, because the time at which switching occurs is known, the samples corresponding to the small, medium, and large elements can be determined based on times associated with the data samples, and the appropriate element circular center position information may be used for beamforming echoes received by the elements of different sizes.

In some embodiments, transducer elements of different sizes in a pattern such as that shown in FIG. 1, FIG. 11A, FIG. 11B, FIG. 10A, or FIG. 10B or any other pattern, may be used as transmit elements. For example, planar, concave, or convex elements of any circular, polygonal, or other shape may be provided in two, three, or more different sizes for use as dedicated transmit elements.

In various embodiments, switches used for switching individual micro-elements or groups of micro-elements may include microelectromechanical systems (MEMS) switches of any suitable type. In some embodiments, MEMS switches may be formed on an opposite side of same substrate as the micro-elements. MEMS or other switches may be controllable by transmit subsystems, receive subsystems, or both, as appropriate for a given application.

In some embodiments, low noise amplifiers (LNAs) may also be provided on the back-side of a substrate supporting an array of micro-elements. In some embodiments, one LNA may be provided for each receive element (or group of micro-elements controlled collectively). In other cases, one LNA may be provided for each receive aperture or group of receive elements. In various embodiments, LNAs may also be controlled by one or more elements of an imaging control system, such as a transmit subsystem or a receive subsystem.

Detecting Reflector Position Based on Pattern or Shape of Receive Elements

As described herein, beamforming calculations produce a locus of possible locations for a reflector based on a known position of a transmitter element and a receiver element, and the loci obtained from multiple elements are combined to converge towards an actual location for a given reflector. Therefore, any additional information about the likely position of reflectors may be used to further enhance image quality.

Figure 12:
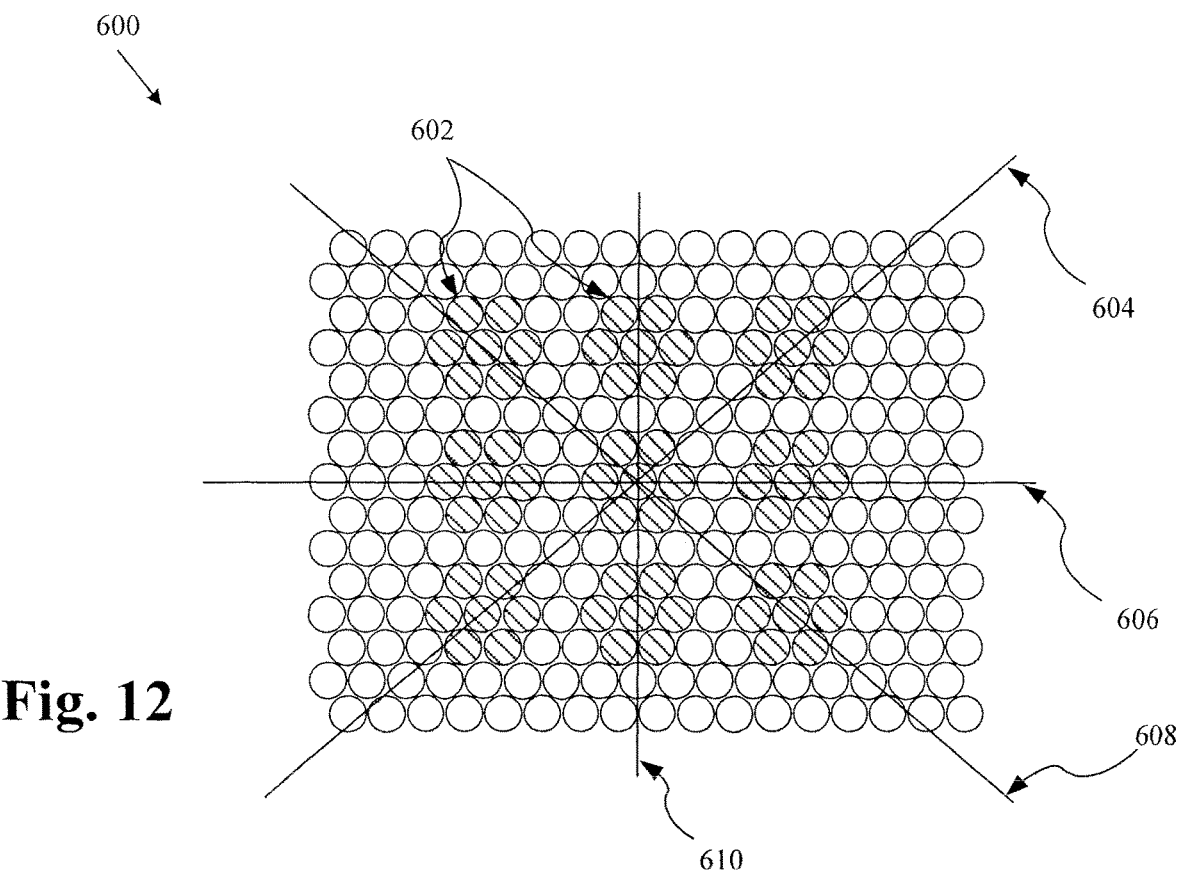
FIG. 12 is a schematic diagram illustrating a plurality of receive transducer elements in a grid pattern, showing axes for determining estimated reflector locations.

In some embodiments, a known pattern of receiver elements may be used to determine an approximate direction from which echoes return to the receiver elements. This may be understood with reference to the illustration in FIG. 12, which shows a pattern 600 of six receive elements 602, each made up of a plurality of micro-elements. The elements 602 are shown arranged in a regular grid pattern for clarity of illustration, but may be irregularly spaced and may be asymmetrically aligned relative to one another. Various axes may be drawn through any two or more transducer elements arranged in the pattern. FIG. 12 illustrates a vertical axis 610, a horizontal axis 606, and two diagonal axes 604, 608. Several other axes could also be drawn, any of which could be used with the same methods.

For echoes of a given reflector arriving at the receive elements 602, the beamforming process will determine the locus of possible location points for the reflector based on the position of the transmitter and the positions of each of the receive elements 602. In some embodiments, the system may also compare the absolute time-of-arrival of the echoes of the given reflector at elements along one or more of the axes (604, 606, 608, 610). For example, if the upper-right element along the diagonal axis 604 receives an echo of the given reflector at an earlier time than the same echoes arrive at the center element (a time measured in nanoseconds), then it may be reasonable to conclude that the reflector is located in a portion of the region of interest closer to the upper-right quadrant of the array section.

This location estimate information may be supported or confirmed by comparing the arrival time of the given reflector echoes at the upper-right element with the arrival time of the same given reflector echoes at the lower left element. Additional elements along the same axis may also be used to further confirm an estimate of an origin of the reflector. Comparing arrival times of the same given reflector along other axes may provide further information about the approximate location of the reflector.

In some embodiments, a process of axis-based direction estimation may include: transmitting an unfocused ultrasound ping from a transmitter approximating a point source into an object to be imaged. Echoes of the transmitted ping may then be received at a first receive element and a second receive element, where a line between the first receive element and the second receive element defines an axis. The first receive element and the second receive element may be located at known positions relative to a common coordinate system (e.g., based on position data retrieved from a data store). The process may proceed by identifying a first echo sample corresponding to a first reflector received at the first element, and identifying a second echo sample corresponding to the same first reflector received at the second element. A first time-of-arrival may be determined for the time at which the first sample echo was received at the first receive element. The first time-of-arrival may be based on explicit or implicit timing information in the stored echo data. Explicit timing information may include specific clock times recorded along with each received echo sample. Implicit timing information may include a known sample rate and a sample position (or interpolated sample position) of a particular sample relative to some baseline (e.g., a start-of-ping time). A second time-of-arrival may be determined for the time at which the second sample echo was received at the second receive element. The first and second times-of-arrival may then be compared to determine which of the elements first received the echo sample corresponding to the first reflector. The element that received the first reflector's echo sample first is closest to the reflector along the axis. This information may then be used for other elements along the same axis.

Based on the estimated given reflector position information obtained above, echoes of the given reflector received by elements that are further away from the estimated reflector position may be weighted lower than echoes of the same reflector received by elements closer to the estimated position of the reflector. It the first reflector is closer to the first receiver element along the axis, then the echoes of the first reflector received by the first element may be weighted higher than the echoes of the first reflector received by the second element when the echoes are combined to form an image. The same information may also be used to weight echoes of the same first reflector received by other elements along the same axis. That is, echo contributions from receive elements determined to be closer to the reflector along the axis may be given more weight (i.e., a larger weighting factor) than echo contributions from receive elements further away from the reflector along the axis.

Figure 13:
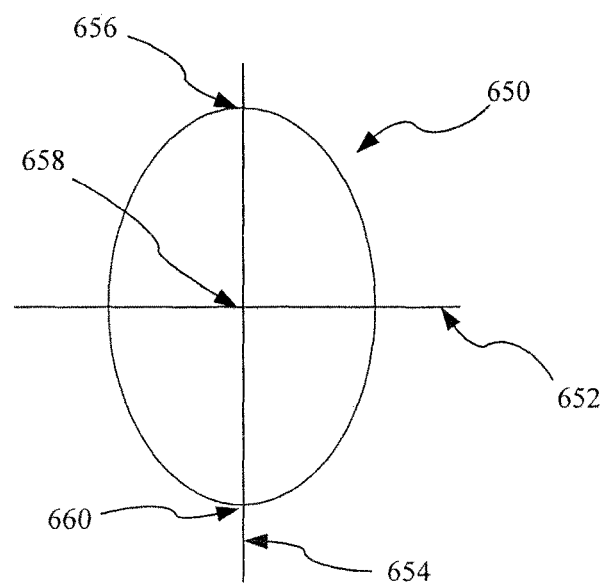
FIG. 13 is a schematic diagram illustrating an asymmetrical receive transducer element with a long axis and a short axis.

In some embodiments, one or more asymmetrically-shaped receive elements may be used to estimate an approximate location of a reflector in order to improve image quality. For example, FIG. 13 illustrates receive transducer element 650 with a generally elliptical shape having a long axis 654 and a short axis 652. Echoes with strong directional components along one or both axes of such an asymmetrical element will produce recognizable phase patterns due to the asymmetry. The different phase patterns may be due to phase differences of echoes arriving predominantly along each axis.

For example, assume an echo returning to the element 650 with a strong component along the long axis 656 arrives at the top point 656 at a first time, then arrives at the center point 658 at a second time after the first time, and finally arrives at the bottom point 660 at a third time after the second time. The echoes of a single reflector arriving to the upper point 656 will be slightly out of phase with the echoes of the same reflector arriving at the middle 658 and lower points 660. In the same way, echoes arriving at different times at different points along the short axis 652 may also exhibit a unique phase pattern.

For a given shaped asymmetrical receive element, the phase pattern along each axis can be calibrated by transmitting pings from known transmit positions relative to the asymmetrical receive element and measuring the phase response. Then the approximate direction of each arriving echo can be estimated based on the phase pattern response of the asymmetrical receiver(s). The calibration set of various phase patterns corresponding to various origin points may be stored, and used during imaging to estimate the approximate location of reflectors by comparing echo phase patterns with the calibration set phase patterns.

In various embodiments, a wide range of asymmetrical receive element shapes may be used to estimate approximate reflector locations. For example, any shape with at least one generally long axis and one generally shorter axis may be used. Such shapes may include elongated irregular polygons such as rectangles or rectangles with rounded corners, oblong shapes, oval shapes, or generally elongated amorphous shapes.

In various embodiments, each receive aperture may include only one, two, three, four, five, or more asymmetrical receivers. In other embodiments, an entire array of receive elements may be asymmetrical. Asymmetrical elements need not all be aligned with long axes in the same direction as one another, and in some embodiments it may be desirable to provide asymmetrical elements with long axes perpendicular to one another.

In various embodiments, asymmetrical transducer elements may be formed of any transducing material and using any manufacturing process, including those described elsewhere herein. For example, asymmetrical elements may be formed from a group of micro-elements in a micro-element array.

Although the examples of shaped receive elements above are described relative to arrays made up of micro-elements, the same techniques and principles may also be applied using elements of different constructions made by various other manufacturing processes. For example, the techniques may also be applied using machined bulk PZT elements.

Sparse Arrays with Overlapping Micro-Element Groups

Figure 14:
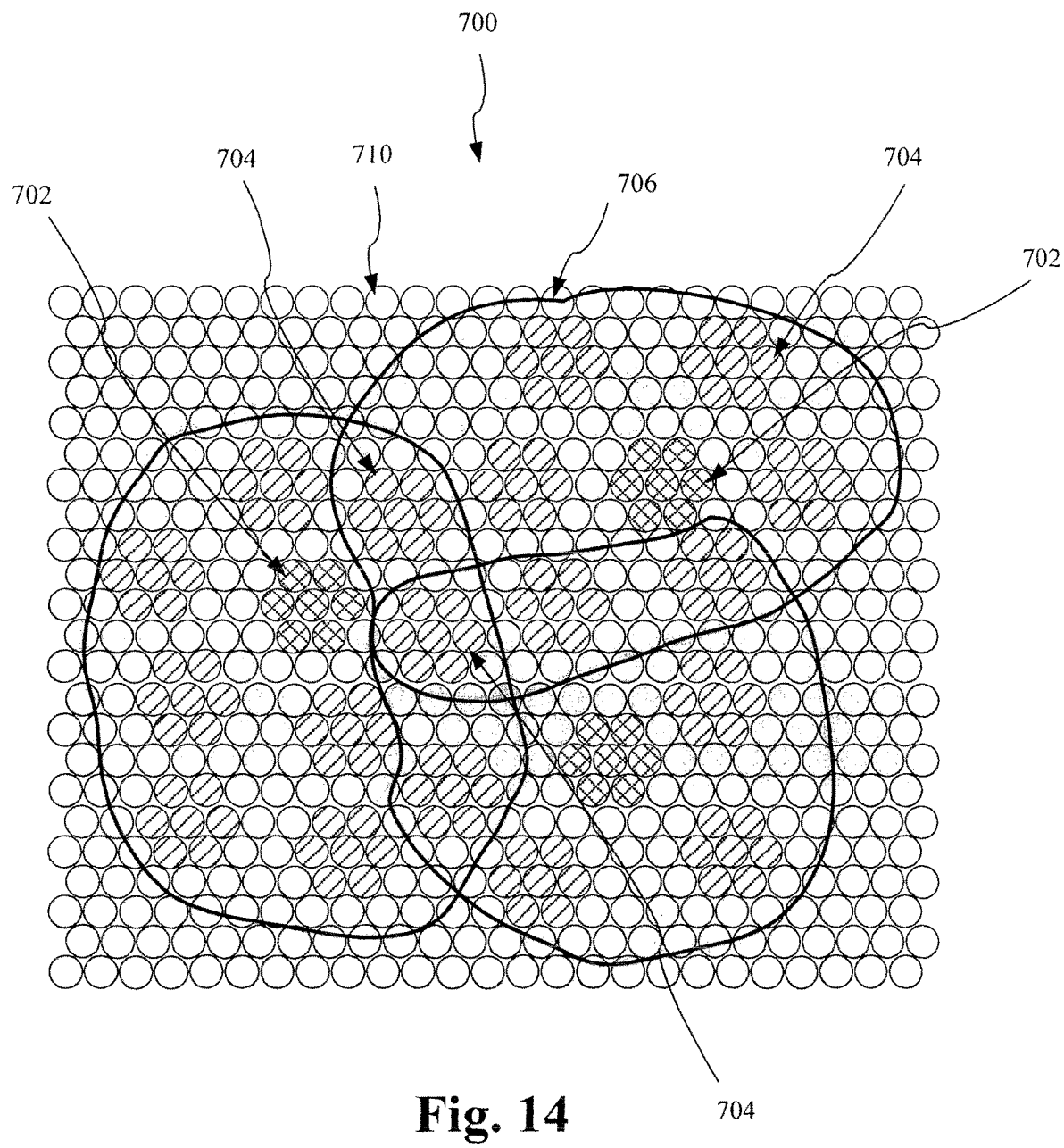
FIG. 14 is a schematic diagram illustrating a constellation configuration of ultrasound transmit elements surrounded by receive elements grouped into overlapping receive apertures based, at least in part, on proximity to transmit elements.

In some embodiments, it may be desirable to configure a ping-based ultrasound imaging probe with dedicated transmitter elements and receive elements grouped into overlapping receive apertures in a constellation configuration. For example, FIG. 14 illustrates an array 700 of micro-elements 710 in which micro-elements are grouped into transmit element groups and receive element groups.

As shown, each transmit element group 702 (indicated by "X" hatched micro-elements) may be surrounded by a plurality of receive element groups 704 (indicated by "/" hatched micro-elements). In various embodiments, receive elements 704 may be grouped into receive apertures 706 based on their proximity to a transmit element 702. Receive apertures 706 are indicated by the lines drawn around groups of receive elements 704. As shown, some elements may participate in two or more different receive apertures 704.

As with other embodiments described herein, each receive element may be connected to a separate channel in a receive subsystem such that echoes received by each receive element may be independently stored. Therefore, receive elements may be assigned to apertures after echo data has been collected. In some cases, receive elements may be assigned to apertures based on the known positions of receive elements relative to known positions of transmit elements.

In any of the probe embodiments described in this disclosure, point source transmitters may take any suitable form, such as a single bulk piezoelectric element, a segmented piezoelectric element, a coordinated group of bulk piezoelectric elements, or a dedicated transmitter group of micro-elements which may be operated to transmit spherical waveform pings from an apparent point source at a geometric center of the transmitter group. Micro-elements making up a transmitter group may be arranged in a planar arrangement relative to one another. Alternately, micro-elements making up a transmitter group of micro-elements may be arranged on a locally concave or convex substrate so as to form an apparent-point-source transducer element.

Sparse Array Probes with Physical Gaps

In various embodiments, transmitter micro-element groups and/or receiver micro-element groups may be made in any other planar, convex, concave, concave and convex, or amorphous shape. For example, micro-element groups may be formed in approximately square shapes, approximately circular shapes, approximately polygonal shapes, approximately concentric ring shapes, etc. Overall dimensions of transmitter micro-element groups and receiver micro-element groups may be sized as described elsewhere in this disclosure. In some cases, transmitter micro-element groups may be the same size as receiver micro-element groups, e.g., with dimensions of between about 150 microns and about 0.5 mm or more.

In various embodiments, the use of a sparse array configuration may allow for other uses of regions in between transducer elements. For example, various treatment structures may be provided in spaces between transducer elements. Such treatment structures may include high frequency ultrasound (HIFU) transmitters for delivering targeted ablative US treatment, radiation or drug delivery elements, lasers or radio frequency (RF) delivery elements, or any other structures for treating or diagnosing a patient that may be positioned in spaces between transducer elements contributing to a unified image.

In some embodiments, vacuum ports may be provided between transducer elements for causing a tissue or other medium to be drawn into contact with a surface of the imaging probe. Vacuum ports may comprise holes and/or channels in the substrate, support structures, matching layers, lensing layers, etc.

In some embodiments, sparse array probes may be configured with openings or gaps through which instruments or tools may be inserted. For example, probes may be configured with gaps sized and configured to receive instruments or tools such as scalpels, scrapers, biopsy tools, robotic arms, needles, surgical tools, or other implements.

FIG. 15 illustrates an ultrasound probe made up of a circular array 800 of transducer elements 802 with a gap 810 in the center. The circular array 800 may be made up of array segments 812, 814, 816, 818. For example, FIG. 15 shows a probe array made up of four pie-slice segments each in the shape of a quarter-circular segment. The segments may be rigidly fixed in a housing, bracket, or other structural support configured to hold the segments in a consistent position relative to one another. The central gap 810 may be sized to allow insertion of various tools or instruments as discussed above.

Using ping-based multiple aperture imaging techniques, the region immediately under the probe gap 810 may be imaged by transmitting spherical ping signals that insonify the region under the gap, and receiving echoes with receive elements 802 near the gap 810. In some embodiments, transducer elements closer to the central gap 810 may be spaced more closely to one another so as to provide more receive elements adjacent to the gap, thereby increasing the number of receivers that may receive echoes from reflectors lying under the gap 810.

Transmit transducer elements will tend to produce spherical waveforms that propagate in all directions extending from the point-source transmitter element into the imaged object. At some angle from normal, the strength of the transmitted energy will typically tend to drop off dramatically, thereby defining a threshold angle. Rotating a single angle about the point-source defines a "signal cone." Reflectors within the signal cone will tend to provide sufficiently high signal-to-noise reflections that they may be reliably imaged, while reflectors outside of the signal cone may tend to return echoes with too little energy to provide valuable contributions to the final image. The signal cone for any particular transmit transducer element may be determined empirically by experimentation. Receive elements may have a similar signal cone of positively-contributing reflectors. As described herein, the angle of a transducer element's signal cone may be related to the size of the element with smaller elements generally having a wider signal cone than larger elements. On the other hand, larger elements may produce more energy (or may be sensitive to weaker received signals) than smaller elements.

Based on the size of the gap and the angles of transmitter signal cones and receiver signal cones, transmitter elements and receiver elements may be positioned relative to the gap 810 so as to allow effective imaging of the volume below the gap 810. For example, in some cases, transmitter elements and receiver elements with wide signal cones (also referred to as "look angles") may be positioned in a higher density adjacent to the gap, while transmit and receive elements with narrower signal cones may be positioned further from the gap. As described in various examples herein, transmitter elements and receiver elements of various or variable sizes may be used based on the energy requirements and signal cone shapes.

FIG. 16A and FIG. 16B illustrate another example of an ultrasound probe 850 with a physical gap 852 separating array segments 854, 856. The probe 850 of FIG. 16A and FIG. 16B is generally configured to provide real-time volumetric imaging of a region below both array segments including the region below the gap 852 between the segments. The gap 852 may be used for performing various surgical, diagnostic, or interventional procedures.

The probe 850 of FIG. 16A and FIG. 16B may include a bridge handle 860 rigidly joining the two array segments 854, 856 and containing conduits for electrical connections. The bridge handle may take any shape and structure as needed in order to rigidly hold the array segments in consistent positions relative to one another. Based on the size of the gap 852 and the angles of transmitter signal cones and receiver signal cones, transmitter elements and receiver elements may be positioned relative to the gap 852 so as to allow effective imaging of the volume below the gap 852. As above, transmitter and receiver elements 862 of various or variable sizes may be used based on the energy requirements and signal cone shapes.

Multiple Aperture Ultrasound Imaging System Components

Figure 17:
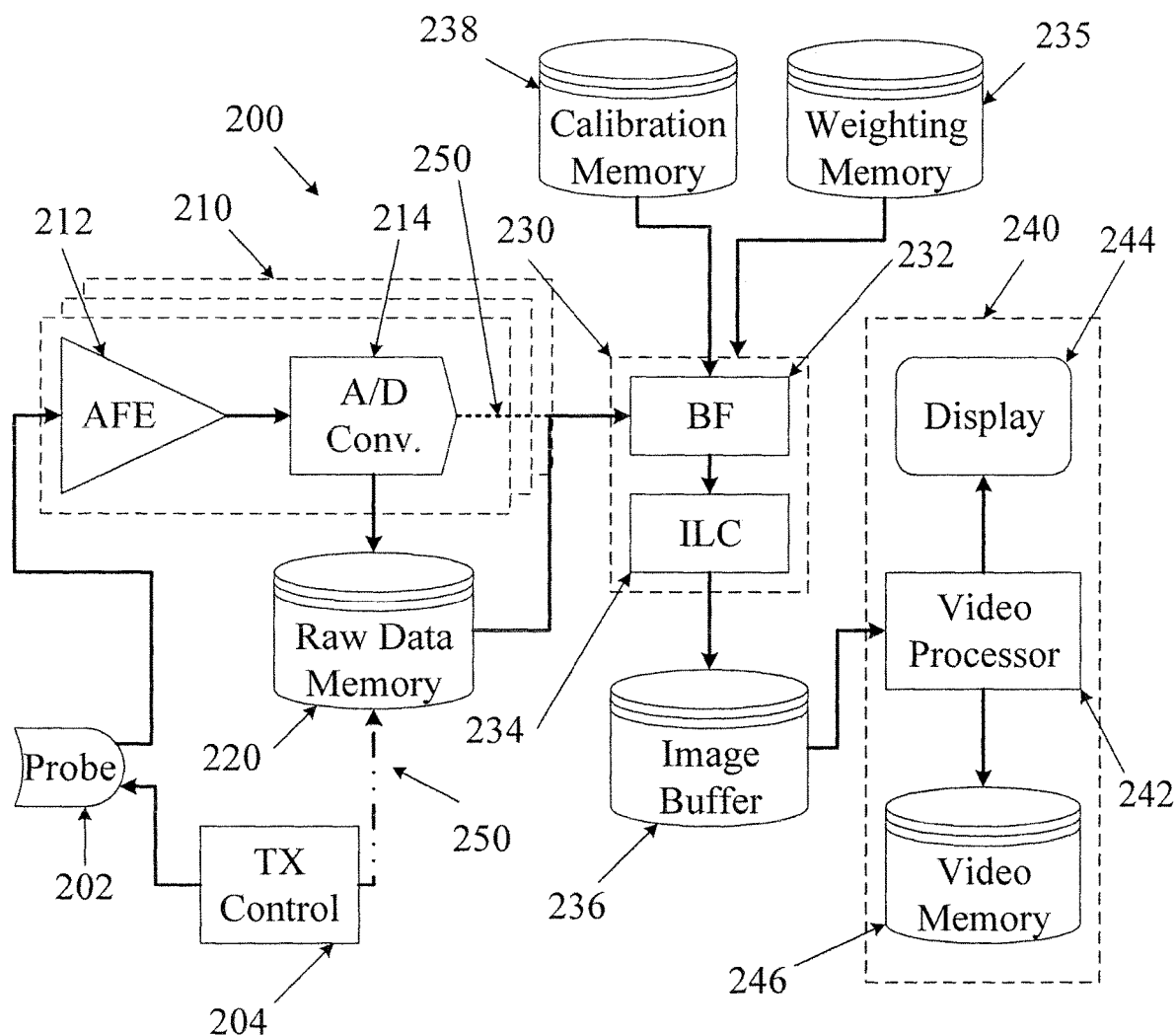
FIG. 17 is a schematic block diagram illustrating example components in an embodiment of a multiple aperture imaging system.

The block diagram of FIG. 17 illustrates components of an ultrasound imaging system 200 that may be used in combination with various embodiments of systems and methods as described herein. The system 200 of FIG. 17 may include several subsystems: a transmit control subsystem 204, a probe subsystem 202, a receive subsystem 210, an image generation subsystem 230, and a video subsystem 240. In various embodiments, the system 200 may also include one or more memory devices for containing various data for use during one or more ultrasound imaging steps. Such memory devices may include a raw echo data memory 220, a weighting factor memory 235, a calibration data memory 238, an image buffer 236 and/or a video memory 246. In various embodiments all data (including software and/or firmware code for executing any other process) may be stored on a single memory device. Alternatively, separate memory devices may be used for one or more data types.

The transmission of ultrasound signals from elements of the probe 202 may be controlled by a transmit control subsystem 204. In some embodiments, the transmit control subsystem 204 may include any combination of analog and digital components for controlling transducer elements of the probe 202 to transmit un-focused ultrasound pings at desired frequencies and intervals from selected transmit apertures according to a desired imaging algorithm. In some embodiments a transmit control system 204 may be configured to transmit ultrasound pings at a range of ultrasound frequencies. In some (though not all) embodiments, the transmit control subsystem may also be configured to control the probe in a phased array mode, transmitting focused (i.e., transmit beamformed) ultrasound scanline beams.

In some embodiments, a transmit control sub-system 204 may include a transmit signal definition module 206 and a transmit element control module 208. The transmit signal definition module 206 may include suitable combinations of hardware, firmware and/or software configured to define desired characteristics of a signal to be transmitted by an ultrasound probe. For example, the transmit signal definition module 206 may establish (e.g., based on user inputs or on pre-determined factors) characteristics of an ultrasound signal to be transmitted such as a pulse start time, pulse length (duration), ultrasound frequency, pulse power, pulse shape, pulse direction (if any), pulse amplitude, transmit aperture location, or any other characteristics.

The transmit element control module 208 may then take information about the desired transmit pulse and determine the corresponding electrical signals to be sent to the appropriate transducer elements in order to produce this signal. In various embodiments, the signal definition module 206 and the transmit element control module 208 may comprise separate electronic components, or may include portions of one or more common components.

Upon receiving echoes of transmitted signals from a region of interest, the probe elements may generate time-varying electrical signals corresponding to the received ultrasound vibrations. Signals representing the received echoes may be output from the probe 202 and sent to a receive subsystem 210. In some embodiments, the receive subsystem may include multiple channels, each of which may include an analog front-end device ("AFE") 212 and an analog-to-digital conversion device (ADC) 214. In some embodiments, each channel of the receive subsystem 210 may also include digital filters and data conditioners (not shown) after the ADC 214. In some embodiments, analog filters prior to the ADC 214 may also be provided. The output of each ADC 214 may be directed into a raw data memory device 220. In some embodiments, an independent channel of the receive subsystem 210 may be provided for each receive transducer element of the probe 202. In other embodiments, two or more transducer elements may share a common receive channel.

In some embodiments, an analog front-end device 212 (AFE) may perform certain filtering processes before passing the signal to an analog-to-digital conversion device 214 (ADC). The ADC 214 may be configured to convert received analog signals into a series of digital data points at some pre-determined sampling rate. Unlike most ultrasound systems, some embodiments of the ultrasound imaging system of FIG. 17 may then store digital data representing the timing, phase, magnitude and/or the frequency of ultrasound echo signals received by each individual receive element in a raw data memory device 220 before performing any further receive beamforming, filtering, image layer combining or other image processing.

In order to convert the captured digital samples into an image, the data may be retrieved from the raw data memory 220 by an image generation subsystem 230. As shown, the image generation subsystem 230 may include a beamforming block 232 and an image layer combining ("ILC") block 234. In some embodiments, a beamformer 232 may be in communication with a calibration memory 238 that contains probe calibration data. Probe calibration data may include information about the precise position, operational quality, and/or other information about individual probe transducer elements. The calibration memory 238 may be physically located within the probe, within the imaging system, or in location external to both the probe and the imaging system.

In some embodiments, after passing through the image generation block 230, image data may then be stored in an image buffer memory 236 which may store beamformed and (in some embodiments) layer-combined image frames. A video processor 242 within a video subsystem 240 may then retrieve image frames from the image buffer, and may process the images into a video stream that may be displayed on a video display 244 and/or stored in a video memory 246 as a digital video clip, e.g., as referred to in the art as a "cine loop".

In some embodiments, the AFE 212 may be configured to perform various amplification and filtering processes to a received analog signal before passing the analog signal to an analog-to-digital conversion device. For example, an AFE 212 may include amplifiers such as a low noise amplifier (LNA), a variable gain amplifier (VGA), a bandpass or lowpass/anti-aliasing filter, and/or other amplification or filtering devices. In some embodiments, an AFE device 212 may be configured to begin passing an analog signal to an ADC 214 upon receiving a trigger signal. In other embodiments, an AFE device can be "free running", continuously passing an analog signal to an ADC.

In some embodiments, each analog-to-digital converter 214 may generally include any device configured to sample a received analog signal at some consistent, predetermined sampling rate. For example, in some embodiments, an analog-to-digital converter may be configured to record digital samples of a time-varying analog signal at 25 MHz, which is 25 million samples per second or one sample every 40 nanoseconds. Thus, data sampled by an ADC may simply include a list of data points, each of which may correspond to a signal value at a particular instant. In some embodiments, an ADC 214 may be configured to begin digitally sampling an analog signal upon receiving a trigger signal. In other embodiments, an ADC device can be "free running", continuously sampling a received analog signal.

In some embodiments, the raw data memory device 220 may include any suitable volatile or non-volatile digital memory storage device. In some embodiments, the raw data memory 220 may also comprise communication electronics for transmitting raw digital ultrasound data to an external device over a wired or wireless network. In such cases, the transmitted raw echo data may be stored on the external device in any desired format. In other embodiments, the raw data memory 220 may include a combination of volatile memory, non-volatile memory and communication electronics.

In some embodiments, the raw data memory device 220 may comprise a temporary (volatile or non-volatile) memory section, and a long-term non-volatile memory section. In an example of such embodiments, the temporary memory may act as a buffer between the ADC 214 and the beamformer 232 in cases where the beamformer 232 may be unable to operate fast enough to accommodate data at the full rate from the ADC 214. In some embodiments, a long-term non-volatile memory device may be configured to receive data from a temporary memory device or directly from the ADC 214. Such a long-term memory device may be configured to store a quantity of raw echo data for subsequent processing, analysis or transmission to an external device.

In some embodiments, the beamforming block 232 and the image layer combining block 234 may each include any digital signal processing and/or computing components configured to perform the specified processes (e.g., as described below). For example, in various embodiments the beamforming 232 and image layer combining 234 may be performed by software running on a single GPU, on multiple GPUs, on one or more CPUs, on combinations of CPUs & GPUs, on single or multiple accelerator cards or modules, on a distributed processing system, or a clustered processing system. Alternatively, these or other processes may be performed by firmware running on an FPGA (Field Programmable Gate Array) architecture or one or more dedicated ASIC (Application-Specific Integrated Circuit) devices.

In some embodiments, the video processor 242 may include any video processing hardware, firmware and software components that may be configured to assemble image frames into a video stream for display and/or storage.

In any embodiment, a plurality of elements may share one or more conductors in a multiplexed arrangement, such as time-division-multiplexed communications, or other multiplexing methods. Multiplexing signals may allow for a cable size to be reduced without sacrificing the benefits of individual channels for each element.

In any embodiment, the exact acoustic location of each transmit element and each receive element may be determined by precision manufacturing, by calibration, or some combination of both. Such element location information may be stored and made available to an image-formation and/or beamforming system.

Certain Terminology

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Various modifications to the above embodiments will be readily apparent to those skilled in the art, and the generic principles defined herein may be applied to other embodiments without departing from the spirit or scope of the invention. Thus, it is intended that the scope of the present invention herein disclosed should not be limited by the particular disclosed embodiments described above, but should be determined only by a fair reading of the claims that follow.

In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. Also as used herein, unless explicitly stated otherwise, the term "or" is inclusive of all presented alternatives, and means essentially the same as the commonly used phrase "and/or." It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific tennis used herein have the same meaning as commonly understood by one of ordinary skill in the art to which this invention belongs.

Certain features that are described in this disclosure in the context of separate implementations can also be implemented in combination in a single implementation. Conversely, various features that are described in the context of a single implementation can also be implemented in multiple implementations separately or in any suitable subcombination. Although features may be described above as acting in certain combinations, one or more features from a claimed combination can, in some cases, be excised from the combination, and the combination may be claimed as any subcombination or variation of any subcombination. Further, the claims may be drafted to exclude any disclosed element. As such, the foregoing sentence is intended to serve as antecedent basis for use of such exclusive terminology as "solely," "only" and the like in connection with the recitation of claim elements, or use of a "negative" limitation.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Some embodiments have been described in connection with the accompanying drawings. Some of the figures may be drawn to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

What is claimed is:

1. A ping-based ultrasound transducer probe comprising:
an array of ultrasound transducing micro-elements, where each micro-element has a diameter less than 500 microns;
a first group of micro-elements electrically connected to a first signal conductor;
a second group of micro-elements electrically connected to a second signal conductor, the second signal conductor being electrically separate from the first signal conductor; and
a third group of micro-elements positioned between the first group and the second group, the third group of micro-elements being permanently disconnected from any signal conductors
wherein at least a majority of micro-elements of the array are spaced from adjacent micro-elements by a distance of half of a maximum operating wavelength of the array.

2. The transducer probe of claim 1 wherein each micro-element has a diameter between 25 microns and 200 microns.

3. The transducer probe of claim 1 wherein some of the micro-elements of the first group are differently sized than other micro-elements of the first group, wherein the size of a micro-element corresponds its fundamental operating frequency.

4. The transducer probe of claim 1 wherein the micro-elements of the first group are connected to a first ground conductor and the micro-elements of the second group are connected to a second ground conductor not electrically connected to the first ground conductor.

5. The transducer probe of claim 1 wherein the first group of micro-elements includes more micro-elements than the second group.

6. The transducer probe of claim 1 wherein the first group of micro-elements collectively forms a dedicated transmit element and the second group of micro-elements collectively forms a dedicated receive element.

7. The transducer probe of claim 1 further comprising a fourth group of micro-elements electrically connected to the first signal conductor by a switch that, when closed causes the fourth group to form a combined element with first group.

8. The transducer probe of claim 7, wherein the micro-elements of the fourth group collectively surround the micro-elements of the first group.

9. The transducer probe of claim 7, wherein the fourth group of micro-elements is adjacent to the first group of micro-elements.

10. The transducer probe of claim 7, wherein the combined element has a different shape than the first group alone.

11. The transducer probe of claim 7, wherein the combined element has a shape that is the same as a shape of the first group but a different size.

\* \* \* \* \*